(12) United States Patent
Ando et al.

(10) Patent No.: US 9,207,238 B2
(45) Date of Patent: Dec. 8, 2015

(54) ANTI-FOLR1 ANTIBODY

(71) Applicant: KYOWA HAKKO KIRIN CO., LTD, Tokyo (JP)

(72) Inventors: Munetoshi Ando, Tokyo (JP); Hiroshi Ando, Tokyo (JP); Mariko Nakano, Tokyo (JP); Naoya Kameyama, Tokyo (JP); Tsuguo Kubota, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 14/088,550

(22) Filed: Nov. 25, 2013

(65) Prior Publication Data

US 2014/0205610 A1    Jul. 24, 2014

Related U.S. Application Data

(60) Provisional application No. 61/734,610, filed on Dec. 7, 2012, provisional application No. 61/734,547, filed on Dec. 7, 2012.

(51) Int. Cl.

| | | |
|---|---|---|
| *A61K 39/395* | (2006.01) |
| *C07K 16/28* | (2006.01) |
| *G01N 33/569* | (2006.01) |
| *C12N 15/09* | (2006.01) |
| *G01N 33/574* | (2006.01) |
| *G01N 33/566* | (2006.01) |
| *C12P 21/02* | (2006.01) |

(52) U.S. Cl.
CPC ........ *G01N 33/56966* (2013.01); *A61K 39/395* (2013.01); *C07K 16/28* (2013.01); *C12N 15/09* (2013.01); *C12P 21/02* (2013.01); *G01N 33/566* (2013.01); *G01N 33/574* (2013.01); *G01N 33/57407* (2013.01); *G01N 33/57492* (2013.01); *C07K 2317/24* (2013.01); *C07K 2317/33* (2013.01); *C07K 2317/34* (2013.01); *C07K 2317/41* (2013.01); *C07K 2317/73* (2013.01); *C07K 2317/732* (2013.01); *C07K 2317/734* (2013.01); *C07K 2317/92* (2013.01)

(58) Field of Classification Search
CPC .............................. A61K 39/395; C07K 16/28
See application file for complete search history.

(56) References Cited

U.S. PATENT DOCUMENTS

| | | |
|---|---|---|
| 2005/0232919 A1 | 10/2005 | Grasso et al. |
| 2006/0239910 A1 | 10/2006 | Nicolaides et al. |
| 2007/0148165 A1 | 6/2007 | Shitara et al. |
| 2009/0274697 A1 | 11/2009 | Grasso et al. |
| 2009/0324594 A1 | 12/2009 | Nicolaides et al. |
| 2011/0009600 A1 | 1/2011 | Shitara et al. |
| 2012/0010387 A1 | 1/2012 | Niwa et al. |
| 2012/0164137 A1 | 6/2012 | Sass et al. |
| 2012/0171200 A1 | 7/2012 | Nicolaides et al. |
| 2013/0189272 A1 | 7/2013 | Grasso et al. |

FOREIGN PATENT DOCUMENTS

| | | |
|---|---|---|
| JP | 2008500025 A | 1/2008 |
| JP | 2009521206 A | 6/2009 |
| WO | 2007011041 A1 | 1/2007 |
| WO | 2011108502 A1 | 9/2011 |

OTHER PUBLICATIONS

International Search Report issued Feb. 18, 2014 by Japanese Patent Office in counterpart Japanese application No. PCT/JP2013/081616.
Ebel, W. et al., "Preclinical evaluation of MORAb-003, a humanized monoclonal antibody antagonizing folate receptoraplha", Cancer Immunity, vol. 7 No. 12; Mar. 2007; 8 pages total.
Macor, P. et al., "Complement Activated by Chimeric Anti-Folate Receptor Antibodies Is an Efficient Effector System to Control Ovarian Carcinoma", Cancer Research; vol. 66 No. 7; Apr. 2006; 8 pages total.
O'Shannessy, et al., "Characterization of the Human Folate Alpha Via Novel Antibody-Based Probes," Oncotarget; vol. 2 No. 12; Dec. 2011; 17 pages total.

*Primary Examiner* — Ruixiang Li
(74) *Attorney, Agent, or Firm* — Sughrue Mion, PLLC

(57) ABSTRACT

The present invention provides an anti-human FOLR1 antibody against diseases associated with human FOLR1-expressing cells, which specifically recognizes and binds to an amino acid sequence of human FOLR1 or a conformational structure thereof and also has a high effector activity such as antibody-dependent cellular cytotoxicity activity (ADCC activity). The present invention can provide a monoclonal antibody which specifically recognizes and binds to the amino acid sequence of human FOLR1 or the conformational structure thereof and also has ADCC activity and CDC activity, or an antibody fragment thereof, a DNA encoding the antibody, a vector comprising the DNA, a transformant obtained by introducing the vector, a method for producing the antibody or the antibody fragment thereof using the transformant, and a therapeutic agent and a diagnostic agent comprising the antibody or the antibody fragment as an active ingredient.

6 Claims, 10 Drawing Sheets

FIG. 1

```
              1234567890123456789012345678901234567890 12345 67890123456789 0123456789012345678
RA15-7        EVKLLESGGGLVQPGGSMRLSCAASGFTFT           DFYMN WIRQPAGKAPEWLG FIRNKANGYTTEFNPSVKG
HV0           EVQLVESGGGLVQPGGSLRLSCAASGFTFS                 WVRQAPGKGLEWVG
HV2           EVQLVESGGGLVQPGGSLRLSCAASGFTFS                 WVRQPPGKGLEWVG
HV3           EVQLVESGGGLVQPGGSLRLSCAASGFTFS                 WVRQAAGKGPEWVG
HV4           EVQLVESGGGLVQPGGSLRLSCAASGFTFS                 WVRQPAGKGPEWVG
HV5           EVQLVESGGGLVQPGGSLRLSCAASGFTFS           CDR1  WIRQPAGKGPEWLG  CDR2
HV6           EVQLVESGGGLVQPGGSLRLSCAASGFTFS                 WIRQPAGKGPEWLG
HV7           EVQLVESGGGLVQPGGSLRLSCAASGFTFT                 WVRQPPGKAPEWLG
HV8           EVQLVESGGGLVQPGGSLRLSCAASGFTFS                 WIRQPAGKAPEWLG
HV10          EVQLVESGGGLVQPGGSMRLSCAASGFTFT                 WIRQPAGKAPEWLG 901234567890123456789012345678901234567890 1234567890123 45678901234
RA15-7        RFAISRDNTQNMLYLQMNTLRAEDTATYYCAR           CLYGYAYYYVMDA WGQGTSVTVSS
HV0           RFTISRDDSKNSLYLQMNSLKTEDTAVYYCAR                         WGQGTLVTVSS
HV2           RFTISRDDSKNSLYLQMNSLKTEDTATYYCAR                         WGQGTLVTVSS
HV3           RFTISRDDSKNSLYLQMNSLKTEDTATYYCAR                         WGQGTLVTVSS
HV4           RFTISRDDSKNSLYLQMNSLKTEDTATYYCAR           CDR3          WGQGTLVTVSS
HV5           RFTISRDDSKNSLYLQMNSLKTEDTAVYYCAR                         WGQGTLVTVSS
HV6           RFTISRDDSKNSLYLQMNSLKTEDTATYYCAR                         WGQGTLVTVSS
HV7           RFTISRDNSKNSLYLQMNSLKTEDTATYYCAR                         WGQGTLVTVSS
HV8           RFTISRDNSKNSLYLQMNSLKTEDTATYYCAR                         WGQGTLVTVSS
HV10          RFTISRDNSKNSLYLQMNSLKTEDTATYYCAR                         WGQGTLVTVSS
```

FIG. 2

```
              1234567890123456789 0123 45678901234 567890123456789 0123456
RA15-7        DIQMTQSPASLSASLGETVTIEC   RTSEDIFRNLA WYQQRPGNSPQLLIY DTNRLAD
LV0           DIQMTQSPSSLSASVGDRVTITC               WYQQKPGKAPKLLIY
LV2           DIQMTQSPSSLSASVGDRVTITC               WYQQKPGKAPQLLIY
LV3           DIQMTQSPSSLSASLGDRVTITC   CDR1        WYQQKPGKAPKLLIY  CDR2
LV4           DIQMTQSPSSLSASLGDRVTITC               WYQQKPGKAPQLLIY
LV6           DIQMTQSPSSLSASLGDRVTITC               WYQQKPGKSPQLLIY 78901234567890123456789012345678 901234567 8901234567
RA15-7        GVPSRFSGSGSGTQYSLKINSLQSEDVAGYFC  QQYDNYPLT FGSGTKLEIK
LV0           GVPSRFSGSGSGTDFTLTISSLQPEDFATYYC            FGQGTKLEIK
LV2           GVPSRFSGSGSGTDYTLTISSLQPEDFATYYC            FGQGTKLEIK
LV3           GVPSRFSGSGSGTDYTLTISSLQPEDFATYFC  CDR3      FGQGTKLEIK
LV4           GVPSRFSGSGSGTDYTLTISSLQPEDFATYFC            FGQGTKLEIK
LV6           GVPSRFSGSGSGTDYTLTISSLQPEDFAGYFC            FGQGTKLEIK
```

FIG. 4
(a) DNPDF
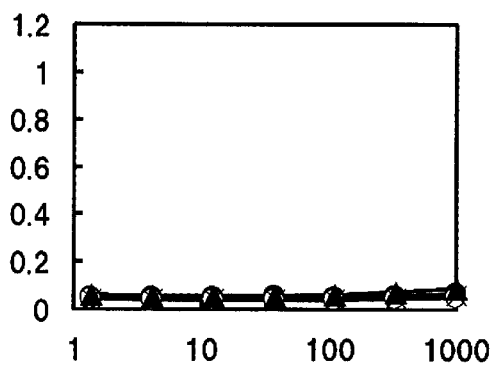
(b) MORAb-003DF
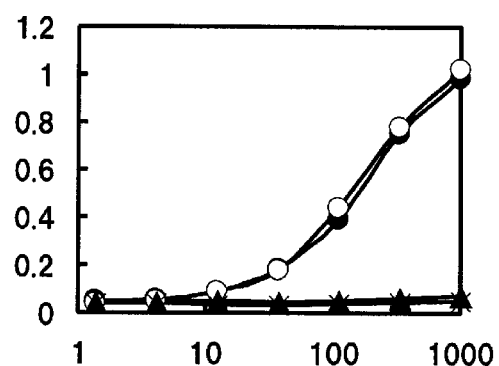
(c) ChRA15-7DF
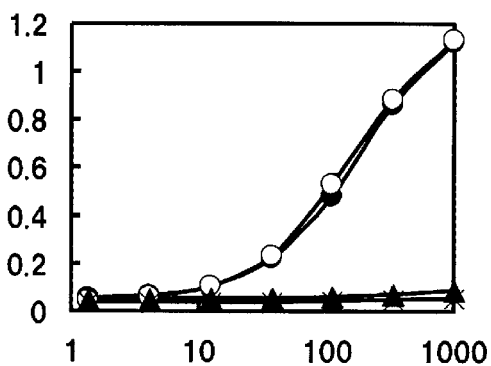
(d) HuRA15-7CTDF
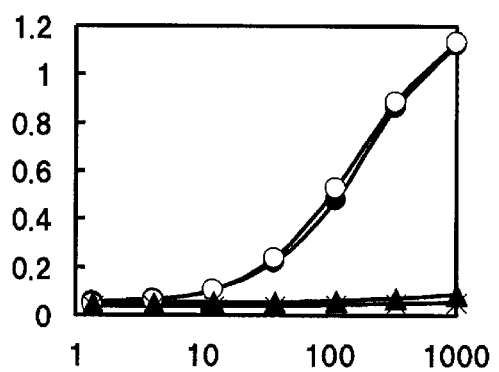

FIG. 5
(a) SKOV-3
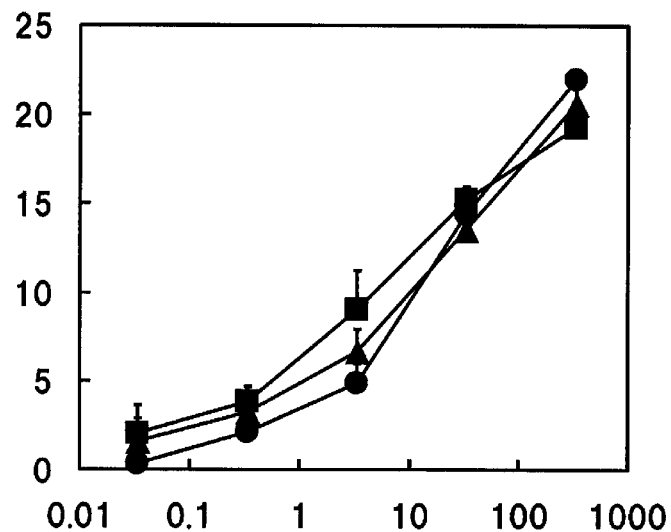
(b) OVCAR-3
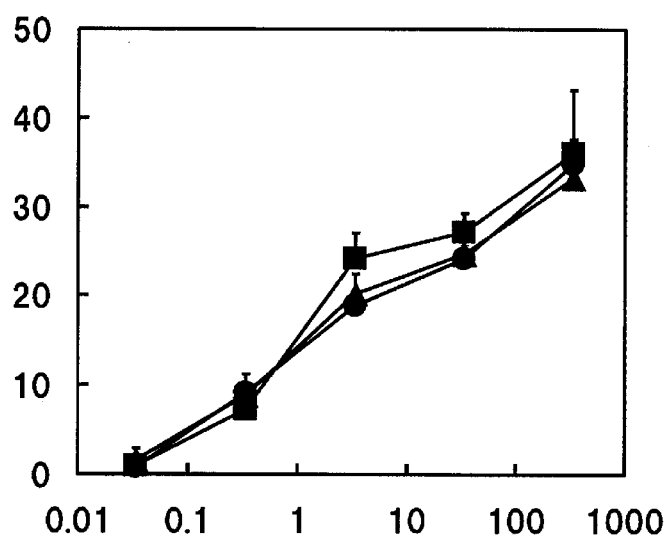

FIG. 6
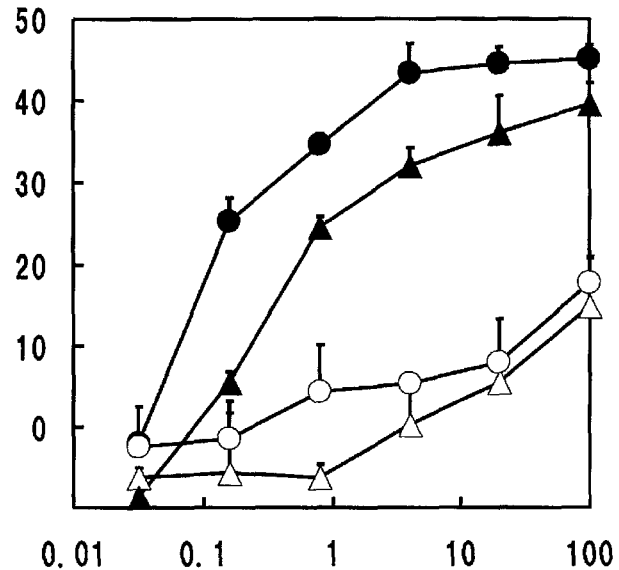
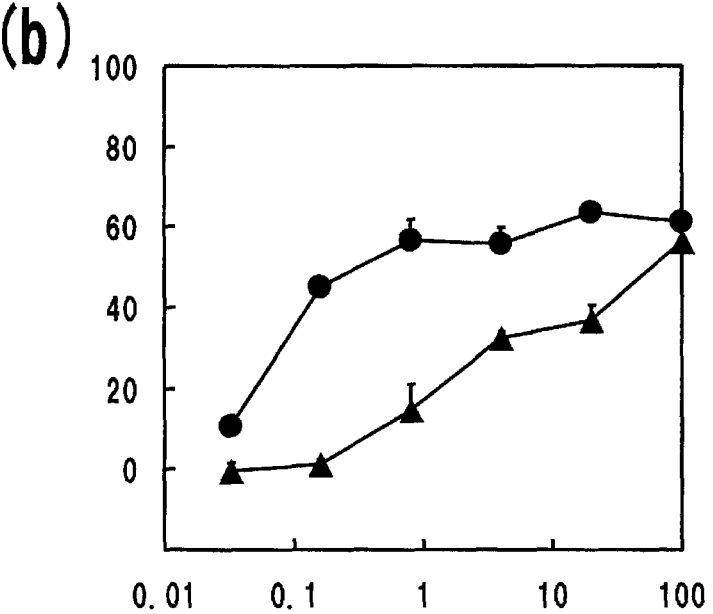

FIG. 7
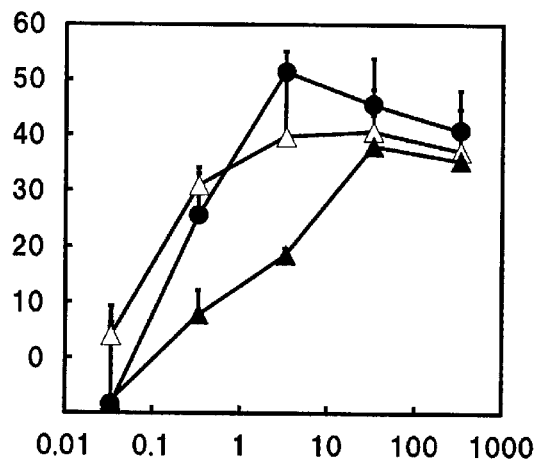
(a) IGR-OV1
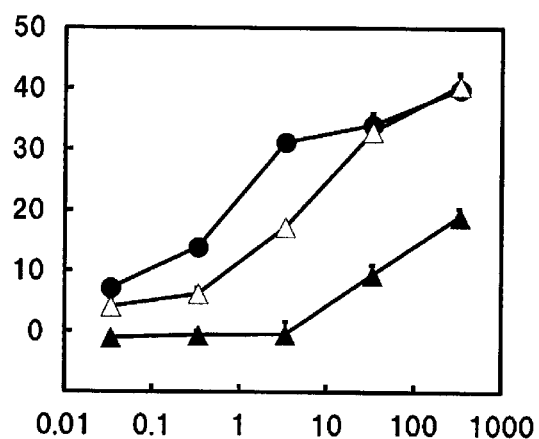
(b) SKOV-3
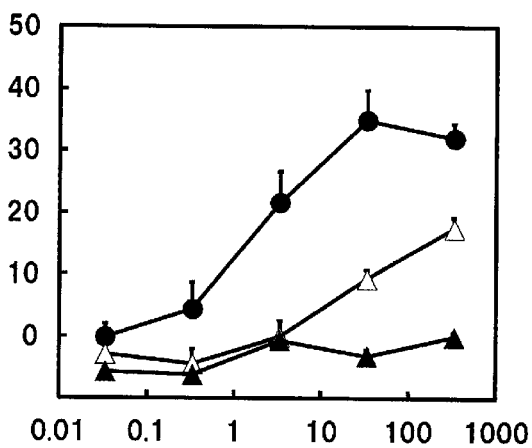
(c) OVCAR-3

```
                       SEQUENCE LISTING

<160> NUMBER OF SEQ ID NOS: 102

<210> SEQ ID NO 1
<211> LENGTH: 257
<212> TYPE: PRT
<213> ORGANISM: Homo sapiens

<400> SEQUENCE: 1

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
```

```
                115                 120                 125
Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 2
<211> LENGTH: 41
<212> TYPE: DNA
<213> ORGANISM: Artificial
<220> FEATURE:
<223> OTHER INFORMATION: FOLR1-F

<400> SEQUENCE: 2
caagaattca ttaaacgaca aggacagaca tggctcagcg g                41

<210> SEQ ID NO 3
<211> LENGTH: 27
<212> TYPE: DNA
<213> ORGANISM: Artificial
<220> FEATURE:
<223> OTHER INFORMATION: FOLR1-R

<400> SEQUENCE: 3
ccggtacctc agctgagcag ccacagc                                27

<210> SEQ ID NO 4
<211> LENGTH: 22
<212> TYPE: DNA
<213> ORGANISM: Artificial
<220> FEATURE:
<223> OTHER INFORMATION: CyFOLR1-F

<400> SEQUENCE: 4
atggctcagc ggatgacaac ac                                    22

<210> SEQ ID NO 5
<211> LENGTH: 22
<212> TYPE: DNA
<213> ORGANISM: Artificial
<220> FEATURE:
<223> OTHER INFORMATION: CyFOLR1-R

<400> SEQUENCE: 5
tcagcttagc agccagagca gc                                    22

<210> SEQ ID NO 6
<211> LENGTH: 774

```
<212> TYPE: DNA
<213> ORGANISM: Macaca fascicularis

<400> SEQUENCE: 6
atggctcagc ggatgacaac acagctgctg ctccttctag tgtgggtggc tgtagtaggg     60
gaggctcaga caaggactgc acgggccagg actgaacttc tcaatgtctg catgaacgcc    120
aagcaccaca aggaaaagcc aggcccggag acaagttgc atgagcagtg tcgtccctgg     180
aagaagaatg cctgctgttc taccaacacc agccaggaag cccataagga tgtttcctac    240
ctatatagat tcaactggaa ccactgtgga gagatggcac ctgcctgcaa acggcatttc    300
atccaggaca cctgcctcta cgagtgctcc cccaacttgg ggccctggat ccagcaggtg    360
gatcagagct ggcgcaaaga gcgggtgctg aacgtgcccc tgtgcaaaga ggactgtgag    420
caatggtggg aagactgtcg cacctcctac acctgcaaga gcaactggca caaaggctgg    480
aactggaccct cagggtttaa caagtgccca gtgggagctg cctgccaacc tttccatttc    540
tacttcccca cacccactgt tctgtgcaat gaaatctgga cttactccta caaggtcagc    600
aactacagcc gagggagtgg ccgctgcatc cagatgtggt tcgacccagc ccagggcaac    660
cccaatgagg aggtggcgag gttctatgct gcagccatga gtggggctgg gccctgggcg    720
gcctggcctc tcctacttag cctggcccta acgctgctct ggctgctaag ctga           774

<210> SEQ ID NO 7
<211> LENGTH: 257
<212> TYPE: PRT
<213> ORGANISM: Macaca fascicularis

<400> SEQUENCE: 7

Met Ala Gln Arg Met Thr Thr Gln Leu Leu Leu Leu Val Trp Val
1               5                   10                  15

Ala Val Val Gly Glu Ala Gln Thr Arg Thr Ala Arg Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Lys Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Pro Val Gly Ala Ala Cys Gln
                165                 170                 175

Pro Phe His Phe Tyr Phe Pro Thr Pro Thr Val Leu Cys Asn Glu Ile
            180                 185                 190

Trp Thr Tyr Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
```

Val Ala Arg Phe Tyr Ala Ala Ala Met Ser Gly Ala Gly Pro Trp Ala
225                 230                 235                 240

Ala Trp Pro Leu Leu Leu Ser Leu Ala Leu Thr Leu Leu Trp Leu Leu
            245                 250                 255

Ser

<210> SEQ ID NO 8
<211> LENGTH: 41
<212> TYPE: DNA
<213> ORGANISM: Artificial
<220> FEATURE:
<223> OTHER INFORMATION: FOLR1-Fc-F

<400> SEQUENCE: 8
caagaattca ttaaacgaca aggacagaca tggctcagcg g                    41

<210> SEQ ID NO 9
<211> LENGTH: 103
<212> TYPE: DNA
<213> ORGANISM: Artificial
<220> FEATURE:
<223> OTHER INFORMATION: FOLR1-Fc-R

<400> SEQUENCE: 9
catgactgac ggtcccccca ggagttcagg tgctgggcac ggtgggcatg tgtgagtttt    60
gtcacaagat ttgggctcca tggctgcagc atagaacctc gcc                     103

<210> SEQ ID NO 10
<211> LENGTH: 54
<212> TYPE: DNA
<213> ORGANISM: Artificial
<220> FEATURE:
<223> OTHER INFORMATION: FOLR2-Fc-F

<400> SEQUENCE: 10
catgaattca ttaaacgaca aggacagaca tggtctggaa atggatgcca cttc          54

<210> SEQ ID NO 11
<211> LENGTH: 98
<212> TYPE: DNA
<213> ORGANISM: Artificial
<220> FEATURE:
<223> OTHER INFORMATION: FOLR2-Fc-R

<400> SEQUENCE: 11
catgactgac ggtcccccca ggagttcagg tgctgggcac ggtgggcatg tgtgagtttt    60
gtcacaagat ttgggctcca tggctgcagc atagaacc                           98

<210> SEQ ID NO 12
<211> LENGTH: 50
<212> TYPE: DNA
<213> ORGANISM: Artificial
<220> FEATURE:
<223> OTHER INFORMATION: FOLR3-Fc-F

<400> SEQUENCE: 12
catgaattca ttaaacgaca aggacagaca tggcctggca gatgatgcag              50

<210> SEQ ID NO 13
<211> LENGTH: 101
<212> TYPE: DNA
<213> ORGANISM: Artificial

<220> FEATURE:
<223> OTHER INFORMATION: FOLR3-Fc-R

<400> SEQUENCE: 13

```
catgactgac ggtcccccca ggagttcagg tgctgggcac ggtgggcatg tgtgagtttt    60
gtcacaagat ttgggctcgg aatcaataat cccacgagac g                       101
```

<210> SEQ ID NO 14
<211> LENGTH: 41
<212> TYPE: DNA
<213> ORGANISM: Artificial
<220> FEATURE:
<223> OTHER INFORMATION: CyFOLR1-Fc-F

<400> SEQUENCE: 14

```
catgaattca ttaaacgaca aggacagaca tggctcagcg g                        41
```

<210> SEQ ID NO 15
<211> LENGTH: 102
<212> TYPE: DNA
<213> ORGANISM: Artificial
<220> FEATURE:
<223> OTHER INFORMATION: CyFOLR1-Fc-R

<400> SEQUENCE: 15

```
catgactgac ggtcccccca ggagttcagg tgctgggcac ggtgggcatg tgtgagtttt    60
gtcacaagat ttgggctcca tggctgcagc atagaacctc gc                      102
```

<210> SEQ ID NO 16
<211> LENGTH: 41
<212> TYPE: DNA
<213> ORGANISM: Artificial
<220> FEATURE:
<223> OTHER INFORMATION: FOLR1-mH-F

<400> SEQUENCE: 16

```
caagaattca ttaaacgaca aggacagaca tggctcagcg g                        41
```

<210> SEQ ID NO 17
<211> LENGTH: 121
<212> TYPE: DNA
<213> ORGANISM: Artificial
<220> FEATURE:
<223> OTHER INFORMATION: FOLR1-mH-R

<400> SEQUENCE: 17

```
catactagtt caatggtgat ggtgatgatg accggtatgc atattcagat cctcttctga    60
gatgagtttt tgttcgaagg gccctctaga ctcgagcatg gctgcagcat agaacctcgc   120
c                                                                  121
```

<210> SEQ ID NO 18
<211> LENGTH: 24
<212> TYPE: DNA
<213> ORGANISM: Artificial
<220> FEATURE:
<223> OTHER INFORMATION: RatIgG1H-A

<400> SEQUENCE: 18

```
cgctggacag ggctccagag ttcc                                           24
```

<210> SEQ ID NO 19
<211> LENGTH: 27
<212> TYPE: DNA
```

<213> ORGANISM: Artificial
<220> FEATURE:
<223> OTHER INFORMATION: RatIgG1H-B

<400> SEQUENCE: 19
gcaatcacct ccacagtttc tgggcac        27

<210> SEQ ID NO 20
<211> LENGTH: 31
<212> TYPE: DNA
<213> ORGANISM: Artificial
<220> FEATURE:
<223> OTHER INFORMATION: Ratk-A

<400> SEQUENCE: 20
gactgaggca cctccagttg ctaactgttc c        31

<210> SEQ ID NO 21
<211> LENGTH: 29
<212> TYPE: DNA
<213> ORGANISM: Artificial
<220> FEATURE:
<223> OTHER INFORMATION: Ratk-B

<400> SEQUENCE: 21
cctgttgaag ctcttgacga cgggtgagg        29

<210> SEQ ID NO 22
<211> LENGTH: 429
<212> TYPE: DNA
<213> ORGANISM: Artificial
<220> FEATURE:
<223> OTHER INFORMATION: RA15-7VH_DNA

<400> SEQUENCE: 22
atgaagttgt ggctgaactg gattttcctt ttaacacttt taaatggtat ccagtgtgag        60
gtgaagttgt tggaatctgg aggaggtttg gtacagccgg ggggttctat gagactctcc       120
tgtgcagctt ctggattcac cttcactgat ttctacatga actggatccg ccagcctgca       180
gggaaggcac tgagtggttt ggttttatt agaaacaaag ctaatggtta cacaacagag       240
ttcaatccgt ctgtgaaggg gcggttcgcc atctccagag ataatacccca aaacatgctc      300 tatcttcaaa tgaacaccct aagagctgag acactgccaa cttactactg tgcaagatgc      360
ctctatggat atgcctatta ctatgttatg gatgcctggg gtcaaggaac ttcagtcact      420
gtctcctca                                                               429

<210> SEQ ID NO 23
<211> LENGTH: 143
<212> TYPE: PRT
<213> ORGANISM: Artificial
<220> FEATURE:
<223> OTHER INFORMATION: RA15-7VH_AA

<400> SEQUENCE: 23

Met Lys Leu Trp Leu Asn Trp Ile Phe Leu Leu Thr Leu Leu Asn Gly
1               5                   10                  15

Ile Gln Cys Glu Val Lys Leu Leu Glu Ser Gly Gly Gly Leu Val Gln
            20                  25                  30

Pro Gly Gly Ser Met Arg Leu Ser Cys Ala Ala Ser Gly Phe Thr Phe
        35                  40                  45

Thr Asp Phe Tyr Met Asn Trp Ile Arg Gln Pro Ala Gly Lys Ala Pro
    50                  55                  60

```
Glu Trp Leu Gly Phe Ile Arg Asn Lys Ala Asn Gly Tyr Thr Thr Glu
 65                  70                  75                  80

Phe Asn Pro Ser Val Lys Gly Arg Phe Ala Ile Ser Arg Asp Asn Thr
             85                  90                  95

Gln Asn Met Leu Tyr Leu Gln Met Asn Thr Leu Arg Ala Glu Asp Thr
        100                 105                 110

Ala Thr Tyr Tyr Cys Ala Arg Cys Leu Tyr Gly Tyr Ala Tyr Tyr Tyr
        115                 120                 125

Val Met Asp Ala Trp Gly Gln Gly Thr Ser Val Thr Val Ser Ser
130                 135                 140

<210> SEQ ID NO 24
<211> LENGTH: 381
<212> TYPE: DNA
<213> ORGANISM: Artificial
<220> FEATURE:
<223> OTHER INFORMATION: RA15-7VL_DNA

<400> SEQUENCE: 24
atgggtgtcc ccactcagct cctggggttg atgctactgt ggattacaga tgccatatgt      60
gacatccaga tgacacagtc tccagcttcc ctgtctgcat ctctgggaga aactgtcacc     120
atcgaatgtc gaacaagtga agacattttc cgtaatttag cgtggtatca gcagagacca     180
gggaactctc ctcagctcct gatctatgat acaaataggt tggcagatgg ggtcccatca     240
cggttcagtg gcagtggttc tggcacacag tattctctaa agataaatag tctgcaatct     300
gaagatgtcg caggttattt ctgtcaacaa tatgacaatt atccgctcac gttcggttct     360
gggaccaagc tggagatcaa a                                                381

<210> SEQ ID NO 25
<211> LENGTH: 127
<212> TYPE: PRT
<213> ORGANISM: Artificial
<220> FEATURE:
<223> OTHER INFORMATION: RA15-7VL_AA

<400> SEQUENCE: 25

Met Gly Val Pro Thr Gln Leu Leu Gly Leu Met Leu Leu Trp Ile Thr
 1               5                  10                  15

Asp Ala Ile Cys Asp Ile Gln Met Thr Gln Ser Pro Ala Ser Leu Ser
            20                  25                  30

Ala Ser Leu Gly Glu Thr Val Thr Ile Glu Cys Arg Thr Ser Glu Asp
        35                  40                  45

Ile Phe Arg Asn Leu Ala Trp Tyr Gln Gln Arg Pro Gly Asn Ser Pro
    50                  55                  60

Gln Leu Leu Ile Tyr Asp Thr Asn Arg Leu Ala Asp Gly Val Pro Ser
 65                  70                  75                  80

Arg Phe Ser Gly Ser Gly Ser Gly Thr Gln Tyr Ser Leu Lys Ile Asn
             85                  90                  95

Ser Leu Gln Ser Glu Asp Val Ala Gly Tyr Phe Cys Gln Gln Tyr Asp
        100                 105                 110

Asn Tyr Pro Leu Thr Phe Gly Ser Gly Thr Lys Leu Glu Ile Lys
        115                 120                 125

<210> SEQ ID NO 26
<211> LENGTH: 372
<212> TYPE: DNA
<213> ORGANISM: Artificial
```

<220> FEATURE:
<223> OTHER INFORMATION: nonS_RA15-7VH_DNA

<400> SEQUENCE: 26

| | | | | | |
|---|---|---|---|---|---|
| gaggtgaagt | tgttggaatc | tggaggaggt | ttggtacagc | cggggggttc | tatgagactc | 60 |
| tcctgtgcag | cttctggatt | caccttcact | gatttctaca | tgaactggat | ccgccagcct | 120 |
| gcagggaagg | cacctgagtg | gttgggtttt | attagaaaca | aagctaatgg | ttacacaaca | 180 |
| gagttcaatc | cgtctgtgaa | ggggcggttc | gccatctcca | gagataatac | ccaaaacatg | 240 |
| ctctatcttc | aaatgaacac | cctaagagct | gaggacactg | ccacttacta | ctgtgcaaga | 300 |
| tgcctctatg | gatatgccta | ttactatgtt | atggatgcct | ggggtcaagg | aacttcagtc | 360 |
| actgtctcct | ca | | | | | 372 |

<210> SEQ ID NO 27
<211> LENGTH: 124
<212> TYPE: PRT
<213> ORGANISM: Artificial
<220> FEATURE:
<223> OTHER INFORMATION: nonS_RA15-7VH_AA

<400> SEQUENCE: 27

Glu Val Lys Leu Leu Glu Ser Gly Gly Gly Leu Val Gln Pro Gly Gly
1               5                   10                  15

Ser Met Arg Leu Ser Cys Ala Ala Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Ala Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Cys Leu Tyr Gly Tyr Ala Tyr Tyr Val Met Asp
            100                 105                 110

Ala Trp Gly Gln Gly Thr Ser Val Thr Val Ser Ser
        115                 120

<210> SEQ ID NO 28
<211> LENGTH: 321
<212> TYPE: DNA
<213> ORGANISM: Artificial
<220> FEATURE:
<223> OTHER INFORMATION: nonS_RA15-7VL_DNA

<400> SEQUENCE: 28

| | | | | | |
|---|---|---|---|---|---|
| gacatccaga | tgacacagtc | tccagcttcc | ctgtctgcat | ctctgggaga | aactgtcacc | 60 |
| atcgaatgtc | gaacaagtga | agacattttc | cgtaatttag | cgtggtatca | gcagagacca | 120 |
| gggaactctc | ctcagctcct | gatctatgat | acaaataggt | tggcagatgg | ggtcccatca | 180 |
| cggttcagtg | gcagtggttc | tggcacacag | tattctctaa | agataaatag | tctgcaatct | 240 |
| gaagatgtcg | caggttattt | ctgtcaacaa | tatgacaatt | atccgctcac | gttcggttct | 300 |
| gggaccaagc | tggagatcaa | a | | | | 321 |

<210> SEQ ID NO 29
<211> LENGTH: 107
<212> TYPE: PRT

<213> ORGANISM: Artificial
<220> FEATURE:
<223> OTHER INFORMATION: nonS_RA15-7VL_AA

<400> SEQUENCE: 29

Asp Ile Gln Met Thr Gln Ser Pro Ala Ser Leu Ser Ala Ser Leu Gly
1               5                   10                  15

Glu Thr Val Thr Ile Glu Cys Arg Thr Ser Glu Asp Ile Phe Arg Asn
            20                  25                  30

Leu Ala Trp Tyr Gln Gln Arg Pro Gly Asn Ser Pro Gln Leu Leu Ile
        35                  40                  45

Tyr Asp Thr Asn Arg Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Gly Tyr Phe Cys Gln Gln Tyr Asp Asn Tyr Pro Leu
                85                  90                  95

Thr Phe Gly Ser Gly Thr Lys Leu Glu Ile Lys
            100                 105

<210> SEQ ID NO 30
<211> LENGTH: 5
<212> TYPE: PRT
<213> ORGANISM: Artificial
<220> FEATURE:
<223> OTHER INFORMATION: RA15-7VHCDR1_AA

<400> SEQUENCE: 30

Asp Phe Tyr Met Asn
1               5

<210> SEQ ID NO 31
<211> LENGTH: 19
<212> TYPE: PRT
<213> ORGANISM: Artificial
<220> FEATURE:
<223> OTHER INFORMATION: RA15-7VHCDR2_AA

<400> SEQUENCE: 31

Phe Ile Arg Asn Lys Ala Asn Gly Tyr Thr Thr Glu Phe Asn Pro Ser
1               5                   10                  15

Val Lys Gly

<210> SEQ ID NO 32
<211> LENGTH: 13
<212> TYPE: PRT
<213> ORGANISM: Artificial
<220> FEATURE:
<223> OTHER INFORMATION: RA15-7VHCDR3_AA

<400> SEQUENCE: 32

Cys Leu Tyr Gly Tyr Ala Tyr Tyr Tyr Val Met Asp Ala
1               5                   10

<210> SEQ ID NO 33
<211> LENGTH: 11
<212> TYPE: PRT
<213> ORGANISM: Artificial
<220> FEATURE:
<223> OTHER INFORMATION: RA15-7VLCDR1_AA

<400> SEQUENCE: 33

Arg Thr Ser Glu Asp Ile Phe Arg Asn Leu Ala

<210> SEQ ID NO 34
<211> LENGTH: 7
<212> TYPE: PRT
<213> ORGANISM: Artificial
<220> FEATURE:
<223> OTHER INFORMATION: RA15-7VLCDR2_AA

<400> SEQUENCE: 34

Asp Thr Asn Arg Leu Ala Asp
1               5

<210> SEQ ID NO 35
<211> LENGTH: 9
<212> TYPE: PRT
<213> ORGANISM: Artificial
<220> FEATURE:
<223> OTHER INFORMATION: RA15-7VLCDR3_AA

<400> SEQUENCE: 35

Gln Gln Tyr Asp Asn Tyr Pro Leu Thr
1               5

<210> SEQ ID NO 36
<211> LENGTH: 109
<212> TYPE: DNA
<213> ORGANISM: Artificial
<220> FEATURE:
<223> OTHER INFORMATION: RA15-7-VLF

<400> SEQUENCE: 36
catgaattcg cctcctcaaa atgcattttc aagtgcagat tttcagcttc ctgcttattt      60
cggcctcagt cataatgtcc agaggagaca tccagatgac acagtctcc              109

<210> SEQ ID NO 37
<211> LENGTH: 32
<212> TYPE: DNA
<213> ORGANISM: Artificial
<220> FEATURE:
<223> OTHER INFORMATION: RA15-7-VLR

<400> SEQUENCE: 37
catcgtacgt ttgatctcca gcttggtccc ag                                   32

<210> SEQ ID NO 38
<211> LENGTH: 101
<212> TYPE: DNA
<213> ORGANISM: Artificial
<220> FEATURE:
<223> OTHER INFORMATION: RA15-7-VHF

<400> SEQUENCE: 38
catgcggccg cgacccctca ccatgagagt gcttatttta ttgtggctgt tcacagcctt      60
tcctggtatt cttagtgagg tgaagttgtt ggaatctgga g                        101

<210> SEQ ID NO 39
<211> LENGTH: 44
<212> TYPE: DNA
<213> ORGANISM: Artificial
<220> FEATURE:
<223> OTHER INFORMATION: RA15-7-VHR

<400> SEQUENCE: 39
catgggccct tggtggaggc tgaggagaca gtgactgaag ttcc                      44

<210> SEQ ID NO 40
<211> LENGTH: 993
<212> TYPE: DNA
<213> ORGANISM: Artificial
<220> FEATURE:
<223> OTHER INFORMATION: FcAcc_DNA

<400> SEQUENCE: 40

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggga     360
ccgtcagtct tcctcttccc cccaaaaccc aaggacaccc tcatgatctc ccggaccct     420
gaggtcacat gcgtggtggt ggacgtgagc cacgaagacc ccgaggtcca gttcaagtgg     480
tacgtggacg gcgtggaggt gcataatgcc aagacaaagc cgcggagga gcagttcaac     540
agcacgttcc gtgtggtcag cgtcctcacc gtcctgcacc aggactggct gaacggcaag     600
gagtacaagt gcaaggtctc caacaaagcc ctcccagccc ccatcgagaa aaccatctcc     660
aaaaccaaag gacagccccg agaaccacag gtgtacaccc tgcccccatc ccgggaggag     720
atgaccaaga accaggtcag cctgacctgc ctggtcaaag gcttctaccc cagcgacatc     780
gccgtggagt gggagagcag cgggcagccg gagaacaact acaagaccac gcctcccatg     840
ctggactccg acggctcctt cttcctctac agcaagctca ccgtggacaa gagcaggtgg     900
cagcagggga acatcttctc atgctccgtg atgcatgagg ctctgcacaa ccactacacg     960
cagaagagcc tctccctgtc tccgggtaaa tga                                  993
```

<210> SEQ ID NO 41
<211> LENGTH: 330
<212> TYPE: PRT
<213> ORGANISM: Artificial
<220> FEATURE:
<223> OTHER INFORMATION: FcAcc_AA

<400> SEQUENCE: 41

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

| Lys | Pro | Lys | Asp | Thr | Leu | Met | Ile | Ser | Arg | Thr | Pro | Glu | Val | Thr | Cys |
|---|---|---|---|---|---|---|---|---|---|---|---|---|---|---|---|
| | 130 | | | | 135 | | | | | 140 | | | | | |

| Val | Val | Val | Asp | Val | Ser | His | Glu | Asp | Pro | Val | Gln | Phe | Lys | Trp |
|---|---|---|---|---|---|---|---|---|---|---|---|---|---|---|
| 145 | | | | | 150 | | | | | 155 | | | | 160 |

| Tyr | Val | Asp | Gly | Val | Glu | Val | His | Asn | Ala | Lys | Thr | Lys | Pro | Arg | Glu |
|---|---|---|---|---|---|---|---|---|---|---|---|---|---|---|---|
| | | | | 165 | | | | | 170 | | | | | 175 | |

| Glu | Gln | Phe | Asn | Ser | Thr | Phe | Arg | Val | Val | Ser | Val | Leu | Thr | Val | Leu |
|---|---|---|---|---|---|---|---|---|---|---|---|---|---|---|---|
| | | | | 180 | | | | | 185 | | | | | 190 | |

| His | Gln | Asp | Trp | Leu | Asn | Gly | Lys | Glu | Tyr | Lys | Cys | Lys | Val | Ser | Asn |
|---|---|---|---|---|---|---|---|---|---|---|---|---|---|---|---|
| | | | 195 | | | | | 200 | | | | | 205 | | |

| Lys | Ala | Leu | Pro | Ala | Pro | Ile | Glu | Lys | Thr | Ile | Ser | Lys | Thr | Lys | Gly |
|---|---|---|---|---|---|---|---|---|---|---|---|---|---|---|---|
| | 210 | | | | | 215 | | | | | 220 | | | | |

| Gln | Pro | Arg | Glu | Pro | Gln | Val | Tyr | Thr | Leu | Pro | Pro | Ser | Arg | Glu | Glu |
|---|---|---|---|---|---|---|---|---|---|---|---|---|---|---|---|
| 225 | | | | | 230 | | | | | 235 | | | | | 240 |

| Met | Thr | Lys | Asn | Gln | Val | Ser | Leu | Thr | Cys | Leu | Val | Lys | Gly | Phe | Tyr |
|---|---|---|---|---|---|---|---|---|---|---|---|---|---|---|---|
| | | | | 245 | | | | | 250 | | | | | 255 | |

| Pro | Ser | Asp | Ile | Ala | Val | Glu | Trp | Glu | Ser | Ser | Gly | Gln | Pro | Glu | Asn |
|---|---|---|---|---|---|---|---|---|---|---|---|---|---|---|---|
| | | | 260 | | | | | 265 | | | | | 270 | | |

| Asn | Tyr | Lys | Thr | Thr | Pro | Pro | Met | Leu | Asp | Ser | Asp | Gly | Ser | Phe | Phe |
|---|---|---|---|---|---|---|---|---|---|---|---|---|---|---|---|
| | | 275 | | | | | 280 | | | | | 285 | | | |

| Leu | Tyr | Ser | Lys | Leu | Thr | Val | Asp | Lys | Ser | Arg | Trp | Gln | Gln | Gly | Asn |
|---|---|---|---|---|---|---|---|---|---|---|---|---|---|---|---|
| | 290 | | | | | 295 | | | | | 300 | | | | |

| Ile | Phe | Ser | Cys | Ser | Val | Met | His | Glu | Ala | Leu | His | Asn | His | Tyr | Thr |
|---|---|---|---|---|---|---|---|---|---|---|---|---|---|---|---|
| 305 | | | | | 310 | | | | | 315 | | | | | 320 |

| Gln | Lys | Ser | Leu | Ser | Leu | Ser | Pro | Gly | Lys |
|---|---|---|---|---|---|---|---|---|---|
| | | | | 325 | | | | | 330 |

<210> SEQ ID NO 42
<211> LENGTH: 780
<212> TYPE: DNA
<213> ORGANISM: Artificial
<220> FEATURE:
<223> OTHER INFORMATION: Rat1-FOLR1-mycHis_DNA

<400> SEQUENCE: 42

```
atggctcacc tgatggctgg gcagtggttg ctcctgctga tgtggatggc cgaatgtgcc      60
cagtccagag ctactcgggc caggactgag cttctcaatg tctgcatgaa cgccaagcac     120
cacaaggaaa agccaggccc cgaggacaag ttgcatgagc agtgtcgacc ctggaggaag     180
aatgcctgct gttctaccaa caccagccag gaagcccata aggatgtttc ctacctatat     240
agattcaact ggaaccactg tggagagatg gcacctgcct gcaaacggca tttcatccag     300
gacacctgcc tctacgagtg ctcccccaac ttggggccct ggatccagca ggtggatcag     360
agctggcgca agagcgggt actgaacgtg cccctgtgca agaggactg tgagcaatgg     420 tgggaagatt gtcgcaccct ctacacctgc aagagcaact ggcacaaggg ctggaactgg     480
acttcagggt taacaagtg cgcagtggga gctgcctgcc aacctttcca tttctacttc     540
cccacaccca ctgttctgtg caatgaaatc tggactcact cctacaaggt cagcaactac     600
agccgaggga gtggccgctg catccagatg tggttcgacc cagcccaggg caaccccaat     660
gaggaggtgg cgaggttcta tgctgcagcc atgctcgagt ctagagggcc cttcgaacaa     720
aaactcatct cagaagagga tctgaatatg cataccggtc atcatcacca tcaccattga     780
```

<210> SEQ ID NO 43
<211> LENGTH: 786
<212> TYPE: DNA

```
<213> ORGANISM: Artificial
<220> FEATURE:
<223> OTHER INFORMATION: Rat2-FOLR1-mycHis_DNA

<400> SEQUENCE: 43
atggctcagc ggatgacaac acagctgctg ctccttctag tgtgggtggc tgtagtaggg      60
gaggctcaga caaggattgc atgggccagg actgagcttc tcaatgtctg catgaacgcc     120
aagcaccaca aggaaaagcc aggccccgag gacaagttgc atgaccagtg cagcccctgg     180
aagacgaatg cctgctgttc taccaacacc agccaggaag cccataagga tgtttcctac     240
ctatatagat tcaactggaa ccactgtgga gagatggcac ctgcctgcaa acggcatttc     300
atccaggaca cctgcctcta cgagtgctcc cccaacttgg ggccctggat ccagcaggtg     360
gatcagagct ggcgcaaaga gcgggtactg aacgtgcccc tgtgcaaaga ggactgtgag     420
caatggtggg aagattgtcg cacctcctac acctgcaaga gcaactggca agggctgg       480
aactggactt cagggtttaa caagtgcgca gtgggagctg cctgccaacc tttccatttc     540
tacttcccca cacccactgt tctgtgcaat gaaatctgga ctcactccta caaggtcagc     600
aactacagcc gagggagtgg ccgctgcatc cagatgtggt tcgacccagc ccagggcaac     660
cccaatgagg aggtggcgag gttctatgct gcagccatgc tcgagtctag agggcccttc     720
gaacaaaaac tcatctcaga agaggatctg aatatgcata ccggtcatca tcaccatcac     780
cattga                                                                786

<210> SEQ ID NO 44
<211> LENGTH: 786
<212> TYPE: DNA
<213> ORGANISM: Artificial
<220> FEATURE:
<223> OTHER INFORMATION: Rat4-FOLR1-mycHis_DNA

<400> SEQUENCE: 44
atggctcagc ggatgacaac acagctgctg ctccttctag tgtgggtggc tgtagtaggg      60
gaggctcaga caaggattgc atgggccagg actgagcttc tcaatgtctg catgaacgcc     120
aagcaccaca aggaaaagcc aggccccgag gacaagttgc atgagcagtg tcgaccctgg     180
aggaagaatg cctgctgttc taccaacacc agccaggaag cccataagga tgtttcctac     240
ctatatagat tcaactggaa ccactgtgga actatgaccc cggagtgcaa acggcatttc     300
atccaggaca cctgcctcta cgagtgctcc cccaacttgg ggccctggat ccagcaggtg     360
gatcagagct ggcgcaaaga gcgggtactg aacgtgcccc tgtgcaaaga ggactgtgag     420
caatggtggg aagattgtcg cacctcctac acctgcaaga gcaactggca agggctgg       480
aactggactt cagggtttaa caagtgcgca gtgggagctg cctgccaacc tttccatttc     540
tacttcccca cacccactgt tctgtgcaat gaaatctgga ctcactccta caaggtcagc     600
aactacagcc gagggagtgg ccgctgcatc cagatgtggt tcgacccagc ccagggcaac     660
cccaatgagg aggtggcgag gttctatgct gcagccatgc tcgagtctag agggcccttc     720
gaacaaaaac tcatctcaga agaggatctg aatatgcata ccggtcatca tcaccatcac     780
cattga                                                                786

<210> SEQ ID NO 45
<211> LENGTH: 259
<212> TYPE: PRT
<213> ORGANISM: Artificial
<220> FEATURE:
<223> OTHER INFORMATION: Rat1-FOLR1-mycHis_AA
```

<400> SEQUENCE: 45

```
Met Ala His Leu Met Ala Gly Gln Trp Leu Leu Leu Met Trp Met
1               5                   10                  15

Ala Glu Cys Ala Gln Ser Arg Ala Thr Arg Ala Arg Thr Glu Leu Leu
            20                  25                  30

Asn Val Cys Met Asn Ala Lys His His Lys Glu Lys Pro Gly Pro Glu
            35                  40                  45

Asp Lys Leu His Glu Gln Cys Arg Pro Trp Arg Lys Asn Ala Cys Cys
        50                  55                  60

Ser Thr Asn Thr Ser Gln Glu Ala His Lys Asp Val Ser Tyr Leu Tyr
65                  70                  75                  80

Arg Phe Asn Trp Asn His Cys Gly Glu Met Ala Pro Ala Cys Lys Arg
                85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Val Leu
        115                 120                 125

Asn Val Pro Leu Cys Lys Glu Asp Cys Glu Gln Trp Trp Glu Asp Cys
130                 135                 140

Arg Thr Ser Tyr Thr Cys Lys Ser Asn Trp His Lys Gly Trp Asn Trp
145                 150                 155                 160

Thr Ser Gly Phe Asn Lys Cys Ala Val Gly Ala Ala Cys Gln Pro Phe
                165                 170                 175

His Phe Tyr Phe Pro Thr Pro Thr Val Leu Cys Asn Glu Ile Trp Thr
            180                 185                 190

His Ser Tyr Lys Val Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
    210                 215                 220

Arg Phe Tyr Ala Ala Ala Met Leu Glu Ser Arg Gly Pro Phe Glu Gln
225                 230                 235                 240

Lys Leu Ile Ser Glu Glu Asp Leu Asn Met His Thr Gly His His His
                245                 250                 255

His His His
```

<210> SEQ ID NO 46
<211> LENGTH: 261
<212> TYPE: PRT
<213> ORGANISM: Artificial
<220> FEATURE:
<223> OTHER INFORMATION: Rat2-FOLR1-mycHis_AA

<400> SEQUENCE: 46

```
Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
            35                  40                  45

Pro Glu Asp Lys Leu His Asp Gln Cys Ser Pro Trp Lys Thr Asn Ala
        50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
```

```
                    85                  90                  95
Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
            210                 215                 220

Val Ala Arg Phe Tyr Ala Ala Met Leu Glu Ser Arg Gly Pro Phe
225                 230                 235                 240

Glu Gln Lys Leu Ile Ser Glu Glu Asp Leu Asn Met His Thr Gly His
                245                 250                 255

His His His His His
            260

<210> SEQ ID NO 47
<211> LENGTH: 261
<212> TYPE: PRT
<213> ORGANISM: Artificial
<220> FEATURE:
<223> OTHER INFORMATION: Rat4-FOLR1-mycHis_AA

<400> SEQUENCE: 47

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Thr Met Thr Pro Glu Cys
                85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
```

```
            180                 185                 190
Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
            210                 215                 220

Val Ala Arg Phe Tyr Ala Ala Ala Met Leu Glu Ser Arg Gly Pro Phe
225                 230                 235                 240

Glu Gln Lys Leu Ile Ser Glu Glu Asp Leu Asn Met His Thr Gly His
                245                 250                 255

His His His His His
            260

<210> SEQ ID NO 48
<211> LENGTH: 372
<212> TYPE: DNA
<213> ORGANISM: Artificial
<220> FEATURE:
<223> OTHER INFORMATION: HV0

<400> SEQUENCE: 48
gaggtgcagt tggtggaatc tggtggcggt ttggtacagc cggggggttc tttgcgactc      60
tcctgtgcag cttctggctt caccttctct gatttctaca tgaactgggt ccgccaggct     120
ccagggaagg gtctcgagtg ggtgggtttt attcgaaaca aagctaatgg ttacacaaca     180
gagttcaatc cgtctgtgaa ggggcggttc accatctccc gagatgattc aagaacagc     240 ctctatcttc aaatgaactc cctgaagact gaggacactg ccgtgtacta ctgtgcacga     300
tgcctctatg gctatgccta ttactatgtt atggatgcct ggggtcaagg cactctggtc     360
actgtctcct ca                                                        372

<210> SEQ ID NO 49
<211> LENGTH: 372
<212> TYPE: DNA
<213> ORGANISM: Artificial
<220> FEATURE:
<223> OTHER INFORMATION: HV2

<400> SEQUENCE: 49
gaggtgcagt tggtggaatc tggtggcggt ttggtacagc cggggggttc tttgcgactc      60
tcctgtgcag cttctggctt caccttctct gatttctaca tgaactgggt ccgccagcct     120
ccagggaagg gtctcgagtg ggtgggtttt attcgaaaca aagctaatgg ttacacaaca     180
gagttcaatc cgtctgtgaa ggggcggttc accatctccc gagatgattc aagaacagc     240 ctctatcttc aaatgaactc cctgaagact gaggacactg ccacctacta ctgtgcacga     300
tgcctctatg gctatgccta ttactatgtt atggatgcct ggggtcaagg cactctggtc     360
actgtctcct ca                                                        372

<210> SEQ ID NO 50
<211> LENGTH: 372
<212> TYPE: DNA
<213> ORGANISM: Artificial
<220> FEATURE:
<223> OTHER INFORMATION: HV3

<400> SEQUENCE: 50
gaggtgcagt tggtggaatc tggtggcggt ttggtacagc cggggggttc tttgcgactc      60
tcctgtgcag cttctggctt caccttctct gatttctaca tgaactgggt ccgccaggct     120
```

```
gcagggaagg gtcctgagtg ggtgggtttt attcgaaaca aagctaatgg ttacacaaca    180
gagttcaatc cgtctgtgaa ggggcggttc accatctccc gagatgattc caagaacagc    240
ctctatcttc aaatgaactc cctgaagact gaggacactg ccacctacta ctgtgcacga    300
tgcctctatg gctatgccta ttactatgtt atggatgcct ggggtcaagg cactctggtc    360
actgtctcct ca                                                        372

<210> SEQ ID NO 51
<211> LENGTH: 372
<212> TYPE: DNA
<213> ORGANISM: Artificial
<220> FEATURE:
<223> OTHER INFORMATION: HV4

<400> SEQUENCE: 51
gaggtgcagt tggtggaatc tggtggcggt ttggtacagc cggggggttc tttgcgactc     60
tcctgtgcag cttctggctt caccttctct gatttctaca tgaactgggt ccgccagcct    120
gcagggaagg gtcctgagtg ggtgggtttt attcgaaaca aagctaatgg ttacacaaca    180
gagttcaatc cgtctgtgaa ggggcggttc accatctccc gagatgattc caagaacagc    240
ctctatcttc aaatgaactc cctgaagact gaggacactg ccacctacta ctgtgcacga    300
tgcctctatg gctatgccta ttactatgtt atggatgcct ggggtcaagg cactctggtc    360
actgtctcct ca                                                        372

<210> SEQ ID NO 52
<211> LENGTH: 372
<212> TYPE: DNA
<213> ORGANISM: Artificial
<220> FEATURE:
<223> OTHER INFORMATION: HV5

<400> SEQUENCE: 52
gaggtgcagt tggtggaatc tggtggcggt ttggtacagc cggggggttc tttgcgactc     60
tcctgtgcag cttctggctt caccttctct gatttctaca tgaactggat ccgccagcct    120
gcagggaagg gtcctgagtg gctgggtttt attcgaaaca aagctaatgg ttacacaaca    180
gagttcaatc cgtctgtgaa ggggcggttc accatctccc gagatgattc caagaacagc    240
ctctatcttc aaatgaactc cctgaagact gaggacactg ccgtgtacta ctgtgcacga    300
tgcctctatg gctatgccta ttactatgtt atggatgcct ggggtcaagg cactctggtc    360
actgtctcct ca                                                        372

<210> SEQ ID NO 53
<211> LENGTH: 372
<212> TYPE: DNA
<213> ORGANISM: Artificial
<220> FEATURE:
<223> OTHER INFORMATION: HV6

<400> SEQUENCE: 53
gaggtgcagt tggtggaatc tggtggcggt ttggtacagc cggggggttc tttgcgactc     60
tcctgtgcag cttctggctt caccttctct gatttctaca tgaactggat ccgccagcct    120
gcagggaagg gtcctgagtg gctgggtttt attcgaaaca aagctaatgg ttacacaaca    180
gagttcaatc cgtctgtgaa ggggcggttc accatctccc gagatgattc caagaacagc    240
ctctatcttc aaatgaactc cctgaagact gaggacactg ccacctacta ctgtgcacga    300
tgcctctatg gctatgccta ttactatgtt atggatgcct ggggtcaagg cactctggtc    360
```

```
actgtctcct ca                                                           372

<210> SEQ ID NO 54
<211> LENGTH: 372
<212> TYPE: DNA
<213> ORGANISM: Artificial
<220> FEATURE:
<223> OTHER INFORMATION: HV7

<400> SEQUENCE: 54
gaggtgcagt tggtggaatc tggtggcggt ttggtacagc cggggggttc tttgcgactc        60
tcctgtgcag cttctggctt caccttcact gatttctaca tgaactgggt ccgccagcct       120
ccagggaagg cccctgagtg gctgggtttt attcgaaaca aagctaatgg ttacacaaca       180
gagttcaatc cgtctgtgaa ggggcggttc accatctccc gagataattc caagaacagc       240
ctctatcttc aaatgaactc cctgaagact gaggacactg ccacctacta ctgtgcacga       300
tgcctctatg gctatgccta ttactatgtt atggatgcct ggggtcaagg cactctggtc       360
actgtctcct ca                                                           372

<210> SEQ ID NO 55
<211> LENGTH: 372
<212> TYPE: DNA
<213> ORGANISM: Artificial
<220> FEATURE:
<223> OTHER INFORMATION: HV8

<400> SEQUENCE: 55
gaggtgcagt tggtggaatc tggtggcggt ttggtacagc cggggggttc tttgcgactc        60
tcctgtgcag cttctggctt caccttctct gatttctaca tgaactggat ccgccagcct       120
gcagggaagg cccctgagtg gctgggtttt attcgaaaca aagctaatgg ttacacaaca       180
gagttcaatc cgtctgtgaa ggggcggttc accatctccc gagataattc caagaacagc       240
ctctatcttc aaatgaactc cctgaagact gaggacactg ccacctacta ctgtgcacga       300
tgcctctatg gctatgccta ttactatgtt atggatgcct ggggtcaagg cactctggtc       360
actgtctcct ca                                                           372

<210> SEQ ID NO 56
<211> LENGTH: 372
<212> TYPE: DNA
<213> ORGANISM: Artificial
<220> FEATURE:
<223> OTHER INFORMATION: HV10

<400> SEQUENCE: 56
gaggtgcagt tggtggaatc tggtggcggt ttggtacagc cggggggttc tatgcgactc        60
tcctgtgcag cttctggctt caccttcact gatttctaca tgaactggat ccgccagcct       120
gcagggaagg cccctgagtg gctgggtttt attcgaaaca aagctaatgg ttacacaaca       180
gagttcaatc cgtctgtgaa ggggcggttc accatctccc gagataattc caagaacagc       240
ctctatcttc aaatgaactc cctgaagact gaggacactg ccacctacta ctgtgcacga       300
tgcctctatg gctatgccta ttactatgtt atggatgcct ggggtcaagg cactctggtc       360
actgtctcct ca                                                           372

<210> SEQ ID NO 57
<211> LENGTH: 321
<212> TYPE: DNA
```

<213> ORGANISM: Artificial
<220> FEATURE:
<223> OTHER INFORMATION: LV0

<400> SEQUENCE: 57

| | | | | | |
|---|---|---|---|---|---|
| gacatccaga | tgacacagtc | tccatcttcc | ctgtctgcat | ctgtgggaga | tcgcgtcacc | 60 |
| atcacctgtc | gaacaagtga | agacattttc | cgtaatttag | cgtggtatca | gcagaagcca | 120 |
| gggaaggctc | ctaagctcct | gatctatgat | acaaataggt | tggcagatgg | ggtcccatca | 180 |
| cggttcagtg | gcagtggttc | tggcacagac | ttcactctaa | ccatatccag | tctgcaacct | 240 |
| gaagatttcg | caacctatta | ctgtcaacaa | tatgacaatt | atccgctcac | gttcggtcag | 300 |
| gggaccaagc | tggagatcaa | a | | | | 321 |

<210> SEQ ID NO 58
<211> LENGTH: 321
<212> TYPE: DNA
<213> ORGANISM: Artificial
<220> FEATURE:
<223> OTHER INFORMATION: LV2

<400> SEQUENCE: 58

| | | | | | |
|---|---|---|---|---|---|
| gacatccaga | tgacacagtc | tccatcttcc | ctgtctgcat | ctgtgggaga | tcgcgtcacc | 60 |
| atcacctgtc | gaacaagtga | agacattttc | cgtaatttag | cgtggtatca | gcagaagcca | 120 |
| gggaaggctc | ctcagctcct | gatctatgat | acaaataggt | tggcagatgg | ggtcccatca | 180 |
| cggttcagtg | gcagtggttc | tggcacagac | tacactctaa | ccatatccag | tctgcaacct | 240 |
| gaagatttcg | caacctatta | ctgtcaacaa | tatgacaatt | atccgctcac | gttcggtcag | 300 |
| gggaccaagc | tggagatcaa | a | | | | 321 |

<210> SEQ ID NO 59
<211> LENGTH: 321
<212> TYPE: DNA
<213> ORGANISM: Artificial
<220> FEATURE:
<223> OTHER INFORMATION: LV3

<400> SEQUENCE: 59

| | | | | | |
|---|---|---|---|---|---|
| gacatccaga | tgacacagtc | tccatcttcc | ctgtctgcat | ctctcggaga | tcgcgtcacc | 60 |
| atcacctgtc | gaacaagtga | agacattttc | cgtaatttag | cgtggtatca | gcagaagcca | 120 |
| gggaaggctc | ctaagctcct | gatctatgat | acaaataggt | tggcagatgg | ggtcccatca | 180 |
| cggttcagtg | gcagtggttc | tggcacagac | tacactctaa | ccatatccag | tctgcaacct | 240 |
| gaagatttcg | caacctattt | ctgtcaacaa | tatgacaatt | atccgctcac | gttcggtcag | 300 |
| gggaccaagc | tggagatcaa | a | | | | 321 |

<210> SEQ ID NO 60
<211> LENGTH: 321
<212> TYPE: DNA
<213> ORGANISM: Artificial
<220> FEATURE:
<223> OTHER INFORMATION: LV4

<400> SEQUENCE: 60

| | | | | | |
|---|---|---|---|---|---|
| gacatccaga | tgacacagtc | tccatcttcc | ctgtctgcat | ctctcggaga | tcgcgtcacc | 60 |
| atcacctgtc | gaacaagtga | agacattttc | cgtaatttag | cgtggtatca | gcagaagcca | 120 |
| gggaaggctc | ctcagctcct | gatctatgat | acaaataggt | tggcagatgg | ggtcccatca | 180 |
| cggttcagtg | gcagtggttc | tggcacagac | tacactctaa | ccatatccag | tctgcaacct | 240 |

```
gaagatttcg caacctattt ctgtcaacaa tatgacaatt atccgctcac gttcgguag      300 gggaccaagc tggagatcaa a                                                321
```

<210> SEQ ID NO 61
<211> LENGTH: 321
<212> TYPE: DNA
<213> ORGANISM: Artificial
<220> FEATURE:
<223> OTHER INFORMATION: LV6

<400> SEQUENCE: 61

```
gacatccaga tgacacagtc tccatcttcc ctgtctgcat ctctcggaga tcgcgtcacc       60
atcacctgtc gaacaagtga agacattttc cgtaatttag cgtggtatca gcagaagcca      120 ggaagtccc ctcagctcct gatctatgat acaaataggt tggcagatgg ggtcccatca       180
cggttcagtg gcagtggttc tggcacagac tacactctaa ccatatccag tctgcaacct      240
gaagatttcg caggctattt ctgtcaacaa tatgacaatt atccgctcac gttcggucag      300
gggaccaagc tggagatcaa a                                                321
```

<210> SEQ ID NO 62
<211> LENGTH: 429
<212> TYPE: DNA
<213> ORGANISM: Artificial
<220> FEATURE:
<223> OTHER INFORMATION: HuRA15-7HV7_DNA

<400> SEQUENCE: 62

```
atgaacctcg ggctcagttt gatttcctt gccctcattt taaaaggtgt ccagtgtgag        60
gtgcagttgg tggaatctgg tggcggtttg gtacagccgg ggggttcttt gcgactctcc      120
tgtgcagctt ctggcttcac cttcactgat ttctacatga actgggtccg ccagcctcca      180 ggaaggccc ctgagtggct gggttttatt cgaaacaaag ctaatggtta cacaacagag       240
ttcaatccgt ctgtgaaggg gcggttcacc atctcccgag ataattccaa gaacagcctc      300
tatcttcaaa tgaactccct gaagactgag gacactgcca cctactactg tgcacgatgc      360
ctctatggct atgcctatta ctatgttatg gatgcctggg gtcaaggcac tctggtcact      420
gtctcctca                                                              429
```

<210> SEQ ID NO 63
<211> LENGTH: 372
<212> TYPE: DNA
<213> ORGANISM: Artificial
<220> FEATURE:
<223> OTHER INFORMATION: C101M_DNA

<400> SEQUENCE: 63

```
gaggtgcagt tggtggaatc tggtggcggt ttggtacagc cggggggttc tttgcgactc       60
tcctgtgcag cttctggctt caccttcact gatttctaca tgaactgggt ccgccagcct      120
ccagggaagg cccctgagtg gctgggtttt attcgaaaca agctaatgg ttacacaaca       180 gagttcaatc cgtctgtgaa ggggcggttc accatctccc gagataattc caagaacagc      240
ctctatcttc aaatgaactc cctgaagact gaggacactg ccacctacta ctgtgcacga      300
atgctctatg gctatgccta ttactatgtt atggatgcct ggggtcaagg cactctggtc      360
actgtctcct ca                                                          372
```

<210> SEQ ID NO 64

```
<211> LENGTH: 372
<212> TYPE: DNA
<213> ORGANISM: Artificial
<220> FEATURE:
<223> OTHER INFORMATION: C101G_DNA

<400> SEQUENCE: 64
gaggtgcagt tggtggaatc tggtggcggt ttggtacagc cggggggttc tttgcgactc      60
tcctgtgcag cttctggctt caccttcact gatttctaca tgaactgggt ccgccagcct    120
ccagggaagg cccctgagtg gctgggtttt attcgaaaca aagctaatgg ttacacaaca    180
gagttcaatc cgtctgtgaa ggggcggttc accatctccc gagataattc caagaacagc    240
ctctatcttc aaatgaactc cctgaagact gaggacactg ccacctacta ctgtgcacga    300
ggcctctatg gctatgccta ttactatgtt atggatgcct ggggtcaagg cactctggtc    360
actgtctcct ca                                                         372

<210> SEQ ID NO 65
<211> LENGTH: 372
<212> TYPE: DNA
<213> ORGANISM: Artificial
<220> FEATURE:
<223> OTHER INFORMATION: C101D_DNA

<400> SEQUENCE: 65
gaggtgcagt tggtggaatc tggtggcggt ttggtacagc cggggggttc tttgcgactc      60
tcctgtgcag cttctggctt caccttcact gatttctaca tgaactgggt ccgccagcct    120
ccagggaagg cccctgagtg gctgggtttt attcgaaaca aagctaatgg ttacacaaca    180
gagttcaatc cgtctgtgaa ggggcggttc accatctccc gagataattc caagaacagc    240
ctctatcttc aaatgaactc cctgaagact gaggacactg ccacctacta ctgtgcacga    300
gacctctatg gctatgccta ttactatgtt atggatgcct ggggtcaagg cactctggtc    360
actgtctcct ca                                                         372

<210> SEQ ID NO 66
<211> LENGTH: 372
<212> TYPE: DNA
<213> ORGANISM: Artificial
<220> FEATURE:
<223> OTHER INFORMATION: C101S_DNA

<400> SEQUENCE: 66
gaggtgcagt tggtggaatc tggtggcggt ttggtacagc cggggggttc tttgcgactc      60
tcctgtgcag cttctggctt caccttcact gatttctaca tgaactgggt ccgccagcct    120
ccagggaagg cccctgagtg gctgggtttt attcgaaaca aagctaatgg ttacacaaca    180
gagttcaatc cgtctgtgaa ggggcggttc accatctccc gagataattc caagaacagc    240
ctctatcttc aaatgaactc cctgaagact gaggacactg ccacctacta ctgtgcacga    300
tccctctatg gctatgccta ttactatgtt atggatgcct ggggtcaagg cactctggtc    360
actgtctcct ca                                                         372

<210> SEQ ID NO 67
<211> LENGTH: 372
<212> TYPE: DNA
<213> ORGANISM: Artificial
<220> FEATURE:
<223> OTHER INFORMATION: C101Y_DNA

<400> SEQUENCE: 67
```

```
gaggtgcagt tggtggaatc tgtggcggt ttggtacagc cgggggttc tttgcgactc      60 tcctgtgcag cttctggctt caccttcact gatttctaca tgaactgggt ccgccagcct   120
ccagggaagg cccctgagtg gctgggtttt attcgaaaca aagctaatgg ttacacaaca   180
gagttcaatc cgtctgtgaa ggggcggttc accatctccc gagataattc caagaacagc   240
ctctatcttc aaatgaactc cctgaagact gaggacactg ccacctacta ctgtgcacga   300
tacctctatg gctatgccta ttactatgtt atggatgcct ggggtcaagg cactctggtc   360
actgtctcct ca                                                       372
```

<210> SEQ ID NO 68
<211> LENGTH: 372
<212> TYPE: DNA
<213> ORGANISM: Artificial
<220> FEATURE:
<223> OTHER INFORMATION: C101A_DNA

<400> SEQUENCE: 68

```
gaggtgcagt tggtggaatc tgtggcggt ttggtacagc cgggggttc tttgcgactc      60 tcctgtgcag cttctggctt caccttcact gatttctaca tgaactgggt ccgccagcct   120
ccagggaagg cccctgagtg gctgggtttt attcgaaaca aagctaatgg ttacacaaca   180
gagttcaatc cgtctgtgaa ggggcggttc accatctccc gagataattc caagaacagc   240
ctctatcttc aaatgaactc cctgaagact gaggacactg ccacctacta ctgtgcacga   300
gccctctatg gctatgccta ttactatgtt atggatgcct ggggtcaagg cactctggtc   360
actgtctcct ca                                                       372
```

<210> SEQ ID NO 69
<211> LENGTH: 372
<212> TYPE: DNA
<213> ORGANISM: Artificial
<220> FEATURE:
<223> OTHER INFORMATION: C101I_DNA

<400> SEQUENCE: 69

```
gaggtgcagt tggtggaatc tgtggcggt ttggtacagc cgggggttc tttgcgactc      60 tcctgtgcag cttctggctt caccttcact gatttctaca tgaactgggt ccgccagcct   120
ccagggaagg cccctgagtg gctgggtttt attcgaaaca aagctaatgg ttacacaaca   180
gagttcaatc cgtctgtgaa ggggcggttc accatctccc gagataattc caagaacagc   240
ctctatcttc aaatgaactc cctgaagact gaggacactg ccacctacta ctgtgcacga   300
atcctctatg gctatgccta ttactatgtt atggatgcct ggggtcaagg cactctggtc   360
actgtctcct ca                                                       372
```

<210> SEQ ID NO 70
<211> LENGTH: 372
<212> TYPE: DNA
<213> ORGANISM: Artificial
<220> FEATURE:
<223> OTHER INFORMATION: C101V_DNA

<400> SEQUENCE: 70

```
gaggtgcagt tggtggaatc tgtggcggt ttggtacagc cgggggttc tttgcgactc      60 tcctgtgcag cttctggctt caccttcact gatttctaca tgaactgggt ccgccagcct   120
ccagggaagg cccctgagtg gctgggtttt attcgaaaca aagctaatgg ttacacaaca   180
```

-continued

```
gagttcaatc cgtctgtgaa ggggcggttc accatctccc gagataattc caagaacagc    240
ctctatcttc aaatgaactc cctgaagact gaggacactg ccacctacta ctgtgcacga    300
gtcctctatg gctatgccta ttactatgtt atggatgcct ggggtcaagg cactctggtc    360
actgtctcct ca                                                        372
```

<210> SEQ ID NO 71
<211> LENGTH: 372
<212> TYPE: DNA
<213> ORGANISM: Artificial
<220> FEATURE:
<223> OTHER INFORMATION: C101T_DNA

<400> SEQUENCE: 71

```
gaggtgcagt tggtggaatc tggtggcggt ttggtacagc cggggggttc tttgcgactc    60
tcctgtgcag cttctggctt caccttcact gatttctaca tgaactgggt ccgccagcct    120
ccagggaagg cccctgagtg gctgggtttt attcgaaaca agctaatgg ttacacaaca    180 gagttcaatc cgtctgtgaa ggggcggttc accatctccc gagataattc caagaacagc    240
ctctatcttc aaatgaactc cctgaagact gaggacactg ccacctacta ctgtgcacga    300
accctctatg gctatgccta ttactatgtt atggatgcct ggggtcaagg cactctggtc    360
actgtctcct ca                                                        372
```

<210> SEQ ID NO 72
<211> LENGTH: 372
<212> TYPE: DNA
<213> ORGANISM: Artificial
<220> FEATURE:
<223> OTHER INFORMATION: C101F_DNA

<400> SEQUENCE: 72

```
gaggtgcagt tggtggaatc tggtggcggt ttggtacagc cggggggttc tttgcgactc    60
tcctgtgcag cttctggctt caccttcact gatttctaca tgaactgggt ccgccagcct    120
ccagggaagg cccctgagtg gctgggtttt attcgaaaca agctaatgg ttacacaaca    180 gagttcaatc cgtctgtgaa ggggcggttc accatctccc gagataattc caagaacagc    240
ctctatcttc aaatgaactc cctgaagact gaggacactg ccacctacta ctgtgcacga    300
ttcctctatg gctatgccta ttactatgtt atggatgcct ggggtcaagg cactctggtc    360
actgtctcct ca                                                        372
```

<210> SEQ ID NO 73
<211> LENGTH: 372
<212> TYPE: DNA
<213> ORGANISM: Artificial
<220> FEATURE:
<223> OTHER INFORMATION: C101R_DNA

<400> SEQUENCE: 73

```
gaggtgcagt tggtggaatc tggtggcggt ttggtacagc cggggggttc tttgcgactc    60
tcctgtgcag cttctggctt caccttcact gatttctaca tgaactgggt ccgccagcct    120
ccagggaagg cccctgagtg gctgggtttt attcgaaaca agctaatgg ttacacaaca    180 gagttcaatc cgtctgtgaa ggggcggttc accatctccc gagataattc caagaacagc    240
ctctatcttc aaatgaactc cctgaagact gaggacactg ccacctacta ctgtgcacga    300
cgcctctatg gctatgccta ttactatgtt atggatgcct ggggtcaagg cactctggtc    360
actgtctcct ca                                                        372
```

<210> SEQ ID NO 74
<211> LENGTH: 372
<212> TYPE: DNA
<213> ORGANISM: Artificial
<220> FEATURE:
<223> OTHER INFORMATION: C101W_DNA

<400> SEQUENCE: 74

```
gaggtgcagt tggtggaatc tggtggcggt ttggtacagc cggggggttc tttgcgactc      60
tcctgtgcag cttctggctt caccttcact gatttctaca tgaactgggt ccgccagcct     120
ccagggaagg cccctgagtg gctgggtttt attcgaaaca agctaatgg ttacacaaca     180
gagttcaatc cgtctgtgaa ggggcggttc accatctccc gagataattc caagaacagc     240
ctctatcttc aaatgaactc cctgaagact gaggacactg ccacctacta ctgtgcacga     300
tggctctatg gctatgccta ttactatgtt atggatgcct ggggtcaagg cactctggtc     360
actgtctcct ca                                                         372
```

<210> SEQ ID NO 75
<211> LENGTH: 372
<212> TYPE: DNA
<213> ORGANISM: Artificial
<220> FEATURE:
<223> OTHER INFORMATION: C101P_DNA

<400> SEQUENCE: 75

```
gaggtgcagt tggtggaatc tggtggcggt ttggtacagc cggggggttc tttgcgactc      60
tcctgtgcag cttctggctt caccttcact gatttctaca tgaactgggt ccgccagcct     120
ccagggaagg cccctgagtg gctgggtttt attcgaaaca agctaatgg ttacacaaca     180
gagttcaatc cgtctgtgaa ggggcggttc accatctccc gagataattc caagaacagc     240
ctctatcttc aaatgaactc cctgaagact gaggacactg ccacctacta ctgtgcacga     300
cctctctatg gctatgccta ttactatgtt atggatgcct ggggtcaagg cactctggtc     360
actgtctcct ca                                                         372
```

<210> SEQ ID NO 76
<211> LENGTH: 372
<212> TYPE: DNA
<213> ORGANISM: Artificial
<220> FEATURE:
<223> OTHER INFORMATION: C101Q_DNA

<400> SEQUENCE: 76

```
gaggtgcagt tggtggaatc tggtggcggt ttggtacagc cggggggttc tttgcgactc      60
tcctgtgcag cttctggctt caccttcact gatttctaca tgaactgggt ccgccagcct     120
ccagggaagg cccctgagtg gctgggtttt attcgaaaca agctaatgg ttacacaaca     180
gagttcaatc cgtctgtgaa ggggcggttc accatctccc gagataattc caagaacagc     240
ctctatcttc aaatgaactc cctgaagact gaggacactg ccacctacta ctgtgcacga     300
cagctctatg gctatgccta ttactatgtt atggatgcct ggggtcaagg cactctggtc     360
actgtctcct ca                                                         372
```

<210> SEQ ID NO 77
<211> LENGTH: 124
<212> TYPE: PRT
<213> ORGANISM: Artificial
<220> FEATURE:

<223> OTHER INFORMATION: C101M_AA

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Met Leu Tyr Gly Tyr Ala Tyr Tyr Val Met Asp
            100                 105                 110

Ala Trp Gly Gln Gly Thr Leu Val Thr Val Ser Ser
        115                 120

<210> SEQ ID NO 78
<211> LENGTH: 124
<212> TYPE: PRT
<213> ORGANISM: Artificial
<220> FEATURE:
<223> OTHER INFORMATION: C101G_AA

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Gly Leu Tyr Gly Tyr Ala Tyr Tyr Val Met Asp
            100                 105                 110

Ala Trp Gly Gln Gly Thr Leu Val Thr Val Ser Ser
        115                 120

<210> SEQ ID NO 79
<211> LENGTH: 124
<212> TYPE: PRT
<213> ORGANISM: Artificial
<220> FEATURE:
<223> OTHER INFORMATION: C101D_AA

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu

```
                35                  40                  45
Gly Phe Ile Arg Asn Lys Ala Asn Gly Tyr Thr Thr Glu Phe Asn Pro
        50                  55                  60
Ser Val Lys Gly Arg Phe Thr Ile Ser Arg Asp Asn Ser Lys Asn Ser
 65                 70                  75                  80
Leu Tyr Leu Gln Met Asn Ser Leu Lys Thr Glu Asp Thr Ala Thr Tyr
                85                  90                  95
Tyr Cys Ala Arg Asp Leu Tyr Gly Tyr Ala Tyr Tyr Val Met Asp
                100                 105                 110
Ala Trp Gly Gln Gly Thr Leu Val Thr Val Ser Ser
            115                 120

<210> SEQ ID NO 80
<211> LENGTH: 124
<212> TYPE: PRT
<213> ORGANISM: Artificial
<220> FEATURE:
<223> OTHER INFORMATION: C101S_AA

<400> SEQUENCE: 80

Glu Val Gln Leu Val Glu Ser Gly Gly Gly Leu Val Gln Pro Gly Gly
 1               5                   10                  15
Ser Leu Arg Leu Ser Cys Ala Ala Ser Gly Phe Thr Phe Thr Asp Phe
                20                  25                  30
Tyr Met Asn Trp Val Arg Gln Pro Pro Gly Lys Ala Pro Glu Trp Leu
                35                  40                  45
Gly Phe Ile Arg Asn Lys Ala Asn Gly Tyr Thr Thr Glu Phe Asn Pro
        50                  55                  60
Ser Val Lys Gly Arg Phe Thr Ile Ser Arg Asp Asn Ser Lys Asn Ser
 65                 70                  75                  80
Leu Tyr Leu Gln Met Asn Ser Leu Lys Thr Glu Asp Thr Ala Thr Tyr
                85                  90                  95
Tyr Cys Ala Arg Ser Leu Tyr Gly Tyr Ala Tyr Tyr Val Met Asp
                100                 105                 110
Ala Trp Gly Gln Gly Thr Leu Val Thr Val Ser Ser
            115                 120

<210> SEQ ID NO 81
<211> LENGTH: 124
<212> TYPE: PRT
<213> ORGANISM: Artificial
<220> FEATURE:
<223> OTHER INFORMATION: C101Y_AA

<400> SEQUENCE: 81

Glu Val Gln Leu Val Glu Ser Gly Gly Gly Leu Val Gln Pro Gly Gly
 1               5                   10                  15
Ser Leu Arg Leu Ser Cys Ala Ala Ser Gly Phe Thr Phe Thr Asp Phe
                20                  25                  30
Tyr Met Asn Trp Val Arg Gln Pro Pro Gly Lys Ala Pro Glu Trp Leu
                35                  40                  45
Gly Phe Ile Arg Asn Lys Ala Asn Gly Tyr Thr Thr Glu Phe Asn Pro
        50                  55                  60
Ser Val Lys Gly Arg Phe Thr Ile Ser Arg Asp Asn Ser Lys Asn Ser
 65                 70                  75                  80
Leu Tyr Leu Gln Met Asn Ser Leu Lys Thr Glu Asp Thr Ala Thr Tyr
                85                  90                  95
```

Tyr Cys Ala Arg Tyr Leu Tyr Gly Tyr Ala Tyr Tyr Val Met Asp
            100                 105                 110

Ala Trp Gly Gln Gly Thr Leu Val Thr Val Ser Ser
            115                 120

<210> SEQ ID NO 82
<211> LENGTH: 124
<212> TYPE: PRT
<213> ORGANISM: Artificial
<220> FEATURE:
<223> OTHER INFORMATION: C101A_AA

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Ala Leu Tyr Gly Tyr Ala Tyr Tyr Val Met Asp
            100                 105                 110

Ala Trp Gly Gln Gly Thr Leu Val Thr Val Ser Ser
            115                 120

<210> SEQ ID NO 83
<211> LENGTH: 124
<212> TYPE: PRT
<213> ORGANISM: Artificial
<220> FEATURE:
<223> OTHER INFORMATION: C101I_AA

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Ile Leu Tyr Gly Tyr Ala Tyr Tyr Val Met Asp
            100                 105                 110

Ala Trp Gly Gln Gly Thr Leu Val Thr Val Ser Ser
            115                 120

<210> SEQ ID NO 84
<211> LENGTH: 124
<212> TYPE: PRT
<213> ORGANISM: Artificial

```
<220> FEATURE:
<223> OTHER INFORMATION: C101V_AA

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Val Leu Tyr Gly Tyr Ala Tyr Tyr Val Met Asp
            100                 105                 110

Ala Trp Gly Gln Gly Thr Leu Val Thr Val Ser Ser
        115                 120

<210> SEQ ID NO 85
<211> LENGTH: 124
<212> TYPE: PRT
<213> ORGANISM: Artificial
<220> FEATURE:
<223> OTHER INFORMATION: C101T_AA

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Thr Leu Tyr Gly Tyr Ala Tyr Tyr Val Met Asp
            100                 105                 110

Ala Trp Gly Gln Gly Thr Leu Val Thr Val Ser Ser
        115                 120

<210> SEQ ID NO 86
<211> LENGTH: 124
<212> TYPE: PRT
<213> ORGANISM: Artificial
<220> FEATURE:
<223> OTHER INFORMATION: C101F_AA

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30
```

```
Tyr Met Asn Trp Val Arg Gln Pro Gly Lys Ala Pro Glu Trp Leu
            35                  40                  45

Gly Phe Ile Arg Asn Lys Ala Asn Gly Tyr Thr Thr Glu Phe Asn Pro
 50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Thr Tyr
                 85                  90                  95

Tyr Cys Ala Arg Phe Leu Tyr Gly Tyr Ala Tyr Tyr Val Met Asp
                100                 105                 110

Ala Trp Gly Gln Gly Thr Leu Val Thr Val Ser Ser
            115                 120
```

<210> SEQ ID NO 87
<211> LENGTH: 124
<212> TYPE: PRT
<213> ORGANISM: Artificial
<220> FEATURE:
<223> OTHER INFORMATION: C101R_AA

<400> SEQUENCE: 87

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Phe
             20                  25                  30

Tyr Met Asn Trp Val Arg Gln Pro Gly Lys Ala Pro Glu Trp Leu
            35                  40                  45

Gly Phe Ile Arg Asn Lys Ala Asn Gly Tyr Thr Thr Glu Phe Asn Pro
 50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Thr Tyr
                 85                  90                  95

Tyr Cys Ala Arg Arg Leu Tyr Gly Tyr Ala Tyr Tyr Val Met Asp
                100                 105                 110

Ala Trp Gly Gln Gly Thr Leu Val Thr Val Ser Ser
            115                 120
```

<210> SEQ ID NO 88
<211> LENGTH: 124
<212> TYPE: PRT
<213> ORGANISM: Artificial
<220> FEATURE:
<223> OTHER INFORMATION: C101W_AA

<400> SEQUENCE: 88

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Phe
             20                  25                  30

Tyr Met Asn Trp Val Arg Gln Pro Gly Lys Ala Pro Glu Trp Leu
            35                  40                  45

Gly Phe Ile Arg Asn Lys Ala Asn Gly Tyr Thr Thr Glu Phe Asn Pro
 50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Thr Tyr
                 85                  90                  95
```

```
Tyr Cys Ala Arg Trp Leu Tyr Gly Tyr Ala Tyr Tyr Val Met Asp
            100                 105                 110

Ala Trp Gly Gln Gly Thr Leu Val Thr Val Ser Ser
        115                 120

<210> SEQ ID NO 89
<211> LENGTH: 124
<212> TYPE: PRT
<213> ORGANISM: Artificial
<220> FEATURE:
<223> OTHER INFORMATION: C101P_AA

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Pro Leu Tyr Gly Tyr Ala Tyr Tyr Val Met Asp
            100                 105                 110

Ala Trp Gly Gln Gly Thr Leu Val Thr Val Ser Ser
        115                 120

<210> SEQ ID NO 90
<211> LENGTH: 124
<212> TYPE: PRT
<213> ORGANISM: Artificial
<220> FEATURE:
<223> OTHER INFORMATION: C101Q_AA

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Gln Leu Tyr Gly Tyr Ala Tyr Tyr Val Met Asp
            100                 105                 110

Ala Trp Gly Gln Gly Thr Leu Val Thr Val Ser Ser
        115                 120

<210> SEQ ID NO 91
<211> LENGTH: 378
<212> TYPE: DNA
```

<210> SEQ ID NO 91
<211> LENGTH: 378
<212> TYPE: DNA
<213> ORGANISM: Artificial
<220> FEATURE:
<223> OTHER INFORMATION: HuRA15-7LV3_DNA

<400> SEQUENCE: 91

```
atgaagttgc ctgttaggct gttggtgctg atgttctgga ttcctgcttc cagcagtgac      60
atccagatga cacagtctcc atcttccctg tctgcatctc tcggagatcg cgtcaccatc     120
acctgtcgaa caagtgaaga cattttccgt aatttagcgt ggtatcagca gaagccaggg     180
aaggctccta agctcctgat ctatgataca ataggttgg cagatggggt cccatcacgg      240
ttcagtggca gtggttctgg cacagactac actctaacca tatccagtct gcaacctgaa     300
gatttcgcaa cctatttctg tcaacaatat gacaattatc cgctcacgtt cggtcagggg     360
accaagctgg agatcaaa                                                   378
```

<210> SEQ ID NO 92
<211> LENGTH: 126
<212> TYPE: PRT
<213> ORGANISM: Artificial
<220> FEATURE:
<223> OTHER INFORMATION: HuRA15-7LV3_AA

<400> SEQUENCE: 92

```
Met Lys Leu Pro Val Arg Leu Leu Val Leu Met Phe Trp Ile Pro Ala
1               5                   10                  15
Ser Ser Ser Asp Ile Gln Met Thr Gln Ser Pro Ser Ser Leu Ser Ala
            20                  25                  30
Ser Leu Gly Asp Arg Val Thr Ile Thr Cys Arg Thr Ser Glu Asp Ile
        35                  40                  45
Phe Arg Asn Leu Ala Trp Tyr Gln Gln Lys Pro Gly Lys Ala Pro Lys
    50                  55                  60
Leu Leu Ile Tyr Asp Thr Asn Arg Leu Ala Asp Gly Val Pro Ser Arg
65                  70                  75                  80
Phe Ser Gly Ser Gly Ser Gly Thr Asp Tyr Thr Leu Thr Ile Ser Ser
                85                  90                  95
Leu Gln Pro Glu Asp Phe Ala Thr Tyr Phe Cys Gln Gln Tyr Asp Asn
            100                 105                 110
Tyr Pro Leu Thr Phe Gly Gln Gly Thr Lys Leu Glu Ile Lys
        115                 120                 125
```

<210> SEQ ID NO 93
<211> LENGTH: 321
<212> TYPE: DNA
<213> ORGANISM: Artificial
<220> FEATURE:
<223> OTHER INFORMATION: nonS_HuRA15-7LV3_DNA

<400> SEQUENCE: 93

```
gacatccaga tgacacagtc tccatcttcc ctgtctgcat ctctcggaga tcgcgtcacc      60
atcacctgtc gaacaagtga agacattttt cgtaatttag cgtggtatca gcagaagcca     120
gggaaggctc ctaagctcct gatctatgat acaaataggt tggcagatgg ggtcccatca     180
cggttcagtg gcagtggttc tggcacagac tacactctaa ccatatccag tctgcaacct     240
gaagatttcg caacctattt ctgtcaacaa tatgacaatt atccgctcac gttcggtcag     300
gggaccaagc tggagatcaa a                                                321
```

<210> SEQ ID NO 94
<211> LENGTH: 107

```
<212> TYPE: PRT
<213> ORGANISM: Artificial
<220> FEATURE:
<223> OTHER INFORMATION: nonS_HuRA15-7LV3_AA

<400> SEQUENCE: 94
```

Asp Ile Gln Met Thr Gln Ser Pro Ser Ser Leu Ser Ala Ser Leu Gly
1               5                   10                  15

Asp Arg Val Thr Ile Thr Cys Arg Thr Ser Glu Asp Ile Phe Arg Asn
            20                  25                  30

Leu Ala Trp Tyr Gln Gln Lys Pro Gly Lys Ala Pro Lys Leu Leu Ile
        35                  40                  45

Tyr Asp Thr Asn Arg Leu Ala Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Tyr Asp Asn Tyr Pro Leu
                85                  90                  95

Thr Phe Gly Gln Gly Thr Lys Leu Glu Ile Lys
            100                 105

```
<210> SEQ ID NO 95
<211> LENGTH: 429
<212> TYPE: DNA
<213> ORGANISM: Artificial
<220> FEATURE:
<223> OTHER INFORMATION: HuRA15-7CTVH_DNA

<400> SEQUENCE: 95
```

| | | |
|---|---|---|
| atgaacctcg ggctcagttt gattttcctt gccctcattt taaaaggtgt ccagtgtgag | 60 |
| gtgcagttgg tggaatctgg tggcggtttg gtacagccgg ggggttcttt gcgactctcc | 120 |
| tgtgcagctt ctggcttcac cttcactgat ttctacatga actgggtccg ccagcctcca | 180 |
| gggaaggccc ctgagtggct gggttttatt cgaaacaaag ctaatggtta cacaacagag | 240 |
| ttcaatccgt ctgtgaaggg gcggttcacc atctcccgag ataattccaa gaacagcctc | 300 |
| tatcttcaaa tgaactccct gaagactgag gacactgcca cctactactg tgcacgaacc | 360 |
| ctctatggct atgcctatta ctatgttatg gatgcctggg gtcaaggcac tctggtcact | 420 |
| gtctcctca | 429 |

```
<210> SEQ ID NO 96
<211> LENGTH: 143
<212> TYPE: PRT
<213> ORGANISM: Artificial
<220> FEATURE:
<223> OTHER INFORMATION: HuRA15-7CTVH_AA

<400> SEQUENCE: 96
```

Met Asn Leu Gly Leu Ser Leu Ile Phe Leu Ala Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asp Phe Tyr Met Asn Trp Val Arg Gln Pro Pro Gly Lys Ala Pro
50                  55                  60

Glu Trp Leu Gly Phe Ile Arg Asn Lys Ala Asn Gly Tyr Thr Thr Glu
65                  70                  75                  80

```
Phe Asn Pro Ser Val Lys Gly Arg Phe Thr Ile Ser Arg Asp Asn Ser
                85                  90                  95

Lys Asn Ser Leu Tyr Leu Gln Met Asn Ser Leu Lys Thr Glu Asp Thr
            100                 105                 110

Ala Thr Tyr Tyr Cys Ala Arg Thr Leu Tyr Gly Tyr Ala Tyr Tyr Tyr
        115                 120                 125

Val Met Asp Ala Trp Gly Gln Gly Thr Leu Val Thr Val Ser Ser
130             135                 140

<210> SEQ ID NO 97
<211> LENGTH: 372
<212> TYPE: DNA
<213> ORGANISM: Artificial
<220> FEATURE:
<223> OTHER INFORMATION: nonS_HuRA15-7CTVH_DNA

<400> SEQUENCE: 97
gaggtgcagt tggtggaatc tgtggcggt ttggtacagc cggggggttc tttgcgactc      60
tcctgtgcag cttctggctt caccttcact gatttctaca tgaactgggt ccgccagcct     120
ccagggaagg ccctgagtg gctgggtttt attcgaaaca agctaatgg ttacacaaca       180 gagttcaatc cgtctgtgaa ggggcggttc accatctccc gagataattc caagaacagc    240
ctctatcttc aaatgaactc cctgaagact gaggacactg ccacctacta ctgtgcacga    300 acctctatg gctatgccta ttactatgtt atggatgcct ggggtcaagg cactctggtc     360
actgtctcct ca                                                         372

<210> SEQ ID NO 98
<211> LENGTH: 124
<212> TYPE: PRT
<213> ORGANISM: Artificial
<220> FEATURE:
<223> OTHER INFORMATION: nonS_HuRA15-7CTVH_AA

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Phe
            20                  25                  30

Tyr Met Asn Trp Val Arg Gln Pro Pro Gly Lys Ala Pro Glu Trp Leu
        35                  40                  45

Gly Phe Ile Arg Asn Lys Ala Asn Gly Tyr Thr Thr Glu Phe Asn Pro
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Thr Tyr
                85                  90                  95

Tyr Cys Ala Arg Thr Leu Tyr Gly Tyr Ala Tyr Tyr Tyr Val Met Asp
            100                 105                 110

Ala Trp Gly Gln Gly Thr Leu Val Thr Val Ser Ser
        115                 120

<210> SEQ ID NO 99
<211> LENGTH: 13
<212> TYPE: PRT
<213> ORGANISM: Artificial
<220> FEATURE:
<223> OTHER INFORMATION: HuRA15-7CTVHCDR3_AA

<400> SEQUENCE: 99
```

Thr Leu Tyr Gly Tyr Ala Tyr Tyr Val Met Asp Ala
1               5                   10

<210> SEQ ID NO 100
<211> LENGTH: 124
<212> TYPE: PRT
<213> ORGANISM: Artificial
<220> FEATURE:
<223> OTHER INFORMATION: HV0_AA

<400> SEQUENCE: 100

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Phe
                20                  25                  30

Tyr Met Asn Trp Val Arg Gln Ala Pro Gly Lys Gly Leu Glu Trp Val
            35                  40                  45

Gly Phe Ile Arg Asn Lys Ala Asn Gly Tyr Thr Thr Glu Phe Asn Pro
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Cys Leu Tyr Gly Tyr Ala Tyr Tyr Val Met Asp
            100                 105                 110

Ala Trp Gly Gln Gly Thr Leu Val Thr Val Ser Ser
        115                 120

<210> SEQ ID NO 101
<211> LENGTH: 107
<212> TYPE: PRT
<213> ORGANISM: Artificial
<220> FEATURE:
<223> OTHER INFORMATION: LV0_AA

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asp Ile Phe Arg Asn
                20                  25                  30

Leu Ala Trp Tyr Gln Gln Lys Pro Gly Lys Ala Pro Lys Leu Leu Ile
            35                  40                  45

Tyr Asp Thr Asn Arg Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Tyr Pro Leu
                85                  90                  95

Thr Phe Gly Gln Gly Thr Lys Leu Glu Ile Lys
            100                 105

<210> SEQ ID NO 102
<211> LENGTH: 255
<212> TYPE: PRT
<213> ORGANISM: Rattus norvegicus

<400> SEQUENCE: 102

Met Ala His Leu Met Ala Gly Gln Trp Leu Leu Leu Leu Met Trp Met
1               5                   10                  15

-continued

```
Ala Glu Cys Ala Gln Ser Arg Ala Thr Arg Ala Arg Thr Glu Leu Leu
        20                  25                  30
Asn Val Cys Met Asp Ala Lys His His Lys Glu Lys Pro Gly Pro Glu
        35                  40                  45
Asp Lys Leu His Asp Gln Cys Ser Pro Trp Lys Thr Asn Ala Cys Cys
    50                  55                  60
Ser Thr Asn Thr Ser Gln Glu Asp Thr Lys Asp Ile Ser Tyr Leu Tyr
65                      70                  75                  80
Arg Phe Asn Trp Asn His Cys Gly Thr Met Thr Pro Glu Cys Lys Arg
                85                  90                      95
His Phe Ile Gln Asp Thr Cys Leu Tyr Glu Cys Ser Pro Asn Leu Gly
            100                 105                 110
Pro Trp Ile Gln Gln Val Asp Gln Ser Trp Arg Lys Glu Arg Ile Leu
            115                 120                 125
Asp Val Pro Leu Cys Lys Glu Asp Cys Val Leu Trp Trp Glu Asp Cys
        130                 135                 140
Lys Ser Ser Phe Thr Cys Lys Ser Asn Trp Leu Lys Gly Trp Asn Trp
145                     150                 155                 160
Thr Ser Gly His Asn Glu Cys Pro Val Gly Ala Ser Cys His Pro Phe
                165                 170                 175
Thr Phe Tyr Phe Pro Thr Pro Ala Val Leu Cys Glu Lys Ile Trp Ser
            180                 185                 190
His Ser Tyr Lys Leu Ser Asn Tyr Ser Arg Gly Ser Gly Arg Cys Ile
            195                 200                 205
Gln Met Trp Phe Asp Pro Ala Gln Gly Asn Pro Asn Glu Glu Val Ala
        210                 215                 220
Arg Phe Tyr Ala Glu Val Met Ser Gly Ala Gly Leu Arg Glu Ala Trp
225                 230                 235                 240
Leu Leu Val Cys Ser Leu Ser Leu Val Leu Phe Cys Val Val Ser
                245                 250                 255
```

ANTI-FOLR1 ANTIBODY

BACKGROUND OF THE INVENTION

The present invention relates to a monoclonal antibody which binds to Folate receptor α (hereinafter, referred to as FOLR1) and exhibits antibody-dependent cellular cytotoxicity activity (hereinafter, referred to as ADCC activity) and/or complement-dependent cytotoxicity activity (hereinafter, referred to as CDC activity) or an antibody fragment thereof, a DNA encoding the antibody or the antibody fragment thereof, a vector comprising the DNA, a transformant obtained by introducing the vector, a method for preparing the antibody or the antibody fragment thereof using the transformant, and a therapeutic agent and a diagnostic agent comprising the antibody or the antibody fragment as an active ingredient.

FOLR1 is a GPI-anchored membrane protein having a high affinity for folate, and has an important functions relating to cell proliferation or survival (Non-Patent Literature 1). FOLR1 shows restricted-expression pattern in the normal tissues of the kidney, lung, intestine or the like (Non-Patent Literature 2).

The expression region is localized in the lumen. Meanwhile, FOLR1 expression in cancer tissues is not restricted to the lumen, and its high expression is observed in a variety of cancers such as ovarian cancer (Non-Patent Literature 2, Non-Patent Literature 3, Non-Patent Literature 4), renal cancer (Non-Patent Literature 2), lung cancer (Non-Patent Literature 2, Non-Patent Literature 3), breast cancer (Non-Patent Literature 2), mesothelioma (Non-Patent Literature 4).

In particular, it was reported that FOLR1 expression level is related to malignancy grade, progression, and prognosis in ovarian cancer (Non-Patent Literature 5, Non-Patent Literature 6). Furthermore, it was also reported that soluble FOLR1 was significantly elevated in the serum of ovarian cancer patients compared to the serum of healthy donors (Non-Patent Literature 7). Thus, FOLR1 is a promising target molecule for cancer treatment.

LK26 is known as a mouse monoclonal antibody against FOLR1 (Patent Literature 1). LK26 was humanized by CDR grafting to be administered to a patient as an antibody for cancer treatment (Patent Literature 2). However, its affinity was remarkably reduced by the humanization.

For this reason, Ebel et al. prepared MORAb-003 antibody which has equivalent affinity against FOLR1 to that of LK26 antibody, based on humanized LK26 antibody (Non-Patent Literature 8). It is considered that in vitro anti-tumor activity of MORAb-003 is attributed to ADCC activity and CDC activity.

On the other hand, there is a report that MORAb-003 has no inhibitory activity against binding of folate, 5-methyltetrahydrofolate (5-MTHF), or pemetrexed to FOLR1-positive cells, and the antibody alone has no inhibitory activity against proliferation of FOLR1-positive cells (Non-Patent Literature 9).

Phase I clinical trial reported that MORAb-003 showed safety and tolerability at administration doses from 12.5 to 400 mg/m$^2$ (Non-Patent Literature 10). Moreover, Phase II clinical trial reported that MORAb-003 in combination with paclitaxel and carboplatin showed significant anti-tumor activity in patients with platinum-sensitive recurrent ovarian cancer.

However, clinical trial in patients with platinum-resistant recurrent ovarian cancer was discontinued because of the possibility of not meeting the endpoint of improving the predetermined statistical criteria (progression-free survival or overall survival duration) in an interim analysis.

An anti-cancer agent for targeting FOLR1 can be exemplified by EC-145 which is prepared by conjugating an anti-cancer agent to folate, in addition to the above anti-FOLR1 antibody. The folate-conjugated anti-cancer agent exhibits its efficacy, based on the folate-uptake property of FOLR1. Therefore, it is suggested that the folate-conjugated anti-cancer agent will be ineffective in the cancer cells with low folate uptake activity, although FOLR1 is expressed in the cancer cells of the body.

Despite continuous progress in the treatment of solid cancers and prognosis improvement, there has been no remarkable improvement in prognosis of ovarian cancer, since a therapy with a platinum agent emerged in 1980 (Non-Patent Literature 11), and ovarian cancer is still a main cause of cancer death in women. The reason is that ovarian cancer becomes resistant to the platinum agent and as a result, recurrent ovarian cancer is intractable.

That is, challenges in ovarian cancer treatment are to prolong a period before recurrence after response to the chemotherapy using a platinum agent or the like, to prevent resistance of ovarian cancer to the platinum agent, and to establish a therapy for platinum-resistant ovarian cancer.

Further, ovarian cancer is often associated with accumulation of ascitic fluid due to peritoneal dissemination. In particular, accumulation of ascitic fluid in the platinum-resistant ovarian cancer impairs QOL (Quality of Life), and thus there is a demand for therapeutic agents that are effective for cancer cells present in peritoneal dissemination or ascitic fluid as well as cancer cells in primary site.

There is also a demand for therapeutic agents effective for the cancer cells that show high FOLR1 expression but have low folate uptake activity.

CITATION LIST

Patent Literatures

[Patent Literature 1] EP Patent Application Publication No. 0197435
[Patent Literature 2] U.S. Pat. No. 5,952,484

Non-Patent Literatures

[Non-Patent Literature 1] Int J Cancer, 2006. 119(2): p. 243-50.
[Non-Patent Literature 2] Anal Biochem, 2005. 338(2): p. 284-93.
[Non-Patent Literature 3] J Thorac Oncol, 2012. 7(5): p. 833-840.
[Non-Patent Literature 4] J Thorac Cardiovasc Surg, 2001. 121(2): p. 225-33.
[Non-Patent Literature 5] Int J Cancer, 1997. 74(2): p. 193-8.
[Non-Patent Literature 6] Int J Cancer, 1998. 79(2): p. 121-6.
[Non-Patent Literature 7] PLoS One, 2009. 4(7): p.e6292.
[Non-Patent Literature 8] Cancer Immun, 2007. 7: p. 6.
[Non-Patent Literature 9] Cancer Chemother Pharmacol, 2012. 70(1): p. 113-20.
[Non-Patent Literature 10] Clin Cancer Res, 2010. 16(21): p. 5288-95.
[Non-Patent Literature 11] Nat Rev Cancer, 2011. 11(10): p. 719-25.

SUMMARY OF THE INVENTION

An anti-FOLR1 antibody showing dramatically increased ADCC activity and/or CDC activity is expected as an antibody for the treatment of cancers characterized by FOLR1 expression, including intractable platinum-resistant ovarian cancer.

The present invention provides an antibody or an antibody fragment thereof that exhibits an anti-tumor activity against cell lines in vitro and in vivo, even if they are derived from platinum-resistant ovarian cancer. Further, the present invention provides a DNA encoding the antibody or the antibody fragment thereof, a vector comprising the DNA, a transformant obtained by introducing the vector, a method for producing the antibody or the antibody fragment thereof using the transformant, and a therapeutic agent and a diagnostic agent comprising the antibody or the antibody fragment as an active ingredient.

The monoclonal antibody of the present invention or the antibody fragment thereof specifically recognizes an amino acid sequence of human FOLR1 or a conformational structure thereof and binds thereto. The monoclonal antibody of the present invention or the antibody fragment thereof has high ADCC activity and CDC activity, and further exhibits an anti-tumor activity against platinum-resistant ovarian cancer-derived cell lines.

The monoclonal antibody of the present invention or the antibody fragment thereof has an ADCC activity against cells with low FOLR1 expression. The monoclonal antibody of the present invention or the antibody fragment thereof also has an ADCC activity against FOLR1-expressing cancer cells present in ascitic fluid. Furthermore, the monoclonal antibody of the present invention or the antibody fragment thereof has an ADCC activity against FOLR1-expressing cancer cells although the cancer cells have reduced folate uptake activity.

Further, the monoclonal antibody of the present invention or the antibody fragment thereof does not inhibit binding of folate to FOLR1. The monoclonal antibody of the present invention or the antibody fragment thereof that specifically binds to human FOLR1 and also has high ADCC activity and CDC activity is useful for the treatment and diagnosis of diseases associated with human FOLR1-positive cells.

Furthermore, the present invention can provide a DNA encoding the antibody, a vector comprising the DNA, a transformant obtained by introducing the vector, a method for producing the antibody or the antibody fragment thereof using the transformant, and a therapeutic agent and a diagnostic agent comprising the antibody or the antibody fragment as an active ingredient.

The summary of the present invention is as follows.

(1) A monoclonal antibody or an antibody fragment thereof that competes with one antibody selected from the following (a)-(c) to specifically recognize human FOLR1 and binds to an epitope identical to the epitope on human FOLR1 to which the antibody binds, and also shows an anti-tumor activity:

(a) an antibody in which complementarity determining regions (hereinafter, referred to as CDRs) 1-3 of heavy chain (hereinafter, referred to as H chain) of the antibody comprise the amino acid sequences represented by SEQ ID NOs. 30, 31, and 32, respectively and CDRs 1-3 of light chain (hereinafter, referred to as L chain) of the antibody comprise the amino acid sequences represented by SEQ ID NOs. 33, 34, and 35, respectively;

(b) an antibody in which CDRs 1-3 of H chain of the antibody comprise the amino acid sequences represented by SEQ ID NOs. 30, 31, and 32, respectively and CDRs 1-3 of L chain of the antibody comprise the amino acid sequences represented by SEQ ID NOs. 33, 34, and 35, respectively, and cysteine in the amino acid sequence represented by SEQ ID NO. 32 (CDR3 of antibody H chain) is substituted with threonine, methionine, isoleucine, valine, phenylalanine, or glutamine, regarding the antibody; and (c) an antibody in which H chain of the antibody comprises the amino acid sequence represented by SEQ ID NO. 98, and L chain of the antibody comprises the amino acid sequence represented by SEQ ID NO. 94.

(2) The monoclonal antibody or the antibody fragment thereof described in (1), which is a recombinant antibody.

(3) The monoclonal antibody or the antibody fragment thereof described in (2), wherein the recombinant antibody is selected from a human chimeric antibody, a humanized antibody and a human antibody.

(4) A monoclonal antibody or an antibody fragment thereof that is selected from the following (a)-(c):

(a) a monoclonal antibody and an antibody fragment thereof in which CDRs 1-3 of H chain of the antibody comprise the amino acid sequences represented by SEQ ID NOs. 30, 31, and 32, respectively and CDRs 1-3 of L chain of the antibody comprise the amino acid sequences represented by SEQ ID NOs. 33, 34, and 35, respectively;

(b) an antibody in which CDRs 1-3 of H chain of the antibody comprise the amino acid sequences represented by SEQ ID NOs. 30, 31, and 32, respectively and CDRs 1-3 of L chain of the antibody comprise the amino acid sequences represented by SEQ ID NOs. 33, 34, and 35, respectively, and cysteine in the amino acid sequence represented by SEQ ID NO. 32 (CDR3 of antibody H chain) is substituted with threonine, methionine, isoleucine, valine, phenylalanine, or glutamine; and (c) an antibody in which H chain of the antibody comprises the amino acid sequence represented by SEQ ID NO. 98, and L chain of the antibody comprises the amino acid sequence represented by SEQ ID NO. 94.

(5) The monoclonal antibody and the antibody fragment thereof described in any one of (1) to (4), which bind to the amino acid sequence of human FOLR1 represented by SEQ ID NO. 1.

(6) The antibody fragment thereof described in any one of (1) to (4), which is selected from Fab, Fab', F(ab')$_2$, a single chain antibody (scFv), a dimeric V region (diabody), a disulfide-stabilized V region (dsFv), and a peptide comprising CDR.

(7) A DNA encoding the monoclonal antibody or the antibody fragment thereof described in any one of (1) to (4).

(8) A recombinant vector comprising the DNA described in (7).

(9) A transformant that is obtained by introducing the recombinant vector of (8) into host cells.

(10) A method for producing the monoclonal antibody or the antibody fragment thereof of (1) or (4), comprising culturing the transformant of (9) in a medium, producing and accumulating the monoclonal antibody or the antibody fragment thereof of (1) or (4) in the culture, and collecting the antibody or the antibody fragment thereof from the culture.

(11) A method for treating diseases associated with human FOLR1-positive cells, comprising administrating the monoclonal antibody or the antibody fragment thereof of any one of (1) to (4).

(12) A pharmaceutical composition comprising the monoclonal antibody or the antibody fragment thereof of any one of (1) to (4) and a pharmaceutically acceptable carrier.

(13) A method for immunologically detecting or measuring human FOLR1 or human FOLR1-positive cells using the monoclonal antibody or the antibody fragment thereof of any one of (1) to (4).

(14) A method for diagnosing diseases associated with human FOLR1-positive cells, comprising detecting or measuring human FOLR1-positive cells using the monoclonal antibody or the antibody fragment thereof of any one of (1) to (4).

(15) A method for evaluating therapeutic efficacy of an antibody using the monoclonal antibody or the antibody fragment thereof of any one of (1) to (4), before treatment initiation.

BRIEF DESCRIPTION OF THE DRAWINGS

FIG. 1 shows the amino acid sequences of the heavy chain variable region of RA15-7 antibody containing no signal sequence and the heavy chain variable region (HV0, HV2, HV3, HV4, HV5, HV6, HV7, HV8, HV10) of each modified humanized RA15-7 antibody.

FIG. 2 shows the amino acid sequences of the light chain variable region of RA15-7 antibody containing no signal sequence and the light chain variable region (LV0, LV2, LV3, LV4, LV6) of each modified humanized RA15-7 antibody.

FIGS. 4 (a), (b), (c), and (d) show the results (ELISA) of evaluating reactivity of each antibody (DNPDF, MORAb-003DF, ChRA15-7DF, and HuRA15-7CTDF) against FOLR1-Fc (black circle), cynomolgus monkey FOLR1-Fc (white circle), FOLR2-Fc (black triangle), and FOLR3-Fc (x), in which the vertical axis represents absorbance, and the horizontal axis represents antibody concentration (ng/mL).

FIGS. 5(a) and (b) show the ADCC activities of HuRA15-7CTAcc antibody (black circle), HuRA15-7Acc antibody (black square), and ChRA15-7Acc antibody (black triangle) against the platinum-resistant ovarian cancer cell line SKOV-3 or OVCAR-3, in which the vertical axis represents ADCC activity (%), and the horizontal axis represents antibody concentration (ng/mL).

FIGS. 6(a) and (b) show CDC activity against the ovarian cancer cell line IGR-OV1, in which the vertical axis represents CDC activity (%), and the horizontal axis represents antibody concentration (ng/mL). FIG. 6(a) shows the CDC activities of HuRA15-7CTAcc antibody (black circle), HuRA15-7CTDF antibody (white circle), ChRA15-7Acc antibody (black triangle), and ChRA15-7DF antibody (white triangle). FIG. 6(b) shows the CDC activities of HuRA15-7CTAcc antibody (black circle) and MORAb-003 antibody (black triangle).

FIGS. 7(a), (b), and (c) show the ADCC activities of HuRA15-7CTAcc antibody (black circle), MORAb-003Acc antibody (white triangle), and MORAb-003 antibody (black triangle) against the ovarian cancer cell line IGR-OV1, SKOV-3, or OVCAR-3, in which the vertical axis represents ADCC activity (%), and the horizontal axis represents antibody concentration (ng/mL).

FIG. 12(a) shows the FOLR1 expression level by flow cytometry using HuRA15-7CTAcc antibody.

DETAILED DESCRIPTION OF THE EXEMPLARY EMBODIMENTS

Figure 3:
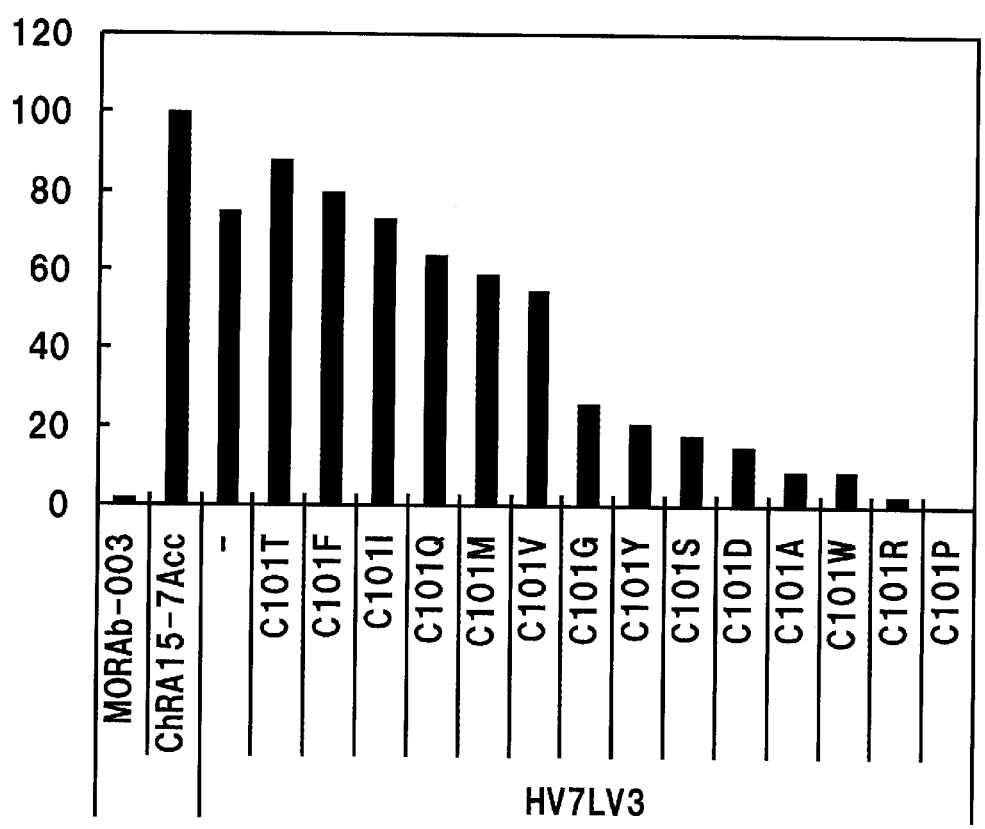
FIG. 3 shows the result (surface plasmon resonance method) of evaluating affinity of HV7LV3-CDRH3-Cys101 modified antibody against FOLR1-mycHis when affinity of ChRA15-7Acc antibody was regarded as 100 by using surface plasmon resonance method.

Examples of human FOLR1 of the present invention may include a polypeptide comprising an amino acid sequence represented by SEQ ID NO. 1 and also having a function of human FOLR1, a polypeptide comprising the amino acid sequence represented by SEQ ID NO. 1 in which one or more amino acids are deleted, substituted, or added and also having the function of human FOLR1, a polypeptide comprising the amino acid sequence having at least 60% homology, preferably at least 80% homology, more preferably at least 90% homology, and most preferably at least 95% homology, with the amino acid sequence represented by SEQ ID NO. 1 and also having the function of human FOLR1, a polypeptide comprising an amino acid sequence composed of a partial sequence of the amino acid sequence represented by SEQ ID NO. 1 and also having the function of human FOLR1, or the like.

The function of human FOLR1 refers to the cause of endocytosis by binding with a ligand (e.g., folate) and intracellular uptake of folate.

Examples of the method for obtaining the polypeptide comprising the amino acid sequence represented by SEQ ID NO. 1, in which one or more amino acids are deleted, substituted, or added may include a method of introducing a site-specific mutation into DNA encoding a polypeptide having the amino acid sequence represented by SEQ ID NO. 1, namely, a gene encoding human FOLR1 using site-specific mutagenesis [Molecular Cloning, A Laboratory Manual, Second Edition, Cold Spring Harbor Laboratory Press (1989), Current Protocols in molecular Biology, John Wiley&Sons (1987-1997), Nucleic Acids Research, 10, 6487 (1982), Proc. Natl. Acad. Sci. USA, 79, 6409, (1982), Gene, 34, 315(1985), Proc. Natl. Acad. Sci. USA, 82, 488 (1985)] or the like.

The number of amino acids which are deleted, substituted or added is, but not particularly limited to, preferably 1 to dozens, for example, 1 to 20, more preferably 1 to several, for example, 1 to 5.

Examples of the gene encoding human FOLR1 may include a nucleotide sequence represented by GenBank Accession NO. NM_016725. The gene encoding human FOLR1 of the present invention may include a gene comprising a DNA composed of a nucleotide sequence having deletion, substitution or addition of one or more nucleotides in the nucleotide sequence represented by or GenBank Accession NO. NM_016725 and also encoding a polypeptide having the function of human FOLR1, a gene comprising a DNA composed of the nucleotide sequence having at least 60% or more, preferably 80% or more, and more preferably 95% or more homology to the nucleotide sequence represented by GenBank Accession NO. NM_016725 and also encoding a polypeptide having the function of human FOLR1, a gene comprising a DNA which hybridizes with a DNA having the nucleotide sequence represented by GenBank Accession NO. NM_016725 under stringent conditions and also encoding a polypeptide having the function of human FOLR1, or the like.

The DNA which hybridizes under stringent conditions refers to a hybridizable DNA which is obtained by colony hybridization, plaque hybridization, Southern blot hybridization, DNA microarray, or the like using a DNA having the nucleotide sequence represented by GenBank Accession NO. NM_016725 as a probe.

A specific example thereof may include a DNA which can be identified by the hybridization [Molecular Cloning, A Laboratory Manual, Second Edition, Cold Spring Harbor Laboratory Press (1989), Current Protocols in molecular Biology, John Wiley&Sons (1987-1997), DNA Cloning 1: Coretechniques, A Practical Approach, Second Edition, Oxford University (1995)] using the filter or slide glass, on which a DNA derived from hybridized colony or plaque, or PCR product or oligo DNA having the sequence is immobilized, under the presence of 0.7-1.0 mol/L sodium chloride at 65° C., and then washing the filter or slide glass at 65° C. with a 0.1-2-fold concentration SSC solution (1-fold concentration SSC solution: 150 mmol/L sodium chloride and 15 mmol/L sodium citrate).

Examples of the hybridizable DNA may include DNA having at least 60% or more homology, preferably 80% or more homology, more preferably 95% or more homology to the nucleotide sequence represented by or GenBank Accession NO. NM_016725.

In the nucleotide sequence of the gene encoding a protein of a eukaryote, genetic polymorphism is often found. The gene encoding FOLR1 of the present invention also includes a gene in which minor modifications are generated in the nucleotide sequence of the gene by such polymorphism.

The number of the homology described in the present invention may be a number calculated by using a homology search program known by those skilled in the art, unless specifically indicated. Regarding the nucleotide sequence, the number may be calculated by BLAST [J. Mol. Biol., 215, 403 (1990)] with a default parameter or the like. Further, regarding the amino acid sequence, the number may be calculated by using BLAST2 [Nucleic Acids Res., 25, 3389 (1997), Genome Res., 7, 649 (1997), www.ncbi.nlm.nih.gov/Education/BLASTinfo/information3.html] with a default parameter or the like.

As the default parameter, G (cost to open gap) is 5 for the nucleotide sequence and 11 for the amino acid sequence; −E (cost to extend gap) is 2 for the nucleotide sequence and 1 for the amino acid sequence; −q (penalty for nucleotide mismatch) is −3; −r (reward for nucleotide match) is 1; −e (expect value) is 10; −W (word size) is 11 residues for the nucleotide sequence and 3 residues for the amino acid sequence; −y [Dropoff(X) for blast extensions in bits] is 20 for blastn and 7 for a program other than blastn; −X (X dropoff value for gapped alignment in bits) is 15; and Z (final X dropoff value for gapped alignment in bits) is 50 for blastn and 25 for a program other than blastn (www.ncbi.nlm.nih.gov/blast/html/blastcgihelp.html).

The polypeptide composed of a partial sequence of the amino acid sequence represented by SEQ ID NO. 1 can be prepared, for example, by partially deleting a DNA encoding the amino acid sequence represented by SEQ ID NO. 1, and culturing a transformant into which an expression vector comprising the partially deleted DNA is introduced.

The polypeptide having an amino acid sequence in which one or more amino acids are deleted, substituted or added in the partial sequence of the amino acid sequence represented by SEQ ID NO. 1 can be also obtained by the above described site-specific mutagenesis.

Further, the polypeptide composed of the partial sequence of the amino acid sequence represented by SEQ ID NO. 1, or the polypeptide in which one or more amino acids are deleted, substituted, or added in the partial sequence of the amino acid sequence represented by SEQ ID NO. 1 can also be prepared by a chemical synthesis method such as a fluorenylmethyloxycarbonyl (Fmoc) method, a t-butyloxycarbonyl (tBoc) method, or the like.

The monoclonal antibody (hereinafter, referred to as antibody of the present invention) or the antibody fragment thereof is an antibody or an antibody fragment thereof which specifically recognizes the amino acid sequence of human FOLR1 or the conformational structure thereof and binds thereto and has an anti-tumor activity.

In the present invention, the conformational structure of human FOLR1 may be any structure, as long as it has a structure equivalent to a structure which can be formed in a native state by human FOLR1 having the amino acid sequence from position 1 to position 257 in the amino acid sequence represented by SEQ ID NO. 1. The conformational structure which can be formed in a native state by human FOLR1 refers to a native conformational structure of human FOLR1.

Specifically, the anti-tumor activity in the present invention may include ADCC activity and CDC activity.

The ADCC activity in the present invention is a cytolytic reaction in which an antibody bound to human FOLR1 on the cell surface binds to FcγRIIIa on the surface of mainly natural killer cell (hereinafter, referred to as NK cell) via Fc moiety, and as a result, the reaction is generated by cytotoxic molecules, such as perforin and granzyme, released from the NK cell [Clark M, Chemical. Immunology, 65, 88 (1997); Gorter A et al., Immunol. Today, 20, 576 (1999)].

The antibody of the present invention has ADCC activity against the cells with low FOLR1 expression as well as cells with high FOLR1 expression. Further, the antibody of the present invention exhibits higher ADCC activity against the cells with low FOLR1 expression, compared to the conventional anti-FOLR1 monoclonal antibodies. The FOLR1 expression level in cells can be confirmed by Western blotting, a known immunological detection method, a fluorescent cell staining method, or the like.

Specific examples thereof may include a fluorescent antibody staining method using an FMAT8100HTS System (manufactured by Applied Biosystems) [Cancer Immunol. Immunother., 36, 373 (1993)] or the like, a fluorescent cell staining method using flow cytometry, or the like. The antibody of the present invention also has an ADCC activity against FOLR1-expressing cells with low folate uptake activity.

The amount of folate uptake in the cells can be confirmed by, for example, using folate labeled with a label which is commonly used in the immunological detection or measurement method. Examples of the label may include enzymes such as alkaline phosphatase, peroxidase, luciferase or the like, luminescent materials such as acridinium ester, lophine or the like, fluorescent materials such as fluorescein isothiocyanate (FITC) or tetramethyl rhodamine isothiocyanate (RITC), radioactive material, or the like.

The CDC activity in the present invention is a cytolytic reaction in which an antibody bound to human FOLR1 on the cell surface binds to C1q, which is a component of C1 of the complement system, via Fc moiety, and as a result, respective complement components of C1 to C9 are activated and finally, C5 to C9 form a pore-forming aggregate known as the membrane attack complex on the cell membrane [Immunol Today. 1999 December; 20 (12): 576-82.].

Specifically, the antibody may include monoclonal antibodies of the following (i) to (ii) and antibody fragments thereof.

(i) an antibody in which CDRs 1-3 of H chain of the antibody comprise the amino acid sequences represented by SEQ ID NOs. 30, 31, and 32, respectively and CDRs 1-3 of L chain of the antibody comprise the amino acid sequences represented by SEQ ID NOs. 33, 34, and 35, respectively (ii) an antibody in which CDRs 1-3 of H chain of the antibody comprise the amino acid sequences represented by SEQ ID NOs. 30, 31, and 32, respectively and CDRs 1-3 of L chain of the antibody comprise the amino acid sequences represented by SEQ ID NOs. 33, 34, and 35, respectively, and in which cysteine in the amino acid sequence represented by SEQ ID NO. 32 (CDR3 of antibody H chain) is substituted with threonine, methionine, isoleucine, valine, phenylalanine, or glutamine.

More specifically, the monoclonal antibody of the present invention may include a monoclonal antibody of the following (a) and an antibody fragment thereof.

(a) a monoclonal antibody and an antibody fragment thereof, in which VH of the antibody comprises the amino acid sequence represented by SEQ ID NO. 98, and VL of the antibody comprises the amino acid sequence represented by SEQ ID NO. 94.

Further, the monoclonal antibody of the present invention may include a monoclonal antibody or an antibody fragment thereof that competes with the above monoclonal antibody for specific binding to the amino acid sequence of human FOLR1 or the conformational structure thereof and bind to an epitope that is identical to the epitope on human FOLR1 to which the above monoclonal antibody binds.

In the present invention, the antibody that competes with the monoclonal antibody refers to an antibody having an epitope (also called antigenic determinant) of human FOLR1 that is identical or partially identical to that of the monoclonal antibody of the present invention and binding to the epitope. The antibody that binds to an epitope identical to the epitope to which the monoclonal antibody of the present invention binds refers to an antibody that recognizes and binds to a sequence identical to the amino acid sequence of human FOLR1 recognized by the monoclonal antibody of the present invention.

Binding of the monoclonal antibody of the present invention or the antibody fragment thereof to the amino acid sequence of human FOLR1 or the conformational structure thereof can be confirmed by a method capable of investigating a particular antigen and a binding of an antibody to the particular antigen such as enzyme-linked immunosorbent assay (ELISA) using a solid-phase human FOLR1, Western blotting, or immunohistochemistry (IHC), or by a known immunological detection method or a fluorescent cell staining method for human FOLR1-expressing cells.

Specific examples may include a fluorescent antibody staining method using an FMAT8100HTS System (manufactured by Applied Biosystems) [Cancer Immunol. Immunother., 36, 373 (1993)] or the like, a fluorescent cell staining method using flow cytometry, surface plasmon resonance using a Biacore System (manufactured by GE Healthcare) or the like, or isothermal titration calorimetry using ITC (manufactured by DKSH), or the like.

When the binding of the monoclonal antibody of the present invention or the antibody fragment thereof to the amino acid sequence of human FOLR1 or the conformational structure thereof is examined by surface plasmon resonance using a Biacore System (manufactured by GE Healthcare) or the like, an anti-IgG antibody is immobilized onto a CM5 sensor chip by an amine coupling method, and then the antibody or the antibody fragment thereof is allowed to flow and bind at an appropriate amount, and FOLR1 or a conjugate thereof at various known concentrations is further allowed to flow, followed by measurement of the association and dissociation.

Further, the known immunoassays [Monoclonal Antibodies-Principles and practice, Third edition, Academic Press (1996), Antibodies—A Laboratory Manual, Cold Spring Harbor Laboratory (1988), Manual for monoclonal antibody experiments, Kodansha Scientific (1987)] and the like may be used in combination for detection.

The human FOLR1-expressing cell may be any cell as long as it expresses human FOLR1, and for example, a cell which is naturally present in the human body, a cell line established from the cell which is naturally present in the human body, a cell obtained by gene recombination technology, or the like.

Example of the cell which is naturally present in the human body may include a FOLR1-expressing cell in the body of a cancer patient, specifically, ovarian cancer cell, renal cancer cell, endometrial cancer cell, lung cancer cell, breast cancer cell, bladder cancer cell, pancreatic cancer cell, colon cancer cell, or the like [Anal Biochem, 2005. 338 (2): p. 284-293.].

Example of the cell line established from the cell which is naturally present in the human body may include a cell line expressing FOLR1, among cell lines prepared by establishing the FOLR1-expressing cells obtained from the above cancer patients.

Examples thereof may include SKOV-3 [American Type Culture Collection (hereinafter, referred to as ATCC) NO. HTB-77], TOV-112D (ATCC NO. CRL-11731), ES-2 (ATCC NO. CRL-1978), OV-90 (ATCC NO. CRL-11732), PA-1 (ATCC NO. CRL-1572), Caov-3 (ATCC NO. HTB-75), OVISE (JCRB cell NO. JCRB1043), MCAS (JCRB cell NO. JCRB0240), NIH:OVCAR-3 (ATCC NO. HTB-161), IGR-OV1 (National Cancer Institute), or RMG-1 (JCRB cell NO. JCRB0172), which is an ovarian cancer-derived cell line established from human.

Specific examples of the cell obtained by gene recombination technologys may include a FOLR1-expressing cell obtained by introducing an expression vector comprising a FOLR1-encoding cDNA into an insect cell, an animal cell or the like.

The monoclonal antibody of the present invention may include an antibody produced by a hybridoma and a recombinant antibody produced by a transformant transformed with an expression vector comprising an antibody gene.

The monoclonal antibody is characterized in that it is an antibody secreted by a single clone antibody-producing cell, and recognizes only one epitope (also called antigen determinant) and has uniform amino acid sequence (primary structure) constituting the monoclonal antibody.

Examples of the epitope may include a single amino acid sequence, a conformational structure composed of the amino acid sequence, a sugar chain-bound amino acid sequence, a conformational structure composed of the sugar chain-bound amino acid sequence, or the like, which is recognized and bound by the monoclonal antibody.

The epitope to which the monoclonal antibody of the present invention binds is preferably included in the amino acid sequence at positions 55 to 62 in the amino acid sequence of human FOLR1 represented by SEQ ID NO. 1.

The amino acid sequence of the epitope to which the monoclonal antibody of the present invention binds preferably comprises at least one amino acid selected from the amino acids at positions 55 to 62, and more preferably comprises at least one amino acid selected from the amino acids at positions 55, 56, 57, 58, 59, 60, 61, and 62 in the amino acid sequence of SEQ ID NO. 1.

Further, the amino acid sequence of the epitope to which the monoclonal antibody of the present invention binds preferably comprises at least two consecutive amino acids selected from the amino acids at positions 55 to 62 of SEQ ID NO. 1, and more preferably comprises at least one amino acid selected from the amino acids at positions 55, 56, 57, 58, 59, 60, 61, and 62 and also at least two consecutive amino acids selected from the amino acids at positions 55 to 62 of SEQ ID NO. 1 in the amino acid sequence of human FOLR1.

Specific examples of the amino acid sequence of the epitope to which the monoclonal antibody of the present invention binds may include an amino acid sequence comprising the amino acids at positions 55 to 62 of SEQ ID NO. 1, or the like.

The hybridoma may be, for example, obtained by preparing the above described human FOLR1-expressing cell as an antigen, inducing antibody-producing cells having antigen specificity in an animal immunized with the antigen, and performing fusion of the antibody-producing cells with myeloma cells. This hybridoma is cultured or injected into an animal to develop canceration of the ascitic fluid, and the culture broth or ascitic fluid is isolated and purified, thereby obtaining an anti-FOLR1 monoclonal antibody.

The animal immunized with the antigen may be any one as long as it can be used for the preparation of the hybridoma, and preferably mouse, rat, hamster, chicken, rabbit or the like. Further, antibodies produced from the hybridoma that is prepared by obtaining cells having an antibody-producing ability from the animals, performing immunization of these cells in vitro, and then performing fusion of the cells with myeloma cells are also included in the antibody of the present invention.

The recombinant antibody of the present invention includes antibodies produced by genetic recombination, such as a human chimeric antibody, a human CDR grafted antibody, a human antibody, an antibody fragment thereof or the like. The recombinant antibody having the properties of monoclonal antibody, low antigenicity, and prolonged blood half-life are preferred as a therapeutic agent. Example of the recombinant antibody may include those prepared by modifying the monoclonal antibody of the present invention using a genetic recombination technology.

The human chimeric antibody refers to an antibody comprising VH and VL of an antibody of non-human animal and a heavy chain constant region (hereinafter, referred to as CH) and a light chain constant region (hereinafter, referred to as CL) of a human antibody. The human chimeric antibody of the present invention can be produced by obtaining cDNAs encoding VH and VL from the hybridoma producing the monoclonal antibody which specifically recognizes and binds to the amino acid sequence of human FOLR1 or the conformational structure thereof, inserting the cDNAs to each of expression vectors for animal cells having genes encoding CH and CL of a human antibody so as to construct a human chimeric antibody-expressing vector, and introducing this vector to animal cells for expression.

CH of the human chimeric antibody may be any one as long as it belongs to human immunoglobulins (hereinafter, referred to as hIg), preferably those belonging to hIgG class, and also, any of subclasses hIgG1, hIgG2, hIgG3 or hIgG4 belonging to hIgG class. Further, CL of the human chimeric antibody may be any one as long as it belongs to hIg, and those belonging to κ or λ class can be used.

Specific example of the human chimeric antibody of the present invention may include a chimeric antibody which comprises VH of an antibody comprising the amino acid sequence represented by SEQ ID NO. 27 and comprises VL of an antibody comprising the amino acid sequence represented by SEQ ID NO. 29.

Further, the chimeric antibody of the present invention may include a chimeric antibody that competes with the monoclonal antibody of the present invention to specifically recognize and bind to the amino acid sequence of human FOLR1 or the conformational structure thereof, and bind to an epitope that is identical to the epitope on human FOLR1 to which the monoclonal antibody binds.

The human CDR grafted antibody, also called humanized antibody, refers to an antibody that is produced by grafting the amino acid sequence of CDRs of VH and VL of a non-human animal antibody to the proper region of VH and VL of a human antibody. The human CDR grafted antibody of the present invention can be produced by constructing cDNA encoding V region obtained by grafting the amino acid sequence of CDRs of VH and VL of a non-human animal monoclonal antibody, which specifically recognizes and binds to the amino acid sequence of human FOLR1 or the conformational structure thereof, to the framework region (hereinafter, referred to as FR) of VH and VL of any human antibody, inserting the cDNA to each of expression vectors for animal cells having genes encoding CH and CL of a human antibody so as to construct a human CDR-grafted antibody-expressing vector, and introducing this vector to animal cells for expression.

CH of the human CDR grafted antibody may be any one as long as it belongs to hIg, preferably those belonging to hIgG class, and also, any of subclasses hIgG1, hIgG2, hIgG3 or hIgG4 belonging to hIgG class. Further, CL of the human CDR grafted antibody may be any one as long as it belongs to hIg, and those belonging to κ or λ class can be used.

Specific example of the human CDR grafted antibody of the present invention may include a humanized antibody which comprises VH of an antibody comprising CDRs 1-3 having the amino acid sequences represented by SEQ ID NOs. 30-32 and comprises VL of an antibody comprising CDRs 1-3 having the amino acid sequences represented by SEQ ID NOs. 33-35.

Specific example of the humanized antibody of the present invention may include a humanized antibody comprising at least one of the following (a) VH and (b) VL.

(a) VH of antibody comprising an amino acid sequence of SEQ ID NO. 100, or an amino acid sequence in which at least one amino acid residue selected from Leu at position 18, Ser at position 30, Val at position 37, Ala at position 40, Pro at position 41, Gly at position 44, Leu at position 45, Val at position 48, Asp at position 76 and Val at position 95 in the amino acid sequence of SEQ ID NO. 100 is substituted with other amino acid residue.

(b) VL of antibody comprising an amino acid sequence of SEQ ID NO. 101, or an amino acid sequence in which at least one amino acid residue selected from Val at position 15, Ala at position 43, Lys at position 45, Phe at position 71, Thr at position 85, and Tyr at position 87 in the amino acid sequence of SEQ ID NO. 101 is substituted with other amino acid residue.

Further, VH included in the humanized antibody of the present invention is preferably the following (1)-(8).

(1) VH comprising an amino acid sequence in which Leu at position 18, Ser at position 30, Val at position 37, Ala at position 40, Pro at position 41, Gly at position 44, Leu at position 45, Val at position 48, Asp at position 76 and Val at position 95 in the amino acid sequence of SEQ ID NO. 100 are substituted with other amino acid residue.

(2) VH comprising an amino acid sequence in Val at position 37, Ala at position 40, Pro at position 41, Gly at position 44, Leu at position 45, Val at position 48, Asp at position 76 and Val at position 95 in the amino acid sequence of SEQ ID NO. 100 are substituted with other amino acid residue.

(3) VH comprising an amino acid sequence in which Ser at position 30, Ala at position 40, Gly at position 44, Leu at position 45, Val at position 48, Asp at position 76 and Val at position 95 in the amino acid sequence of SEQ ID NO. 100 are substituted with other amino acid residue.

(4) VH comprising an amino acid sequence in which Val at position 37, Ala at position 40, Pro at position 41, Leu at position 45, Val at position 48 and Val at position 95 in the amino acid sequence of SEQ ID NO. 100 are substituted with other amino acid residue.

(5) VH comprising an amino acid sequence in which Val at position 37, Ala at position 40, Pro at position 41, Leu at position 45 and Val at position 48 in the amino acid sequence of SEQ ID NO. 100 are substituted with other amino acid residue.

(6) VH comprising an amino acid sequence in which Ala at position 40, Pro at position 41, Leu at position 45 and Val at position 95 in the amino acid sequence of SEQ ID NO. 100 are substituted with other amino acid residue.

(7) VH comprising an amino acid sequence in which Pro at position 41, Leu at position 45, and Val at position 95 in the amino acid sequence of SEQ ID NO. 100 are substituted with other amino acid residue.

(8) VH comprising an amino acid sequence in which Ala at position 40 and Val at position 95 in the amino acid sequence of SEQ ID NO. 100 are substituted with other amino acid residue.

Example of the amino acid sequence of VH may include an amino acid sequence, which is introduced with at least one modification selected from substitution of Leu with Met at position 18, substitution of Ser with Thr at position 30, substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

Specific example of the amino acid sequence of VH introduced with 10 modifications may include an amino acid sequence, which is introduced with substitution of Leu with Met at position 18, substitution of Ser with Thr at position 30, substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

Specific example of the amino acid sequence of VH introduced with 9 modifications may include the amino acid sequences of the following (1)-(10).

(1) an amino acid sequence which is introduced with substitution Leu with Met at position 18, substitution of Ser with Thr at position 30, substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48, and substitution of Asp with Asn at position 76 in the amino acid sequence of SEQ ID NO. 100.

(2) an amino acid sequence which is introduced with substitution Leu with Met at position 18, substitution of Ser with Thr at position 30, substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48 and substitution of Val with Thr at position 95 in the amino acid sequence of SEQ ID NO. 100.

(3) an amino acid sequence which is introduced with substitution Leu with Met at position 18, substitution of Ser with Thr at position 30, substitution of Val with Ile at position 37, substitution of Ala with Pro at position 40, substitution of Pro with Ala at position 41, substitution of Gly with Ala at position 44, substitution of Leu with Pro at position 45, substitution of Asp with Asn at position 76 and substitution of Val with Thr at position 95 in the amino acid sequence of SEQ ID NO. 100.

(4) an amino acid sequence which is introduced with substitution Leu with Met at position 18, substitution of Ser with Thr at position 30, substitution of Val with Ile at position 37, substitution of Ala with Pro at position 40, substitution of Pro with Ala at position 41, substitution of Gly with Ala at position 44, substitution of Val with Leu at position 48, substitution of Asp with Asn at position 76 and substitution of Val with Thr at position 95 in the amino acid sequence of SEQ ID NO. 100.

(5) an amino acid sequence which is introduced with substitution Leu with Met at position 18, substitution of Ser with Thr at position 30, substitution of Val with Ile at position 37, substitution of Ala with Pro at position 40, substitution of Pro with Ala at position 41, substitution of Leu with Pro at position 45, substitution of Val with Leu at position 48, substitution of Asp with Asn at position 76 and substitution of Val with Thr at position 95 in the amino acid sequence of SEQ ID NO. 100.

(6) an amino acid sequence which is introduced with substitution Leu with Met at position 18, substitution of Ser with Thr at position 30, substitution of Val with Ile at position 37, substitution of Ala with Pro at position 40, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

(7) an amino acid sequence which is introduced with substitution Leu with Met at position 18, substitution of Ser with Thr at position 30, substitution of Val with Ile at position 37, substitution of Pro with Ala at position 41, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

(8) an amino acid sequence which is introduced with substitution Leu with Met at position 18, substitution of Ser with Thr at position 30, substitution of Ala with Pro at position 40, substitution of Pro with Ala at position 41, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

(9) an amino acid sequence which is introduced with substitution Leu with Met at position 18, substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

(10) an amino acid sequence which is introduced with substitution of Ser with Thr at position 30, substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

Specific example of the amino acid sequence of VH introduced with 8 modifications may include the amino acid sequences of the following (1)-(11).

(1) an amino acid sequence which is introduced with substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

(2) an amino acid sequence which is introduced with substitution of Leu with Met at position 18, substitution of Ser with Thr at position 30, substitution of Val with Ile at position 37, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

(3) an amino acid sequence which is introduced with substitution of Leu with Met at position 18, substitution of Ser with Thr at position 30, substitution of Val with Ile at position 37, substitution of Pro with Ala at position 41, substitution of Leu with Pro at position 45, substitution of Val with Leu at position 48, substitution of Asp with Asn at position 76 and substitution of Val with Thr at position 95 in the amino acid sequence of SEQ ID NO. 100.

(4) an amino acid sequence which is introduced with substitution of Leu with Met at position 18, substitution of Ser with Thr at position 30, substitution of Val with Ile at position 37, substitution of Pro with Ala at position 41, substitution of Gly with Ala at position 44, substitution of Leu with Pro at position 45, substitution of Val with Leu at position 48 and substitution of Val with Thr at position 95 in the amino acid sequence of SEQ ID NO. 100.

(5) an amino acid sequence which is introduced with substitution of Leu with Met at position 18, substitution of Ser with Thr at position 30, substitution of Val with Ile at position 37, substitution of Pro with Ala at position 41, substitution of Gly with Ala at position 44, substitution of Leu with Pro at position 45, substitution of Val with Leu at position 48 and substitution of Asp with Asn at position 76 in the amino acid sequence of SEQ ID NO. 100.

(6) an amino acid sequence which is introduced with substitution of Leu with Met at position 18, substitution of Ser with Thr at position 30, substitution of Val with Ile at position 37, substitution of Ala with Pro at position 40, substitution of Leu with Pro at position 45, substitution of Val with Leu at position 48, substitution of Asp with Asn at position 76 and substitution of Val with Thr at position 95 in the amino acid sequence of SEQ ID NO. 100.

(7) an amino acid sequence which is introduced with substitution of Leu with Met at position 18, substitution of Ser with Thr at position 30, substitution of Val with Ile at position 37, substitution of Ala with Pro at position 40, substitution of Gly with Ala at position 44, substitution of Leu with Pro at position 45, substitution of Val with Leu at position 48 and substitution of Val with Thr at position 95 in the amino acid sequence of SEQ ID NO. 100.

(8) an amino acid sequence which is introduced with substitution of Leu with Met at position 18, substitution of Ser with Thr at position 30, substitution of Val with Ile at position 37, substitution of Ala with Pro at position 40, substitution of Gly with Ala at position 44, substitution of Leu with Pro at position 45, substitution of Val with Leu at position 48 and substitution of Asp with Asn at position 76 in the amino acid sequence of SEQ ID NO. 100.

(9) an amino acid sequence which is introduced with substitution of Leu with Met at position 18, substitution of Ser with Thr at position 30, substitution of Val with Ile at position 37, substitution of Ala with Pro at position 40, substitution of Pro with Ala at position 41, substitution of Leu with Pro at position 45, substitution of Val with Leu at position 48 and substitution of Val with Thr at position 95 in the amino acid sequence of SEQ ID NO. 100.

(10) an amino acid sequence which is introduced with substitution of Leu with Met at position 18, substitution of Ser with Thr at position 30, substitution of Val with Ile at position 37, substitution of Ala with Pro at position 40, substitution of Pro with Ala at position 41, substitution of Leu with Pro at position 45, substitution of Val with Leu at position 48 and substitution of Asp with Asn at position 76 in the amino acid sequence of SEQ ID NO. 100.

(11) an amino acid sequence which is introduced with substitution of Leu with Met at position 18, substitution of Ser with Thr at position 30, substitution of Val with Ile at position 37, substitution of Ala with Pro at position 40, substitution of Pro with Ala at position 41, substitution of Gly with Ala at position 44, substitution of Leu with Pro at position 45 and substitution of Val with Leu at position 48 in the amino acid sequence of SEQ ID NO. 100.

Specific example of the amino acid sequence of VH introduced with 7 modifications may include the amino acid sequences of the following (1)-(5).

(1) an amino acid sequence which is introduced with substitution of Ser with Thr at position 30, substitution of Ala with Pro at position 40, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

(2) an amino acid sequence which is introduced with substitution of Ala with Pro at position 40, substitution of Pro with Ala at position 41, substitution of Gly with Ala at position 44, substitution of Leu with Pro at position 45, substitution of Val with Leu at position 48, substitution of Asp with Asn at position 76 and substitution of Val with Thr at position 95 in the amino acid sequence of SEQ ID NO. 100.

(3) an amino acid sequence which is introduced with substitution of Val with Ile at position 37, substitution of Ala with Pro at position 40, substitution of Pro with Ala at position 41, substitution of Leu with Pro at position 45, substitution of Val with Leu at position 48, substitution of Asp with Asn at position 76 and substitution of Val with Thr at position 95 in the amino acid sequence of SEQ ID NO. 100.

(4) an amino acid sequence which is introduced with substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48 and substitution of Val with Thr at position 95 in the amino acid sequence of SEQ ID NO. 100.

(5) an amino acid sequence which is introduced with substitution of Val with Ile at position 37, substitution of Ala with Pro at position 40, substitution of Pro with Ala at position 41, substitution of Gly with Ala at position 44, substitution of Leu with Pro at position 45, substitution of Val with Leu at position 48 and substitution of Asp with Asn at position 76 in the amino acid sequence of SEQ ID NO. 100.

Specific example of the amino acid sequence of VH introduced with 6 modifications may include the amino acid sequences of the following (1)-(6).

(1) an amino acid sequence which is introduced with substitution of Val with Ile at position 37, substitution of Ala with Pro at position 40, substitution of Pro with Ala at position 41, substitution of Leu with Pro at position 45, substitution of Val with Leu at position 48, and substitution of Val with Thr at position 95 in the amino acid sequence of SEQ ID NO. 100.

(2) an amino acid sequence which is introduced with substitution of Ala with Pro at position 40, substitution of Pro with Ala at position 41, substitution of Leu with Pro at position 45, substitution of Val with Leu at position 48, substitution of Asp with Asn at position 76 and substitution of Val with Thr at position 95 in the amino acid sequence of SEQ ID NO. 100.

(3) an amino acid sequence which is introduced with substitution of Ala with Pro at position 40, substitution of Pro with Ala at position 41, substitution of Leu with Pro at position 45, substitution of Val with Leu at position 48, substitution of Asp with Asn at position 76 and substitution of Val with Thr at position 95 in the amino acid sequence of SEQ ID NO. 100.

(4) an amino acid sequence which is introduced with substitution of Val with Ile at position 37, substitution of Ala with Pro at position 40, substitution of Leu with Pro at position 45, substitution of Val with Leu at position 48, substitution of Asp with Asn at position 76 and substitution of Val with Thr at position 95 in the amino acid sequence of SEQ ID NO. 100.

(5) an amino acid sequence which is introduced with substitution of Val with Ile at position 37, substitution of Ala with Pro at position 40, substitution of Pro with Ala at position 41, substitution of Leu with Pro at position 45, substitution of Val with Leu at position 48 and substitution of Val with Thr at position 95 in the amino acid sequence of SEQ ID NO. 100.

(6) an amino acid sequence which is introduced with substitution of Val with Ile at position 37, substitution of Ala with Pro at position 40, substitution of Pro with Ala at position 41, substitution of Gly with Ala at position 44, substitution of Leu with Pro at position 45 and substitution of Val with Leu at position 48 in the amino acid sequence of SEQ ID NO. 100.

Specific example of the amino acid sequence of VH introduced with 5 modifications may include the amino acid sequences of the following (1)-(6).

(1) an amino acid sequence which is introduced with substitution of Val with Ile at position 37, substitution of Ala with Pro at position 40, substitution of Pro with Ala at position 41, substitution of Leu with Pro at position 45, and substitution of Val with Leu at position 48 in the amino acid sequence of SEQ ID NO. 100.

(2) an amino acid sequence which is introduced with substitution of Ala with Pro at position 40, substitution of Pro with Ala at position 41, substitution of Leu with Pro at position 45, substitution of Val with Leu at position 48 and substitution of Val with Thr at position 95 in the amino acid sequence of SEQ ID NO. 100.

(3) an amino acid sequence which is introduced with substitution of Val with Ile at position 37, substitution of Pro with Ala at position 41, substitution of Leu with Pro at position 45, substitution of Val with Leu at position 48 and substitution of Val with Thr at position 95 in the amino acid sequence of SEQ ID NO. 100.

(4) an amino acid sequence which is introduced with substitution of Val with Ile at position 37, substitution of Ala with Pro at position 40, substitution of Leu with Pro at position 45, substitution of Val with Leu at position 48 and substitution of Val with Thr at position 95 in the amino acid sequence of SEQ ID NO. 100.

(5) an amino acid sequence which is introduced with substitution of Val with Ile at position 37, substitution of Ala with Pro at position 40, substitution of Pro with Ala at position 41, substitution of Val with Leu at position 48 and substitution of Val with Thr at position 95 in the amino acid sequence of SEQ ID NO. 100.

(6) an amino acid sequence which is introduced with substitution of Val with Ile at position 37, substitution of Ala with Pro at position 40, substitution of Pro with Ala at position 41, substitution of Leu with Pro at position 45 and substitution of Val with Thr at position 95 in the amino acid sequence of SEQ ID NO. 100.

Specific example of the amino acid sequence of VH introduced with 4 modifications may include the amino acid sequences of the following (1)-(7).

(1) an amino acid sequence which is introduced with substitution of Ala with Pro at position 40, substitution of Pro with Ala at position 41, substitution of Leu with Pro at position 45, and substitution of Val with Thr at position 95 in the amino acid sequence of SEQ ID NO. 100.

(2) an amino acid sequence which is introduced with substitution of Pro with Ala at position 41, substitution of Leu with Pro at position 45, substitution of Val with Leu at position 48 and substitution of Val with Thr at position 95 in the amino acid sequence of SEQ ID NO. 100.

(3) an amino acid sequence which is introduced with substitution of Ala with Pro at position 40, substitution of Pro with Ala at position 41, substitution of Leu with Pro at position 45 and substitution of Val with Thr at position 95 in the amino acid sequence of SEQ ID NO. 100.

(4) an amino acid sequence which is introduced with substitution of Val with Ile at position 37, substitution of Pro with Ala at position 41, substitution of Leu with Pro at position 45 and substitution of Val with Thr at position 95 in the amino acid sequence of SEQ ID NO. 100.

(5) an amino acid sequence which is introduced with substitution of Val with Ile at position 37, substitution of Ala with Pro at position 40, substitution of Leu with Pro at position 45 and substitution of Val with Thr at position 95 in the amino acid sequence of SEQ ID NO. 100.

(6) an amino acid sequence which is introduced with substitution of Val with Ile at position 37, substitution of Ala with Pro at position 40, substitution of Pro with Ala at position 41 and substitution of Val with Thr at position 95 in the amino acid sequence of SEQ ID NO. 100.

(7) an amino acid sequence which is introduced with substitution of Val with Ile at position 37, substitution of Ala with Pro at position 40, substitution of Pro with Ala at position 41 and substitution of Leu with Pro at position 45 in the amino acid sequence of SEQ ID NO. 100.

Specific example of the amino acid sequence of VH introduced with 3 modifications may include the amino acid sequences of the following (1)-(6).

(1) an amino acid sequence which is introduced with substitution of Pro with Ala at position 41, substitution of Leu with Pro at position 45, and substitution of Val with Thr at position 95 in the amino acid sequence of SEQ ID NO. 100.

(2) an amino acid sequence which is introduced with substitution of Val with Ile at position 37, substitution of Leu with Pro at position 45 and substitution of Val with Thr at position 95 in the amino acid sequence of SEQ ID NO. 100.

(3) an amino acid sequence which is introduced with substitution of Ala with Pro at position 40, substitution of Leu with Pro at position 45 and substitution of Val with Thr at position 95 in the amino acid sequence of SEQ ID NO. 100.

(4) an amino acid sequence which is introduced with substitution of Pro with Ala at position 41, substitution of Leu with Pro at position 45 and substitution of Val with Thr at position 95 in the amino acid sequence of SEQ ID NO. 100.

(5) an amino acid sequence which is introduced with substitution of Gly with Ala at position 44, substitution of Leu with Pro at position 45 and substitution of Val with Thr at position 95 in the amino acid sequence of SEQ ID NO. 100.

(6) an amino acid sequence which is introduced with substitution of Leu with Pro at position 45, substitution of Val with Leu at position 48 and substitution of Val with Thr at position 95 in the amino acid sequence of SEQ ID NO. 100.

Specific example of the amino acid sequence of VH introduced with 2 modifications may include the amino acid sequences of the following (1)-(9).

(1) an amino acid sequence which is introduced with substitution of Leu with Met at position 18 and substitution of Val with Thr at position 95 in the amino acid sequence of SEQ ID NO. 100.

(2) an amino acid sequence which is introduced with substitution of Ser with Thr at position 30 and substitution of Val with Thr at position 95 in the amino acid sequence of SEQ ID NO. 100.

(3) an amino acid sequence which is introduced with substitution of Val with Ile at position 37 and substitution of Val with Thr at position 95 in the amino acid sequence of SEQ ID NO. 100.

(4) an amino acid sequence which is introduced with substitution of Ala with Pro at position 40 and substitution of Val with Thr at position 95 in the amino acid sequence of SEQ ID NO. 100.

(5) an amino acid sequence which is introduced with substitution of Pro with Ala at position 41 and substitution of Val with Thr at position 95 in the amino acid sequence of SEQ ID NO. 100.

(6) an amino acid sequence which is introduced with substitution of Gly with Ala at position 44 and substitution of Val with Thr at position 95 in the amino acid sequence of SEQ ID NO. 100.

(7) an amino acid sequence which is introduced with substitution of Leu with Pro at position 45 and substitution of Val with Thr at position 95 in the amino acid sequence of SEQ ID NO. 100.

(8) an amino acid sequence which is introduced with substitution of Val with Leu at position 48 and substitution of Val with Thr at position 95 in the amino acid sequence of SEQ ID NO. 100.

(9) an amino acid sequence which is introduced with substitution of Asp with Asn at position 76 and substitution of Val with Thr at position 95 in the amino acid sequence of SEQ ID NO. 100.

Specific example of the amino acid sequence of VH introduced with 1 modification may include the amino acid sequences of the following (1)-(10).

(1) an amino acid sequence which is introduced with substitution of Leu with Met at position 18 in the amino acid sequence of SEQ ID NO. 100.

(2) an amino acid sequence which is introduced with substitution of Ser with Thr at position 30 in the amino acid sequence of SEQ ID NO. 100.

(3) an amino acid sequence which is introduced with substitution of Val with Ile at position 37 in the amino acid sequence of SEQ ID NO. 100.

(4) an amino acid sequence which is introduced with substitution of Ala with Pro at position 40 in the amino acid sequence of SEQ ID NO. 100.

(5) an amino acid sequence which is introduced with substitution of Pro with Ala at position 41 in the amino acid sequence of SEQ ID NO. 100.

(6) an amino acid sequence which is introduced with substitution of Gly with Ala at position 44 in the amino acid sequence of SEQ ID NO. 100.

(7) an amino acid sequence which is introduced with substitution of Leu with Pro at position 45 in the amino acid sequence of SEQ ID NO. 100.

(8) an amino acid sequence which is introduced with substitution of Val with Leu at position 48 in the amino acid sequence of SEQ ID NO. 100.

(9) an amino acid sequence which is introduced with substitution of Asp with Asn at position 76 in the amino acid sequence of SEQ ID NO. 100.

(10) an amino acid sequence which is introduced with substitution of Val with Thr at position 95 in the amino acid sequence of SEQ ID NO. 100.

Further, VL included in the humanized antibody of the present invention is preferably the following (1)-(4).

(1) VL of antibody comprising an amino acid sequence in which Val at position 15, Ala at position 43, Lys at position 45, Phe at position 71, Thr at position 85 and Tyr at position 87 in the amino acid sequence of SEQ ID NO. 101 are substituted with other amino acid residues.

(2) VL of antibody comprising an amino acid sequence in which Val at position 15, Lys at position 45, Phe at position 71 and Tyr at position 87 in the amino acid sequence of SEQ ID NO. 101 are substituted with other amino acid residues.

(3) VL of antibody comprising an amino acid sequence in which Val at position 15, Phe at position 71 and Tyr at position 87 in the amino acid sequence of SEQ ID NO. 101 are substituted with other amino acid residues.

(4) VL of antibody comprising an amino acid sequence in which Lys at position 45 and Phe at position 71 in the amino acid sequence of SEQ ID NO. 101 are substituted with other amino acid residues.

Example of the amino acid sequence of VL may include an amino acid sequence which is introduced with at least one modification selected from substitution of Val with Leu at position 15, substitution of Ala with Ser at position 43, substitution of Lys with Gln at position 45, substitution of Phe with Tyr at position 71, substitution of Thr with Gly at position 85 and substitution of Tyr with Phe at position 87 in the amino acid sequence of SEQ ID NO. 101.

Specific example of the amino acid sequence of VL introduced with 6 modifications may include the amino acid sequence which is introduced with substitution of Val with Leu at position 15, substitution of Ala with Ser at position 43, substitution of Lys with Gln at position 45, substitution of Phe with Tyr at position 71, substitution of Thr with Gly at position 85 and substitution of Tyr with Phe at position 87 in the amino acid sequence of SEQ ID NO. 101.

Specific example of the amino acid sequence of VL introduced with 5 modifications may include the amino acid sequences of the following (1)-(6).

(1) an amino acid sequence which is introduced with substitution of Ala with Ser at position 43, substitution of Lys with Gln at position 45, substitution of Phe with Tyr at position 71, substitution of Thr with Gly at position 85 and substitution of Tyr with Phe at position 87 in the amino acid sequence of SEQ ID NO. 101.

(2) an amino acid sequence which is introduced with substitution of Val with Leu at position 15, substitution of Lys with Gln at position 45, substitution of Phe with Tyr at position 71, substitution of Thr with Gly at position 85 and substitution of Tyr with Phe at position 87 in the amino acid sequence of SEQ ID NO. 101.

(3) an amino acid sequence which is introduced with substitution of Val with Leu at position 15, substitution of Ala with Ser at position 43, substitution of Phe with Tyr at position 71, substitution of Thr with Gly at position 85 and substitution of Tyr with Phe at position 87 in the amino acid sequence of SEQ ID NO. 101.

(4) an amino acid sequence which is introduced with substitution of Val with Leu at position 15, substitution of Ala with Ser at position 43, substitution of Lys with Gln at position 45, substitution of Thr with Gly at position 85 and substitution of Tyr with Phe at position 87 in the amino acid sequence of SEQ ID NO. 101.

(5) an amino acid sequence which is introduced with substitution of Val with Leu at position 15, substitution of Ala with Ser at position 43, substitution of Lys with Gln at position 45, substitution of Phe with Tyr at position 71 and substitution of Tyr with Phe at position 87 in the amino acid sequence of SEQ ID NO. 101.

(6) an amino acid sequence which is introduced with substitution of Val with Leu at position 15, substitution of Ala with Ser at position 43, substitution of Lys with Gln at position 45, substitution of Phe with Tyr at position 71 and substitution of Thr with Gly at position 85 in the amino acid sequence of SEQ ID NO. 101.

Specific example of the amino acid sequence of VL introduced with 4 modifications may include the amino acid sequences of the following (1)-(6).

(1) an amino acid sequence which is introduced with substitution of Val with Leu at position 15, substitution of Lys with Gln at position 45, substitution of Phe with Tyr at position 71 and substitution of Tyr with Phe at position 87 in the amino acid sequence of SEQ ID NO. 101.

(2) an amino acid sequence which is introduced with substitution of Lys with Gln at position 45, substitution of Phe with Tyr at position 71, substitution of Thr with Gly at position 85 and substitution of Tyr with Phe at position 87 in the amino acid sequence of SEQ ID NO. 101.

(3) an amino acid sequence which is introduced with substitution of Val with Leu at position 15, substitution of Phe with Tyr at position 71, substitution of Thr with Gly at position 85 and substitution of Tyr with Phe at position 87 in the amino acid sequence of SEQ ID NO. 101.

(4) an amino acid sequence which is introduced with substitution of Val with Leu at position 15, substitution of Lys with Gln at position 45, substitution of Thr with Gly at position 85 and substitution of Tyr with Phe at position 87 in the amino acid sequence of SEQ ID NO. 101.

(5) an amino acid sequence which is introduced with substitution of Val with Leu at position 15, substitution of Lys with Gln at position 45, substitution of Phe with Tyr at position 71 and substitution of Tyr with Phe at position 87 in the amino acid sequence of SEQ ID NO. 101.

(6) an amino acid sequence which is introduced with substitution of Val with Leu at position 15, substitution of Lys with Gln at position 45, substitution of Phe with Tyr at position 71 and substitution of Thr with Gly at position 85 in the amino acid sequence of SEQ ID NO. 101.

Specific example of the amino acid sequence of VL introduced with 3 modifications may include the amino acid sequences of the following (1)-(4).

(1) an amino acid sequence which is introduced with substitution of Val with Leu at position 15, substitution of Phe with Tyr at position 71 and substitution of Tyr with Phe at position 87 in the amino acid sequence of SEQ ID NO. 101.

(2) an amino acid sequence which is introduced with substitution of Lys with Gln at position 45, substitution of Phe with Tyr at position 71 and substitution of Tyr with Phe at position 87 in the amino acid sequence of SEQ ID NO. 101.

(3) an amino acid sequence which is introduced with substitution of Val with Leu at position 15, substitution of Lys with Gln at position 45 and substitution of Tyr with Phe at position 87 in the amino acid sequence of SEQ ID NO. 101.

(4) an amino acid sequence which is introduced with substitution of Val with Leu at position 15, substitution of Lys with Gln at position 45 and substitution of Phe with Tyr at position 71 in the amino acid sequence of SEQ ID NO. 101.

Specific example of the amino acid sequence of VL introduced with 2 modifications may include the amino acid sequences of the following (1)-(9).

(1) an amino acid sequence which is introduced with substitution of Lys with Gln at position 45 and substitution of Phe with Tyr at position 71 in the amino acid sequence of SEQ ID NO. 101.

(2) an amino acid sequence which is introduced with substitution of Val with Leu at position 15 and substitution of Phe with Tyr at position 71 in the amino acid sequence of SEQ ID NO. 101.

(3) an amino acid sequence which is introduced with substitution of Ala with Ser at position 43 and substitution of Phe with Tyr at position 71 in the amino acid sequence of SEQ ID NO. 101.

(4) an amino acid sequence which is introduced with substitution of Phe with Tyr at position 71 and substitution of Thr with Gly at position 85 in the amino acid sequence of SEQ ID NO. 101.

(5) an amino acid sequence which is introduced with substitution of Phe with Tyr at position 71 and substitution of Tyr with Phe at position 87 in the amino acid sequence of SEQ ID NO. 101.

(6) an amino acid sequence which is introduced with substitution of Val with Leu at position 15 and substitution of Lys with Gln at position 45 in the amino acid sequence of SEQ ID NO. 101.

(7) an amino acid sequence which is introduced with substitution of Ala with Ser at position 43 and substitution of Lys with Gln at position 45 in the amino acid sequence of SEQ ID NO. 101.

(8) an amino acid sequence which is introduced with substitution of Lys with Gln at position 45 and substitution of Thr with Gly at position 85 in the amino acid sequence of SEQ ID NO. 101.

(9) an amino acid sequence which is introduced with substitution of Lys with Gln at position 45 and substitution of Tyr with Phe at position 87 in the amino acid sequence of SEQ ID NO. 101.

Specific example of the amino acid sequence of VL introduced with 1 modification may include the amino acid sequences of the following (1)-(6).

(1) an amino acid sequence which is introduced with substitution of Val with Leu at position 15 in the amino acid sequence of SEQ ID NO. 101.

(2) an amino acid sequence which is introduced with substitution of Ala with Ser at position 43 in the amino acid sequence of SEQ ID NO. 101.

(3) an amino acid sequence which is introduced with substitution of Lys with Gln at position 45 in the amino acid sequence of SEQ ID NO. 101.

(4) an amino acid sequence which is introduced with substitution of Phe with Tyr at position 71 in the amino acid sequence of SEQ ID NO. 101.

(5) an amino acid sequence which is introduced with substitution of Thr with Gly at position 85 in the amino acid sequence of SEQ ID NO. 101.

(6) an amino acid sequence which is introduced with substitution of Tyr with Phe at position 87 in the amino acid sequence of SEQ ID NO. 101.

Further, specific example of the humanized antibody of the present invention may include a humanized antibody comprising VH of the amino acid sequence of SEQ ID NO. 98 and/or VL of the amino acid sequence of SEQ ID NO. 94, a humanized antibody comprising VH of the amino acid sequence of SEQ ID NO. 98 and/or VL of any one amino acid sequence shown in FIG. 2, a humanized antibody comprising VH of any one amino acid sequence shown in FIG. 1 and/or VL of the amino acid sequence of SEQ ID NO. 94, or the like.

Further, the humanized antibody of the present invention may include a humanized antibody that competes with the monoclonal antibody of the present invention to specifically recognize the amino acid sequence of human FOLR1 or the conformational structure thereof and bind to an epitope that is identical to the epitope on human FOLR1, to which the monoclonal antibody binds.

The human antibody is originally an antibody naturally existing in the human body, and it also includes an antibody obtained from a human antibody phage library or a human antibody-producing transgenic animal, which is prepared based on the recent advanced technologies in genetic engineering, cell engineering and developmental engineering.

The antibody naturally existing in the human body can be obtained, for example, by isolating a human peripheral blood lymphocyte, immortalizing it by infecting with EB virus or the like, and then cloning it, thereby culturing lymphocytes capable of producing the antibody, and the antibody can be purified from the supernatant of the culture.

The human antibody phage library is a library in which antibody fragments such as Fab and scFv are expressed on the phage surface by inserting an antibody gene prepared from a human B cell into a phage gene. A phage expressing an antibody fragment having the desired antigen binding activity on the phage surface can be recovered from the library, using its activity to bind to an antigen-immobilized substrate as the index. Further, the antibody fragment can be converted further into a human antibody molecule comprising two full H chains and two full L chains by genetic engineering technologies.

A human antibody-producing transgenic animal is an animal in which a human antibody gene is integrated into cells. Specifically, the human antibody-producing transgenic animal can be prepared by introducing a human antibody gene into a mouse ES cell, grafting the ES cell into an early stage embryo of mouse and then developing it. A human antibody derived from a human antibody producing transgenic animal can be prepared by obtaining a human antibody producing hybridoma using the hybridoma preparation method which is common for non-human animal, and then culturing the hybridoma to produce and accumulate the human antibody in the culture supernatant.

A monoclonal antibody or antibody fragment thereof in which one or more amino acids are deleted, added, substituted, or inserted in the amino acid sequence constituting the above antibody or antibody fragment and having activity similar to the above antibody or antibody fragment is also included in the monoclonal antibody or antibody fragment of the present invention.

The number of amino acids which are deleted, added substituted, and/or inserted is one or more, and is not specifically limited, but it is within the range where deletion, addition, substitution or insertion is possible by known methods such as the site-directed mutagenesis [Molecular Cloning 2nd Edition, Cold Spring Harbor Laboratory Press (1989), Current Protocols in molecular Biology, John Wiley&Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985)] or the like. For example, the number is preferably 1 to dozens, more preferably 1 to 20, much more preferably 1 to 10, and particularly preferably 1 to 5.

The expression "one or more amino acid residue(s) is/are deleted, added substituted, and/or inserted" in the amino acid sequence of the above antibody means the followings. That is, it means that there is deletion, addition, substitution, or insertion of one or plural amino acid residue(s) in the amino acid sequences of the antibody. Also, the deletion, addition, substitution, or insertion may occur at the same time and the amino acid residue which is deleted, added, substituted, or inserted may be either a natural type or a non-natural type.

Example of the natural type amino acid residue may include L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine or the like.

Preferable examples of mutually substitutable amino acid residues are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine The antibody fragment of the present invention may include Fab, F(ab')$_2$, Fab', a single chain antibody (scFv), a dimeric V region (diabody), a disulfide-stabilized V region (dsFv), a peptide comprising CDR or the like.

A Fab is an antibody fragment having a molecular weight of about 50,000 and having antigen binding activity, in which about a half of the N-terminal side of H chain and the entire L chain are bound together through a disulfide bond among fragments obtained by treating IgG with a protease, papain (cleaved at an amino acid residue at position 224 of the H chain).

The Fab of the present invention can be obtained by treating the monoclonal antibody, which specifically recognizes and binds to the amino acid sequence of human FOLR1 or the conformational structure thereof, with papain. Also, the Fab can be produced by inserting DNA encoding Fab of the antibody into an expression vector for prokaryote or an expression vector for eukaryote, and introducing the vector into a prokaryote or eukaryote to express the Fab.

A F(ab')$_2$ is a fragment having a molecular weight of about 100,000 and having antigen binding activity and including two Fab regions which are bound in the hinge position obtained by digesting the bottom part of two disulfide bonds in the hinge region of IgG with a protease, pepsin.

The F(ab')$_2$ of the present invention can be produced by treating the monoclonal antibody, which specifically recognizes and binds to the amino acid sequence of human FOLR1 or the conformational structure thereof, with pepsin. Also, the F(ab')$_2$ can be produced by binding Fab' described below via a thioether bond or a disulfide bond.

A Fab' is an antibody fragment having a molecular weight of about 50,000 and antigen binding activity, which is obtained by cleaving a disulfide bond at the hinge region of the above F(ab')$_2$. The Fab' of the present invention can be obtained by treating F(ab')$_2$ which specifically recognizes and binds to the amino acid sequence of human FOLR1 of the present invention or the conformational structure thereof with a reducing agent, such as dithiothreitol. Also, the Fab' can be produced by inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (hereinafter referred to as "P") and is an antibody fragment having antigen binding activity.

The scFv of the present invention can be produced by obtaining cDNAs encoding VH and VL of the monoclonal antibody of the present invention which specifically recognizes and binds to the amino acid sequence of human FOLR1 or the conformational structure thereof, constructing DNA encoding scFv, inserting the DNA into an expression vector for prokaryote or an expression vector for eukaryote, and then introducing the expression vector into a prokaryote or eukaryote to express the scFv.

A diabody is an antibody fragment wherein scFv is dimerized, is an antibody fragment having divalent antigen binding activity. In the divalent antigen binding activity, two antigens may be the same or different.

The diabody of the present invention can be produced by obtaining cDNAs encoding VH and VL of the monoclonal antibody which specifically recognizes and binds to the amino acid sequence of human FOLR1 or the conformational structure thereof, constructing DNA encoding scFv so that the length of the amino acid sequence of the peptide linker is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a conformational structure estimation of the antibody in accordance with a known methods [Protein Engineering, 7, 697 (1994)].

The dsFv of the present invention can be produced by obtaining cDNAs encoding VH and VL of the monoclonal antibody which specifically recognizes and binds to the amino acid sequence of human FOLR1 of the present invention or the conformational structure thereof, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one or more regions of CDRs of VH or VL. Peptide comprising plural CDRs can be connected directly or via an appropriate peptide linker.

The peptide comprising CDR of the present invention can be produced by constructing DNA encoding CDRs of VH and VL of the monoclonal antibody which specifically recognizes and binds to the amino acid sequence of human FOLR1 of the present invention or the conformational structure thereof, inserting the DNA into an expression vector for prokaryote or an expression vector for eukaryote, and then introducing the expression vector into a prokaryote or eukaryote to express the peptide. The peptide comprising CDRs can also be produced by a chemical synthesis method such as Fmoc method or tBoc method.

The antibody of the present invention includes an antibody derivative in which the monoclonal antibody or the antibody fragment thereof which specifically recognizes and binds to the amino acid sequence of human FOLR1 of the present invention or the conformational structure thereof is chemically or genetically conjugated to a radioisotope, an agent having a low molecular weight, an agent having a high molecular weight, a protein, a therapeutic antibody or the like.

The antibody derivative of the present invention can be produced by chemically conjugating a radioisotope, an agent having a low molecular weight, an agent having a high molecular weight, an immunostimulator, a protein, a therapeutic antibody or the like to the N-terminal side or C-terminal side of an H chain or an L chain of the monoclonal antibody or the antibody fragment thereof, an appropriate substituent or side chain of the antibody or the antibody fragment, a sugar chain in the monoclonal antibody or the antibody fragment thereof, or the like, which specifically recognizes and binds to the amino acid sequence of human FOLR1 of the present invention or the conformational structure thereof [Kotai Kogaku Nyumon, Chijin Shokan (1994)].

Also, it can be genetically produced by linking a DNA encoding the monoclonal antibody or the antibody fragment thereof which specifically recognizes and binds to the amino acid sequence of human FOLR1 of the present invention or the conformational structure thereof to other DNA encoding a protein or a therapeutic antibody to be conjugated, inserting the DNA into an expression vector, and introducing the expression vector into an appropriate host cell for expression.

Example of the radioisotope may include $^{131}$I, $^{125}$I, $^{90}$Y, $^{64}$Cu, $^{99}$Tc, $^{77}$Lu, $^{211}$At or the like. The radioisotope can be directly conjugated with the antibody by Chloramine-T method or the like. Also, a substance chelating the radioisotope can be conjugated with the antibody. The chelating agent may include 1-isothiocyanatobenzyl-3-methyldiethylene-triaminepentaacetic acid (MX-DTPA) or the like.

Example of the agent having a low molecular weight may include an anti-tumor agent such as an alkylating agent, a nitrosourea agent, a metabolism antagonist, an antibiotic substance, a plant alkaloid, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor [Clinical Oncology, cancer and a chemotherapy company (1996)], a steroid agent such as hydrocortisone and prednisone, a nonsteroidal agent such as aspirin or indomethacin, an immune-regulating agent such as aurothiomalate or penicillamine, an immuno-suppressing agent such as cyclophosphamide or azathioprine, an anti-inflammatory agent such as an anti-histamine agent, for example, chlorpheniramine maleate or clemastine [Inflammation and Anti-inflammation Therapy, Ishiyaku Publishers, Inc. (1982)] or the like.

Examples of the antitumor agent may include amifostine (ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (adriamycin), epirubicin, gemcitabine (gemzar), daunorubicin, procarbazine, mitomycin, cytarabine, etoposide, methotrexate, 5-fluorouracil, vinblastine, vincristine, bleomycin, daunomycin, peplomycin, estramustine, paclitaxel (taxol), docetaxel (Taxotea), aldesleukin, asparaginase, busulfan, carboplatin, oxaliplatin, nedaplatin, cladribine, camptothecin, 10-hydroxy-7-ethylcamptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, tomudex, azacytidine, UFT, oxaloplatin, gefitinib (Iressa), imatinib (STI571), erlotinib, FMS-like-tyrosine kinase 3 (Flt3) inhibitor, Vascular endothelial growth factor receptor (VEGFR) inhibitor, fibroblast growth factor receptor (FGFR) inhibitor, epidermal growth factor receptor (EGFR) inhibitor such as Tarceva or the like, radicicol, 17-allylamino-17-demethoxygeldanamycin, rapamycin, amsacrine, all-trans-retinoic acid, thalidomide, fadrozole, letrozole, exemestane, gold thiomalate, D-penicillamine, bucillamine, azathioprine, mizoribine, cyclosporine, hydrocortisone, bexarotene (targretin), dexamethasone, progestins, estrogens, anastrozole (Arimidex), leupurin, aspirin, indomethacin, celecoxib, chlorpheniramine maleate, chlorpheniramine, clemastine, tretinoin, arsenic, bortezomib, allopurinol, calicheamicin, ibritumomab tiuxetan, targretin, ozogamine, clarithromycin, leucovorin, ifosfamide, ketoconazole, aminoglutethimide, suramin, maytansinoid, or derivatives thereof.

The method for conjugating the low molecular agent with the antibody may include, for example, a method in which the agent and amino groups of the antibody are conjugated through glutaraldehyde, a method in which an amino group of the agent and a carboxyl group of the antibody are conjugated through water-soluble carbodiimide, or the like.

Examples of the agent having a high molecular weight may include polyethylene glycol (hereinafter referred to as PEG), albumin, dextran, polyoxyethylene, styrene-maleic acid copolymer, polyvinylpyrrolidone, pyran copolymer, hydroxypropylmethacrylamide, or the like. By binding these high molecular compounds to an antibody or antibody fragment, the following effects are expected: (1) improvement of stability against various chemical, physical or biological factors, (2) remarkable prolongation of half life in blood, (3) disappearance of immunogenicity, suppression of antibody production, and the like [Bioconjugate Drug, Hirokawa Publishing (1993)]. For example, the method for conjugating PEG to an antibody includes a method in which an antibody is allowed to react with a PEG-modifying reagent [Bioconjugate Drug, Hirokawa Publishing (1993)]. The PEG-modifying reagent includes a modifying agent of e-amino group of lysine (Japanese Patent Publication No. S61-178926), a modifying agent of a carboxyl group of aspartic acid and glutamic acid (Japanese Patent Publication No. S56-23587), a modifying agent of a guanidino group of arginine (Japanese Patent Publication No. H2-117920) or the like.

The immunostimulator may be any natural products known as immunoadjuvants. Specific examples of an agent enhancing immunity include $\beta(1\rightarrow3)$glucan (lentinan, schizophyllan), $\alpha$-galactosylceramide or the like.

Examples of the protein may include a cytokine or a growth factor which activates an immunocompetent cell, such as NK cell, macrophage or neutrophil, a toxic protein, or the like.

Examples of the cytokine or the growth factor may include IFN$\alpha$, IFN$\beta$, IFN$\gamma$, interleukin (hereinafter, referred to as IL)-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF) or the like.

Examples of the toxic protein may include ricin, diphtheria toxin, ONTAK or the like, and also includes a toxic protein in which mutation is introduced into a protein in order to control the toxicity.

Examples of the therapeutic antibody may include an antibody against an antigen in which apoptosis is induced by binding of the antibody, an antigen participating in formation of pathologic state of tumor, an antigen which regulates immunological function and an antigen relating to angiogenesis in the pathologic part.

Examples of the antigen in which apoptosis is induced by binding of the antibody may include cluster of differentiation (hereinafter, referred to as CD) 19, CD20, CD21, CD22, CD23, CD24, CD37, CD53, CD72, CD73, CD74, CDw75, CDw76, CD77, CDw78, CD79a, CD79b, CD80(B7.1), CD81, CD82, CD83, CDw84, CD85, CD86(B7.2), human leukocyte antigen (HLA)-Class II, or Epidermal growth Factor Receptor (EGFR) or the like.

Examples of the antigen participating in formation of pathologic state of tumor or the antigen which regulates immunological function may include CD40, CD40 ligand, B7 family molecule (CD80, CD86, CD274, B7-DC, B7-H2, B7-H3, or B7-H4), ligand of B7 family molecule (CD28, CTLA-4, ICOS, PD-1, or BTLA), OX-40, OX-40 ligand, CD137, tumor necrosis factor (TNF) receptor family molecule (DR4, DR5, TNFR1, or TNFR2), TNF-related apoptosis-inducing ligand receptor (TRAIL) family molecule, receptor family of TRAIL family molecule (TRAIL-R1, TRAIL-R2, TRAIL-R3, or TRAIL-R4), receptor activator of nuclear factor kappa B ligand (RANK), RANK ligand, CD25, folic acid receptor 4, cytokine [IL-1$\alpha$, IL-1$\beta$, IL-4, IL-5, IL-6, IL-10, IL-13, transforming growth factor (TGF)$\beta$, TNF$\alpha$ etc.], receptors of these cytokines, chemokine (SLC, ELC, I-309, TARC, MDC, or CTACK, etc.) and receptors of these chemokines.

Examples of the antigen which inhibits angiogenesis in the pathologic part may include vascular endothelial growth factor (VEGF), angiopoietin, fibroblast growth factor (FGF), EGF, platelet-derived growth factor (PDGF), insulin-like growth factor (IGF), erythropoietin (EPO), TGFβ, IL-8, Ephilin, SDF-1, receptors thereof or the like.

A fusion antibody with a protein or therapeutic antibody can be produced by linking a cDNA encoding the monoclonal antibody or antibody fragment to a cDNA encoding the protein, constructing a DNA encoding the fusion antibody, inserting the DNA into an expression vector for prokaryote or eukaryote, and then introducing the expression vector into a prokaryote or eukaryote to express the fusion antibody.

If the antibody derivative of the present invention is used for the immunological detection or measurement of human FOLR1 or for the diagnosis of human FOLR1 positive cell-associated diseases, a label used in a common immunological detection or measurement method may be selected as the agent for bound to the N-terminal side or C-terminal side of an H chain or an L chain of the monoclonal antibody or the antibody fragment thereof, an appropriate substituent or side chain of the antibody or the antibody fragment, a sugar chain in the monoclonal antibody or the antibody fragment thereof, or the like, which specifically recognizes and binds to the amino acid sequence of human FOLR1 or the conformational structure thereof.

Examples of the label may include enzymes such as alkaline phosphatase, peroxidase or luciferase, luminescent materials such as acridinium ester or lophine, fluorescent materials such as fluorescein isothiocyanate (FITC) or tetramethyl rhodamine isothiocyanate (RITC), or the like.

Further, the present invention relates to a therapeutic agent for diseases associated with FOLR1-positive cells, comprising the monoclonal antibody of the present invention or the antibody fragment thereof as an active ingredient.

The diseases associated with FOLR1-positive cells may be any disease as long as it is associated with FOLR1-expressing cells, and for example, cancer.

Examples of the cancer may include blood cancer, breast cancer, uterine cancer, colorectal cancer, esophageal cancer, stomach cancer, ovarian cancer, lung cancer, renal cancer, rectal cancer, thyroid cancer, uterine cervix cancer, small intestinal cancer, prostate cancer, mesothelioma and pancreatic cancer, and preferably, ovarian cancer, renal cancer, lung cancer, breast cancer, pancreatic cancer, or mesothelioma.

The therapeutic agent of the present invention comprises the above described monoclonal antibody of the present invention or the antibody fragment thereof, or the derivatives thereof as an active ingredient.

The therapeutic agent comprising the antibody of the present invention or the antibody fragment thereof, or the derivatives thereof may include only the antibody or antibody fragment thereof, or derivative thereof as an active ingredient. It is generally preferred that the therapeutic agent is prepared as a pharmaceutical preparation produced by mixing it with one or more pharmaceutically acceptable carriers according to an appropriate method well known in the technical field of pharmaceutics.

It is preferred to use the route that is most effective for the treatment as an administration route. Examples thereof may include oral administration and parenteral administration, such as buccal, tracheal, intrarectal, subcutaneous, intramuscular or intravenous administration, and preferably, intravenous administration.

Examples of the administration form may include spray, capsules, tablets, powder, granules, syrup, emulsion, suppository, injection, ointment, tape, or the like.

Although the dose or the frequency of administration varies depending on the desired therapeutic effect, administration method, treating period, age, body weight and the like, it is usually 10 μg/kg to 10 mg/kg per day and per adult.

The therapeutic agent of the present invention may be used singly, or in combinations with at least one of the above described radioisotope, agent having a low molecular weight, agent having a high molecular weight, protein, and therapeutic antibody. With respect to the combination method of the therapeutic agent of the present invention with other therapeutic agents, the therapeutic agent to be used in combination with the therapeutic agent of the present invention may be administered together with the therapeutic agent of the present invention simultaneously or sequentially.

Further, the present invention relates to an immunological detection or measurement method of human FOLR1 or human FOLR1-positive cells using the monoclonal antibody of the present invention or the antibody fragment thereof.

In the present invention, the immunological detection or measurement method is a method of detecting or measuring an antibody amount or an antigen amount using a labeled antigen or antibody. Specific examples of the immunological detection or measurement method of FOLR1 may include a detection or measurement method of FOLR1 or FOLR1-positive cells by a radioactive substance-labeled immunoantibody method (RIA), an enzyme immunoassay (EIA or ELISA), a fluorescent immunoassay (FIA), a luminescent immunoassay, Western blotting, an immunoprecipitation method, a fluorescent cell staining method, immunohistochemistry, a physicochemical method or the like.

Further, the present invention relates to a method for diagnosing diseases associated with human FOLR1-positive cells, including detection or measurement of human FOLR1-positive cells using the monoclonal antibody of the present invention or the antibody fragment thereof.

For the detection or measurement of the FOLR1-positive cells, known immunological detection methods above described can be used. An immunoprecipitation method, a fluorescent cell staining method, immunohistochemistry or the like are preferably used. Also, a fluorescent antibody staining method using FMAT 8100 HTS system (manufactured by Applied Biosystem) or the like can be used.

In the present invention, the living body sample to be used for detecting or measuring FOLR1-positive cells is not particularly limited, as long as it has a possibility of containing a cell expressing FOLR1, such as tissue cells, blood, blood plasma, serum, pancreatic fluid, urine, fecal matter, tissue fluid, culture fluid or the like.

In the present invention, example of the method for diagnosing diseases associated with human FOLR1-positive cells may include a method in which the number of FOLR1-positive cells observed in the living body sample to be subjected to detection or measurement is used as an index for diagnosing diseases associated with human FOLR1-positive cells.

The present invention relates to a diagnostic agent for diseases associated with human FOLR1-positive cells, comprising the monoclonal antibody of the present invention or the antibody fragment thereof as an active ingredient.

The diagnostic agent of the present invention comprises the above described monoclonal antibody of the present invention or the antibody fragment thereof, or the derivatives thereof as an active ingredient.

The diagnostic agent of the present invention may include a reagent for carrying out an antigen-antibody reaction or a reagent for detection of the reaction, depending on the desired diagnostic method. The reagent for carrying out the antigen-antibody reaction may include a buffer, a salt or the like. The reagent for detection may include a reagent generally used for the immunological detection or measurement method, such as a labeled secondary antibody which recognizes the monoclonal antibody, antibody fragment thereof or derivatives thereof or a substrate corresponding to the labeling.

Hereinafter, a method for producing the antibody of the present invention, a method for treating the disease and a method for diagnosing the disease of the present invention will be described in detail.

1. Production Method of Monoclonal Antibody (1) Preparation of Antigen

FOLR1 or a cell expressing FOLR1 as an antigen can be obtained by introducing an expression vector comprising cDNA encoding a full length of FOLR1 or a partial length thereof into *Escherichia coli*, yeast, an insect cell, an animal cell or the like. In addition, FOLR1 can be purified and obtained from various human tumor cultured cell lines, human tissue or the like which express a large amount of FOLR1. The tumor cultured cell, the tissue or the like can be allowed to simply use as antigens. Furthermore, a synthetic peptide having a partial sequence of FOLR1 can be prepared by a chemical synthesis method such as Fmoc method or tBoc method and used as an antigen.

FOLR1 used in the present invention can be produced, for example, by expressing a DNA encoding FOLR1 in a host cell using a method described in Molecular Cloning, A Laboratory Manual, Second Edition, Cold Spring Harbor Laboratory Press (1989) or Current Protocols in molecular Biology, John Wiley&Sons (1987-1997) or the like according to the following method.

First, an expression vector is prepared by inserting a full length cDNA comprising the region encoding FOLR1 into downstream of a promoter of an appropriate expression vector. A DNA fragment having an appropriate length comprising a region encoding the polypeptide which is prepared based on the full length cDNA can be also used instead of the above full length cDNA. Next, a transformant producing the polypeptide can be obtained by introducing the expression vector into a host cell suitable for the expression vector.

As the expression vector, any one can be used, as long as it can replicate autonomously in the host cell to be used or it can be integrated into a chromosome and also includes an appropriate promoter at such a position that the DNA encoding the polypeptide can be transcribed.

As the host cell, any one can be used, as long as it can express the objective gene, such as a microorganism which belongs to the genera *Escherichia*, such as *Escherichia coli*, yeast, an insect cell, an animal cell or the like.

When a prokaryote such as *Escherichia coli* is used as the host cell, it is preferred to use a vector that is autonomously replicable in the prokaryote and includes a promoter, a ribosome binding sequence, the DNA encoding FOLR1 and a transcription termination sequence as the expression vector. The above expression vector is not necessary to have a transcription termination sequence, but a transcription termination sequence is preferably set just below the structural gene. The expression vector may further include a gene regulating the promoter.

As the above expression vector, it is preferred to use a plasmid in which the space between Shine-Dalgarno sequence (also called SD sequence), which is the ribosome binding sequence, and the initiation codon is adjusted to an appropriate distance (for example, 6 to 18 nucleotides).

Furthermore, the nucleotide sequence of the DNA encoding FOLR1 can be substituted with another base so as to be a suitable codon for expressing in a host cell, thereby improving the productivity of the desired FOLR1.

Any expression vector can be used as the expression vector, as long as it can function in the host cell to be used. Examples thereof may include pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Patent Publication No. S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Patent Publication No. S60-221091], pGKA2 [prepared from *Escherichia coli* IGKA2 (FERM BP6798), Japanese Patent Publication No. S60-221091], pTerm2 (U.S. Pat. No. 4,686,191, U.S. Pat. No. 4,939,094, U.S. Pat. No. 5,160,735), pSupex, pUB110, pTP5, pC194, pEG400 [J. Bacteriol., 172, 2392 (1990)], pGEX (manufactured by Pharmacia), pET system (manufactured by Novagen), pME18SFL3 or the like.

Any promoter can be used, as long as it can function in the host cell to be used. Examples thereof may include promoters derived from *Escherichia coli*, phage or the like, such as trp promoter (Ptrp), lac promoter, PL promoter, PR promoter, T7 promoter or the like. Also, artificially designed and modified promoters, such as a tandem promoter in which two Ptrp are linked in tandem, tac promoter, lacT7 promoter, letl promoter or the like, can be used.

Examples of the host cell may include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* DH5α or the like.

Any method of introducing the expression vector into the host cell can be used, as long as it is a method for introducing DNA into the host cell to be used, and examples thereof may include a method using calcium ions [Proc. Natl. Acad. Sci. USA, 69, 2110 (1972), Gene, 17, 107 (1982), Molecular&General Genetics, 168, 111 (1979)] or the like.

When an animal cell is used as the host cell, any expression vector can be used, as long as it can function in the animal cell. Examples thereof may include pcDNAI, pcDM8 (manufactured by Funakoshi), pAGE107 [Japanese Patent Publication No. H3-22979; Cytotechnology, 3, 133 (1990)], pAS3-3 (Japanese Patent Publication No. 112-227075), pCDM8 [Nature, 329, 840, (1987)], pcDNAI/Amp (manufactured by Invitrogen), pcDNA3.1 (manufactured by Invitrogen), pREP4 (manufactured by Invitrogen), pAGE103 [J. Biochemistry, 101, 1307 (1987)], pAGE210, pME18SFL3, pKANTEX93 (WO 97/10354) or the like.

Any promoter can be used, as long as it can function in an animal cell. Examples thereof may include a promoter of immediate early (IE) gene of cytomegalovirus (CMV), SV40 early promoter, a promoter of retrovirus, a metallothionein promoter, a heat shock promoter, SRα promoter, Molony murine leukemia virus promoter or enhancer, or the like. Also, the enhancer of the IE gene of human CMV can be used together with the promoter.

Examples of the host cell may include human leukemia Namalwa cell, monkey COS cell, Chinese hamster ovary (CHO) cell (Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc.

Natl. Acad. Sci. USA, 60, 1275 (1968); Cell, 6, 121 (1975); Molecular Cellgenetics, Appendix I, II (pp. 883-900)), CHO/DG44, CHO-K1 (ATCC NO. CCL-61), DUkXB11 (ATCC NO. CCL-9096), Pro-5 (ATCC NO. CCL-1781), CHO-S (Life Technologies, Cat#11619), Pro-3, rat myeloma cell YB2/3HL.P2.G11.16Ag.20 (also called YB2/0), mouse myeloma cell NS0, mouse myeloma cell SP2/0-Ag14, Syrian hamster cell BHK or HBT5637 (Japanese Patent Publication No. S63-000299) or the like.

Any method of introducing the expression vector into the host cells can be used, as long as it is a method for introducing DNA into an animal cell, and examples thereof may include electroporation [Cytotechnology, 3, 133 (1990)], a calcium phosphate method (Japanese Patent Publication No. H2-227075), a lipofection method [Proc. Natl. Acad. Sci. USA, 84, 7413 (1987)], or the like.

FOLR1 can be produced by culturing the transformant derived from a microorganism or an animal cell having an expression vector including the DNA encoding FOLR1 in a medium to form and accumulate FOLR1 in the culture, and recovering it from the culture. The method for culturing the transformant in the medium may be carried out according to the typical method used in culturing hosts.

When FOLR1 is expressed in a cell derived from eukaryote, FOLR1 to which sugars or sugar chains bind can be obtained.

When a microorganism transformed with an expression vector containing an inducible promoter is cultured, an inducer can be added to the medium, if necessary. For example, isopropyl-β-D-thiogalactopyranoside or the like can be added to the medium when a microorganism transformed with an expression vector using lac promoter is cultured. In addition, indoleacrylic acid or the like can be added to the medium when a microorganism transformed with an expression vector using trp promoter is cultured.

As the medium for culturing a transformant obtained using an animal cell as the host cell, examples of the medium may include generally used RPMI 1640 medium [The Journal of the American Medical Association, 199, 519 (1967)], Eagle's MEM [Science, 122, 501 (1952)], Dulbecco's modified MEM [Virology, 8, 396 (1959)] and 199 medium [Proc. Soc. Exp. Biol. Med., 73, 1 (1950)], Iscoove's modified Dulbecco's medium (IMDM), the media to which fetal vobine serum (FBS), etc. is added, or the like. The culture is generally carried out at a pH of 6 to 8 and 30 to 40° C. in the presence of 5% $CO_2$ for 1 to 7 days. If necessary, an antibiotic such as kanamycin or penicillin can be added to the medium during the culture.

Regarding the expression method of the gene encoding FOLR1, in addition to direct expression, secretory production or fusion protein expression [Molecular Cloning, A Laboratory Manual, Second Edition, Cold Spring Harbor Laboratory Press (1989)] can be used.

The method for producing FOLR1 includes a method of intracellular expression in a host cell, a method of extracellular secretion from a host cell, a method of producing it on a host cell outer membrane. The appropriate method can be selected by changing the host cell used and the structure of the FOLR1 produced.

When the FOLR1 is produced in a host cell or on a host cell outer membrane, FOLR1 can be positively secreted extracellularly in accordance with the method of Paulson et al. [J. Biol. Chem., 264, 17619 (1989)], the method of Lowe et al. [Proc. Natl. Acad. Sci. USA, 86, 8227 (1989), Genes Develop., 4, 1288 (1990)], the methods described in Japanese Patent Publication No. H5-336963 and WO 94/23021, or the like.

Also, the production amount of FOLR1 can be increased by using a gene amplification system using a dihydrofolate reductase gene (Japanese Patent Publication No. H2-227075).

The resulting FOLR1 can be isolated and purified, for example, as follows.

When FOLR1 is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract.

The cell-free extract is centrifuged to obtain a supernatant, and a purified preparation can be obtained from the supernatant using a general protein isolation and purification technologies, namely, solvent extraction, salting out with ammonium sulfate etc., desalting, precipitation with an organic solvent, anion exchange chromatography using a resin such as diethylaminoethyl (DEAE)-sepharose, DIAION HPA-75 (manufactured by Mitsubishi Chemical), cation exchange chromatography using a resin such as S-Sepharose FF (manufactured by Pharmacia), hydrophobic chromatography using a resin such as butyl-Sepharose or phenyl-Sepharose, gel filtration using a molecular sieve, affinity chromatography, chromatofocusing, electrophoresis such as isoelectric focusing electrophoresis or the like, singly or in combination.

When FOLR1 is expressed intracellularly by forming an undissolved body, the cells are recovered, disrupted and centrifuged in the same manner as above, and the undissolved body of FOLR1 is recovered as a precipitation fraction. The recovered undissolved body of FOLR1 is solubilized with a protein denaturing agent. The FOLR1 is made into a normal conformational structure by diluting or dialyzing the solubilized solution, and then a purified preparation of the polypeptide is obtained by the same isolation purification method as above.

When FOLR1 or the derivative such as a glycosylated product is secreted extracellularly, FOLR1 or the derivative such as a glycosylated product can be recovered from the culture supernatant. The culture is treated by a method such as centrifugation in the same manner as above to obtain a soluble fraction, a purified preparation can be obtained from the soluble fraction by the same isolation purification method as above.

Also, FOLR1 used in the present invention can be produced by a chemical synthesis method, such as Fmoc method or tBoc method. Also, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(2) Immunization of Animal and Preparation of Antibody-Producing Cell for Fusion A mouse, rat or hamster 3 to 20 weeks old is immunized with the antigen prepared in the above (1), and antibody-producing cells are collected from the spleen, lymph node or peripheral blood of the animal. Also, when the increase of a sufficient antibody titer in the above animal is not recognized due to low immunogenicity, a FOLR1 knockout mouse may be used as an animal to be immunized.

The immunization is carried out by administering the antigen to the animal through subcutaneous, intravenous or intraperitoneal injection together with an appropriate adjuvant, for example, complete Freund's adjuvant, combination of aluminum hydroxide gel with pertussis vaccine, or the like. When the antigen is a partial peptide, a conjugate is produced with a carrier protein such as BSA (bovine serum albumin), KLH (keyhole limpet hemocyanin) or the like, which is used as the immunogen.

The administration of the antigen is carried out 5 to 10 times every one week or every two weeks after the first administration. On the $3^{rd}$ to $7^{th}$ day after each administration, a blood sample is collected from the venous plexus in ocular fundus, and the antibody titer of the serum is tested by enzyme immunoassay [Antibodies—A Laboratory Manual, Cold Spring Harbor Laboratory (1988)] or the like. An animal showing a sufficient antibody titer in their sera against the antigen used for the immunization is used as the supply source of antibody-producing cells for fusion.

Three to seven days after final administration of the antigen, tissue containing the antibody-producing cells such as the spleen from the immunized animal is excised to collect the antibody-producing cells. When the spleen cells are used, the spleen is cut out and loosened, followed by centrifugation. Then, antibody-producing cells for fusion are obtained by removing erythrocytes.

(3) Preparation of Myeloma Cell

An established cell line obtained from mouse is used as myeloma cells. Examples thereof may include 8-azaguanine-resistant mouse (derived from BALB/c) myeloma cell line P3-X63Ag8-U1 (P3-U1) [Current Topics in Microbiology and Immunology, 18, 1 (1978)], P3-NS1/1Ag41 (NS-1) [European J. Immunology, 6, 511 (1976)], SP2/0-Ag14 (SP-2) [Nature, 276, 269 (1978)], P3-X63-Ag8653(653) [J. Immunology, 123, 1548 (1979)], P3-X63-Ag8 (X63) [Nature, 256, 495 (1975)] or the like.

The myeloma cells are subcultured in a normal medium [a medium prepared by adding glutamine, 2-mercaptoethanol, gentamicin, FBS and 8-azaguanine to RPMI-1640 medium] and they are subcultured in the normal medium 3 or 4 days before cell fusion to ensure the cell number of $2 \times 10^7$ or more on the day for fusion.

(4) Cell Fusion and Preparation of Hybridoma for Producing Monoclonal Antibody

The antibody-producing cells for fusion obtained by the above (2) and myeloma cells obtained by the above (3) are sufficiently washed with a Minimum Essential Medium (MEM) or PBS (1.83 g of disodium phosphate, 0.21 g of potassium phosphate, 7.65 g of sodium chloride, 1 liter of distilled water, pH 7.2) and mixed to give a ratio of the antibody-producing cells:the myeloma cells for fusion=5 to 10:1, followed by centrifugation. Then, the supernatant is discarded.

The precipitated cell group is sufficiently loosened, and then the mixture of polyethylene glycol-1000 (PEG-1000), MEM and dimethylsulfoxide is added under stirring at 37° C. In addition, 1 to 2 mL of MEM is added several times every one or two minutes, and MEM is added to give a total amount of 50 mL. After centrifugation, the supernatant is discarded. After the precipitated cell group are gently loosen, the cells are gently suspended in HAT medium [a medium prepared by adding hypoxanthine, thymidine and aminopterin to the normal medium]. The suspension is cultured in a 5% $CO_2$ incubator for 7 to 14 days at 37° C.

After culture, a portion of the culture supernatant is sampled and a cell group which is reactive to an antigen containing FOLR1 and is not reactive to an antigen containing no FOLR1 is selected by a selecting method of hybridoma such as binding assay as described below. Then, cloning is carried out twice by a limiting dilution method [First, HT medium (HAT medium from which aminopterin is removed) is used, and second, the normal medium is used], and a hybridoma which shows a stably high antibody titer is selected as the monoclonal antibody-producing hybridoma.

(5) Preparation of Purified Monoclonal Antibody

The hybridomas producing a monoclonal antibody obtained by the above (4) are administered by intraperitoneal injection into 8- to 10-week-old mice or nude mice treated with pristane (0.5 mL of 2,6,10,14-tetramethylpentadecane (pristane) is intraperitoneally administered, followed by feeding for 2 weeks). The hybridoma develops ascites tumor in 10 to 21 days. The ascitic fluid is collected from the mice, centrifuged to remove solids, subjected to salting out with 40 to 50% ammonium sulfate and then precipitated by caprylic acid, passed through a DEAE-Sepharose column, a protein A column or a gel filtration column to collect an IgG or IgM fraction as a purified monoclonal antibody.

Furthermore, a monoclonal antibody-producing hybridoma obtained by the above (4) is cultured in RPMI1640 medium containing 10% FBS or the like and the supernatant is removed by centrifugation. They are suspended in Hybridoma SFM and cultured for 3 to 7 days. The purified monoclonal antibody can be obtained by centrifuging the obtained cell suspension, followed by purifying the resulting supernatant with Protein A column or Protein G column to collect the IgG fractions. Meanwhile, 5% DIGO GF21 may be added to the Hybridoma SFM.

The subclass of the antibody can be determined using a subclass typing kit by enzyme immunoassay. The amount of the protein can be determined by the Lowry method or from the absorbance at 280 nm.

(6) Selection of Monoclonal Antibody

Selection of monoclonal antibody is carried out by the following binding assay using an enzyme immunoassay method and kinetic analysis with Biacore.

(6-a) Binding Assay

As the antigen, a gene-introduced cell or a recombinant protein obtained by introducing an expression vector comprising a cDNA encoding FOLR1 obtained in (1) into *Escherichia coli*, yeast, an insect cell, an animal cell or the like, or a purified polypeptide or partial peptide obtained from a human tissue is used. When the antigen is a partial peptide, a conjugate is prepared with a carrier protein such as BSA or KLH and is used.

After making these antigens into a solid layer by dispensing the antigens in a 96-well plate, a substance to be tested such as serum, a culture supernatant of a hybridoma or a purified monoclonal antibody is dispensed therein as the primary antibody and allowed to react. After thoroughly washing with PBS or PBS-Tween, an anti-immunoglobulin antibody labeled with biotin, an enzyme, a chemiluminescent material, a radiation compound or the like is dispensed therein as the secondary antibody and allowed to react. After thoroughly washing with PBS-Tween, the reaction is carried out according to the label of the secondary antibody to select a monoclonal antibody which specifically reacts with the immunogen.

In addition, the monoclonal antibody of the present invention that competes with the anti-FOLR1 monoclonal antibody and binds to FOLR1 can be obtained by adding a subject antibody to the above binding assay system to allow to react. Namely, a monoclonal antibody which competes with the obtained monoclonal antibody in the binding of an amino acid sequence of FOLR1 or a conformational structure thereof can be obtained by screening an antibody which inhibits the binding of the monoclonal antibody upon adding the subject antibody.

Furthermore, an antibody which binds to the same epitope as the epitope recognized by the monoclonal antibody of the present invention that binds to the amino acid sequence of FOLR1 or the conformational structure thereof can be obtained by identifying an epitope of the antibody obtained by the above binding assay system, preparing a partial synthetic peptide of the epitope or a synthetic peptide which mimics the conformational structure of the epitope, followed by immunization.

(6-b) Kinetic Analysis with Biacore

The kinetics between an antigen and a test substance is measured using Biacore T100, and then the results are analyzed using analysis software accompanied with the apparatus. After anti-mouse IgG antibody is immobilized onto to a CM 5 sensor chip by an amine coupling method, a test substance such as a culture supernatant of a hybridoma, a purified monoclonal antibody or the like is allowed to flow and bind at an appropriate amount, and an antigen at various known concentrations is further allowed to flow. Then, the association and dissociation are measured. Using the obtained data and the software accompanied with the apparatus, the kinetics analysis is carried out using the 1:1 binding model to obtain various parameters.

Otherwise, after human FOLR1 is immobilized onto the sensor chip, for example, by an amine coupling method, a purified monoclonal antibody is allowed to flow at various known concentrations followed by measuring the association and dissociation. Using the obtained data and the software accompanied with the apparatus, the kinetics analysis is carried out using a bivalent binding model to obtain various parameters.

2. Preparation of Recombinant Antibody

As preparation examples of recombinant antibodies, methods for producing a human chimeric antibody and a human CDR-grafted antibody are shown below.

(1) Construction of Vector for Recombinant Antibody Expression

A vector for recombinant antibody expression is an expression vector for animal cell into which DNAs encoding CH and CL of a human antibody have been inserted, and can be constructed by cloning each of DNAs encoding CH and CL of a human antibody into an expression vector for animal cell.

As the C region of a human antibody, CH and CL of any human antibody can be used. Examples thereof include CH of γ1 subclass and CL of κ class of human antibody, or the like. As the DNAs encoding CH and CL of a human antibody, the cDNA can be generally used and a chromosomal DNA composed of an exon and an intron can be also used.

As the expression vector for animal cell, any expression vector can be used, as long as a gene encoding the C region of a human antibody can be inserted thereinto and expressed therein. Examples thereof may include pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)] or the like.

Examples of a promoter and an enhancer used for an expression vector for animal cell include an SV40 early promoter [J. Biochem., 101, 1307 (1987)], a Moloney mouse leukemia virus LTR [Biochem. Biophys. Res. Commun., 149, 960 (1987)], an immunoglobulin H chain promoter [Cell, 41, 479 (1985)], an enhancer [Cell, 33, 717 (1983)] or the like.

As the vector for recombinant antibody expression, a type of the vector for recombinant antibody expression in which both of antibody H and L chains exist on the same vector (tandem type) [J. Immunol. Methods, 167, 271 (1994)] may be used, in terms of easiness of construction of a vector for recombinant antibody expression, easiness of introduction into animal cells, and balance between the expression levels of antibody H and L chains in animal cells, and a type in which antibody H and L chains exist on separate vectors may be also used. Examples of the tandem type of the vector for recombinant antibody expression include pKANTEX93 (WO 97/10354), pEE18 [Hybridoma, 17, 559 (1998)], or the like.

(2) Acquisition of cDNA Encoding V Region of Antibody Derived from Non-Human Animal and Analysis of Amino Acid Sequence Acquisition of cDNAs encoding VH and VL of a non-human antibody and analysis of amino acid sequence can be carried out as follows.

mRNA is extracted from hybridoma cells producing a non-human antibody to synthesize cDNA. The synthesized cDNA is cloned into a vector such as a phage or a plasmid, to prepare a cDNA library.

Each of a recombinant phage or recombinant plasmid comprising cDNA encoding VH or VL is isolated from the library using DNA encoding the C region or V region of a mouse antibody as the probe. The full length of the nucleotide sequences of VH and VL of a mouse antibody of interest on the recombinant phage or recombinant plasmid are determined, and the full length of the amino acid sequences of VH and VL are deduced from the nucleotide sequences, respectively.

Examples of the non-human animal for preparing a hybridoma cell which produces a non-human antibody include mouse, rat, hamster, rabbit or the like. Any animals can be used as long as a hybridoma cell can be produced therefrom.

Total RNA can be prepared from a hybridoma cell using a guanidine thiocyanate-cesium trifluoroacetate method [Methods in Enzymol., 154, 3 (1987)], or a kit such as RNA easy kit (manufactured by Qiagen) or the like.

mRNA can be prepared from total RNA using an oligo (dT) immobilized cellulose column method [Molecular Cloning, A Laboratory Manual, Second Edition, Cold Spring Harbor Laboratory Press (1989)], a method using a kit such as Oligo-dT30 <Super> mRNA Purification Kit (manufactured by Takara Bio) or the like. In addition, mRNA can be prepared from hybridoma cells using a kit such as a Fast Track mRNA Isolation kit (manufactured by Invitrogen), a QuickPrep mRNA Purification Kit (manufactured by Pharmacia) or the like.

Examples of the method for synthesizing cDNA and preparing a cDNA library include known methods [Molecular Cloning, A Laboratory Manual, Second Edition, Cold Spring Harbor Laboratory Press (1989), Current Protocols in Molecular Biology, Supplement 1, John Wiley & Sons (1987-1997)], a method using a kit such as a Super Script Plasmid System for cDNA Synthesis and Plasmid Cloning (manufactured by Invitrogen), a ZAP-cDNA Synthesis Kit (manufactured by Stratagene), etc., or the like.

The vector, into which cDNA synthesized using mRNA extracted from a hybridoma cell as the template is inserted for preparing a cDNA library, may be any vector, as long as the cDNA can be inserted thereto. Examples thereof include ZAP ExPress [Strategies, 5, 58 (1992)], pBluescript II SK(+) [Nucleic Acids Research, 17, 9494 (1989)], λZAPII (manufactured by Stratagene), λgt10 and λgt11 [DNA Cloning: A Practical Approach, I, 49 (1985)], Lambda BlueMid (manufactured by Clontech), λExCell, pT7T3-18U (manufactured by Pharmacia), pcD2 [Mol. Cell. Biol., 3, 280 (1983)], pUC18 [Gene, 33, 103 (1985)], or the like.

Any *Escherichia coli* for introducing the cDNA library constructed by a phage or plasmid vector may be used, as long as the cDNA library can be introduced, expressed and maintained. Examples thereof include XL1-Blue MRF [Strategies, 5, 81 (1992)], C600 [Genetics, 39, 440 (1954)], Y1088 and Y1090 [Science, 222: 778 (1983)], NM522 [J. Mol. Biol., 166, 1 (1983)], K802 [J. Mol. Biol., 16, 118 (1966)], JM105 [Gene, 38, 275 (1985)], or the like.

A colony hybridization or plaque hybridization method using an isotope- or fluorescence-labeled probe [Molecular Cloning, A Laboratory Manual, Second Edition, Cold Spring Harbor Laboratory Press (1989)] may be used for selecting cDNA clones encoding VH or VL of a non-human antibody from the cDNA library, or the like.

Also, the cDNA encoding VH or VL can be prepared through polymerase chain reaction method [hereinafter, referred to as PCR method; Molecular Cloning, A Laboratory Manual, Second Edition, Cold Spring Harbor Laboratory Press (1989), Current Protocols in molecular Biology, Supplement 1, John Wiley&Sons (1987-1997)] by preparing primers and using cDNA prepared from mRNA or a cDNA library as the template.

The nucleotide sequence of the cDNA can be determined by digesting the cDNA selected with appropriate restriction enzymes or the like, cloning them into a plasmid such as pBluescript SK(−) (manufactured by Stratagene), carrying out a sequence analyzing method usually used. For example, the sequence analyzing method is carried out by using an automatic nucleotide sequence analyzer such as ABI PRISM3700 (manufactured by PE Biosystems) or A.L.F. DNA sequencer (manufactured by Pharmacia) after reaction such as the dideoxy method [Proc. Natl. Acad. Sci. USA, 74, 5463 (1977)].

Whether the obtained cDNAs encode the full amino acid sequences of VH and VL of the antibody comprising a secretory signal sequence is confirmed by estimating the full amino acid sequences of VH and VL from the determined nucleotide sequence and comparing them with the full amino acid sequences of VH and VL of known antibodies [A.L.F. DNA, US Dept. Health and Human Services (1991)].

With respect to the full amino acid sequences of VH and VL of the antibody comprising a secretory signal sequence, the length of the secretory signal sequence and N-terminal amino acid sequence can be estimated by comparing them with the full amino acid sequences of VH and VL of known antibodies [A.L.F. DNA, US Dept. Health and Human Services (1991)], and furthermore the subgroup to which they belong can be determined. In addition, the amino acid sequence of each CDR of VH and VL can be determined by comparing them with the amino acid sequences of VH and VL of known antibodies [A.L.F. DNA sequencer, US Dept. Health and Human Services (1991)].

Moreover, the novelty of the full amino acid sequence of VH and VL can be examined by carrying out a homology search in any database, for example, SWISS-PROT, PIR-Protein or the like using the obtained full amino acid sequences of VH and VL, according to the BLAST method [J. Mol. Biol., 215, 403 (1990)] or the like.

(3) Construction of Vector for Human Chimeric Antibody Expression cDNA encoding each of VH and VL of antibody of non-human animal is cloned in the upstream of genes encoding CH or CL of human antibody of vector for expression of recombinant antibody obtained in the above (1), thereby constructing a vector for human chimeric antibody expression.

In order to ligate the 3'-terminus of cDNA encoding VH or VL of antibody of non-human animal and the 5'-terminus of CH or CL of human antibody, each cDNA of VH and VL is designed and prepared so that a nucleotide sequence of a linkage portion encodes appropriate amino acids and has an appropriate recognition sequence of a restriction enzyme.

The prepared cDNAs of VH and VL are respectively cloned so that each of them is expressed in an appropriate form in the upstream of gene encoding CH or CL of the human antibody of the vector for the human CDR-grafted antibody expression obtained in the above (1) to construct a vector for human chimeric antibody expression.

In addition, cDNA encoding VH or VL of a non-human animal antibody is amplified by PCR using a synthetic DNA having a recognition sequence of an appropriate restriction enzyme at both ends, and each of them can be cloned to the vector obtained in the above (1) for recombinant antibody expression.

(4) Construction of cDNA Encoding V Region of Human CDR-Grafted Antibody cDNAs encoding VH or VL of a human CDR-grafted antibody can be obtained as follows.

Amino acid sequences of FR in VH or VL of a human antibody to which amino acid sequences of CDRs in VH or VL of a non-human antibody are transplanted are selected, respectively. Any amino acid sequences of FR can be used, as long as they are derived from a human antibody.

Examples thereof include amino acid sequences of FRs of human antibodies registered in database such as Protein Data Bank or the like, or amino acid sequences common to subgroups of FRs of human antibodies [A. L. F. DNA, US Dept. Health and Human Services (1991)] or the like. In order to inhibit the decrease in the binding activity of the antibody, amino acid sequences of FR having high homology (at least 60% or more) with the amino acid sequence of FR in VH or VL of the original antibody is selected.

Then, amino acid sequences of CDRs of the original antibody are grafted to the selected amino acid sequence of FR in VH or VL of the human antibody, respectively, to design each amino acid sequence of VH or VL of a human CDR-grafted antibody. The designed amino acid sequences are converted to DNA sequences by considering the frequency of codon usage found in nucleotide sequences of genes of antibodies [A. L. F. DNA, US Dept. Health and Human Services (1991)], and the DNA sequence encoding the amino acid sequence of VH or VL of a human CDR-grafted antibody is designed.

Based on the designed DNA sequences, several synthetic DNAs having a length of about 100 nucleotides are synthesized, and PCR is carried out using them. In this case, it is preferred that 6 synthetic DNAs per each of the H chain and the L chain are designed in view of the reaction efficiency of PCR reaction and the lengths of DNAs which can be synthesized.

Furthermore, the cDNA encoding VH or VL of a human CDR-grafted antibody can be easily cloned into the vector for expressing the human CDR-grafted antibody obtained in (1) by introducing the recognition sequence of an appropriate restriction enzyme to the 5'-terminus of the synthetic DNAs existing on the both ends.

Otherwise, it can be carried out using a synthetic DNA as a single DNA encoding each of the full-length H chain and the full-length L chain based on the designed DNA sequence. After PCR reaction, an amplified product is cloned into a plasmid such as pBluescript SK(−) (manufactured by Stratagene) or the like, and the nucleotide sequence is determined according to a method similar to the method described in (2) to obtain a plasmid having a DNA sequence encoding the amino acid sequence of VH or VL of a desired human CDR-grafted antibody.

(5) Modification of Amino Acid Sequence of V Region of Human CDR-Grafted Antibody When a human CDR-grafted antibody is produced by simply grafting only CDRs in VH and VL of a non-human antibody into FRs of VH and VL of a human antibody, its antigen binding activity is lower than that of the original non-human antibody [BIO/TECHNOLOGY, 9, 266 (1991)].

In human CDR-grafted antibodies, among the amino acid sequences of FRs in VH and VL of a human antibody, an amino acid residue which directly relates to binding to an antigen, an amino acid residue which interacts with an amino acid residue in CDR, and an amino acid residue which maintains the conformational structure of an antibody and indirectly relates to binding to an antigen are identified and substituted with amino acid residues of the original non-human antibody, thereby increasing the antigen binding activity which has been decreased.

In order to identify the amino acid residues relating to the antigen binding activity in FR, conformational structure of an antibody can be constructed and analyzed by X-ray crystallography [J. Mol. Biol., 112, 535 (1977)], computer-modeling [Protein Engineering, 7, 1501 (1994)] or the like. In addition, modified human CDR-grafted antibody having sufficient binding activity against antigen can be obtained by various attempts, such as producing several modified antibodies of each antibody and examining the correlations with their antigen binding activities.

The modification of the amino acid residue of FR in VH and VL of a human antibody can be accomplished using a synthetic DNA for modification according to PCR as described in (4). With regard to the amplified product obtained by PCR, the nucleotide sequence is determined according to the method as described in (2) so as to examine whether the desired modification has been carried out.

(6) Construction of Vector for Human CDR-Grafted Antibody Expression

A vector for human CDR-grafted antibody expression can be constructed by cloning each cDNA encoding VH or VL of a constructed recombinant antibody into upstream of each gene encoding CH or CL of the human antibody in the vector for recombinant antibody expression obtained in (1).

For example, recognizing sequences of an appropriate restriction enzymes are introduced to the 5'-terminus of synthetic DNAs positioned at both ends among synthetic DNAs used in the construction of VH or VL of the human CDR-grafted antibody obtained in (4) and (5), and cloning can be carried out so that they are expressed in an appropriate form in the upstream of each gene encoding CH or CL of the human antibody in the vector for a human CDR-grafted antibody expression as obtained in (1).

(7) Transient Expression of Recombinant Antibody

The recombinant antibodies can be expressed transiently using the vector for recombinant antibody expression obtained in (3) and (6) or the modified expression vector thereof so as to efficiently evaluate the antigen binding activity of various human CDR-grafted antibodies prepared.

Any cell can be used as a host cell into which an expression vector is introduced, as long as the host cell can express a recombinant antibody. For example, COS-7 cell (ATCC NO. CRL1651) is used [Methods in Nucleic Acids Res., CRC Press, 283 (1991)]. Introduction of the expression vector into COS-7 cell is performed by using a DEAE-dextran method [Methods in Nucleic Acids Res., CRC Press (1991)], a lipofection method [Proc. Natl. Acad. Sci. USA, 84, 7413 (1987)], or the like.

After introduction of the expression vector, the expression level and antigen binding activity of the recombinant antibody in the culture supernatant can be determined by the enzyme immunoassay [Monoclonal Antibodies-Principles and practice, Third edition, Academic Press (1996), Antibodies—A Laboratory Manual, Cold Spring Harbor Laboratory (1988), Monoclonal Antibody Experiment Manual, Kodansha Scientific (1987)] or the like.

(8) Acquisition of Transformant which Stably Expresses Recombinant Antibody and Preparation of Recombinant Antibody A transformant which stably expresses a recombinant antibody can be obtained by introducing the vector for recombinant antibody expression obtained in (3) and (6) into an appropriate host cell.

Introduction of the expression vector into a host cell is performed by electroporation [Japanese Patent Publication No. H2-257891, Cytotechnology, 3, 133 (1990)] or the like.

As the host cell into which a vector for recombinant antibody expression is introduced, any cell can be used, as long as it is a host cell which can express the recombinant antibody. Examples thereof include CHO-K1 (ATCC NO. CCL-61), DUkXB11 (ATCC NO. CCL-9096), Pro-5 (ATCC NO. CCL-1781), CHO-S (Life Technologies, Cat #11619), rat myeloma cell YB2/3HL.P2.G11.16Ag.20 (also called YB2/0), mouse myeloma cell NSO, mouse myeloma cell SP2/0-Ag14 (ATCC No. CRL1581), mouse P3-x63-Ag8653 cell (ATCC No. CRL1580), CHO cell in which a dihydrofolate reductase gene is defective [Proc. Natl. Acad. Sci. U.S.A., 77, 4216 (1980)], lection resistance-acquired Lec13 [Somatic Cell and Molecular genetics, 12, 55 (1986)], CHO cell in which $\alpha1,6$-fucosyltransaferse gene is defected (WO 2005/035586, WO 02/31140), rat YB2/3HL.P2.G11.16Ag.20 cell (ATCC No. CRL1662), or the like.

It is also possible to use host cells in which a protein such as an enzyme involved in synthesis of intracellular sugar nucleotide GDP-fucose, a protein such as an enzyme involved in the modification of a sugar chain in which 1-position of fucose is bound to 6-position of N-acetylglucosamine in the reducing end through $\alpha$-bond in the complex N-glycoside-linked sugar chain or a protein involved in transporting an intracellular sugar nucleotide GDP-fucose to the Golgi body exhibits lowered activity or is deficient, for example, $\alpha1,6$-fucosetransferase gene-knockout CHO cell (WO 2005/035586 and WO 02/31140) or the like.

After introduction of the expression vector, transformants which stably express a recombinant antibody are selected by culturing them in a medium for animal cell culture containing an agent such as G418 sulfate or the like (Japanese Patent Publication No. H2-257891).

Examples of the medium for animal cell culture include RPMI1640 medium (manufactured by Invitrogen), GIT medium (manufactured by Nihon Pharmaceutical), EX-CELL301 medium (manufactured by JRH), IMDM (manufactured by Invitrogen), Hybridoma-SFM (manufactured by Invitrogen), media obtained by adding various additives such as FBS to these media, or the like.

The recombinant antibody is produced and accumulated in a culture supernatant by culturing the obtained transformants in a medium. The expression level and antigen binding activity of the recombinant antibody in the culture supernatant can be measured by ELISA or the like. Also, in the transformant, the expression level of the recombinant antibody can be increased by using DHFR amplification system (Japanese Patent Publication No. H2-257891) or the like.

The recombinant antibody is purified from the culture supernatant of the transformant by using a protein A column [Monoclonal Antibodies-Principles and practice, Third edition, Academic Press (1996), Antibodies—A Laboratory Manual, Cold Spring Harbor Laboratory (1988)]. In addition, the protein purification methods such as gel filtration, ion-exchange chromatography or ultrafiltration can be used in combination.

The H chain or the L chain of the purified recombinant antibody or the molecular weight of the antibody molecule as a whole can be determined by polyacrylamide gel electrophoresis [Nature, 227, 680 (1970)], Western blotting [Monoclonal Antibodies-Principles and practice, Third edition, Academic Press (1996), Antibodies—A Laboratory Manual, Cold Spring Harbor Laboratory (1988)], or the like.

3. Activity Evaluation of Purified Monoclonal Antibody or Antibody Fragment Thereof The activities of the purified monoclonal antibody of the present invention or the antibody fragment thereof can be evaluated in the following manner.

The binding activity to FOLR1-expressing cell line is evaluated by the binding assay described in the above 1. (6-a) and a surface plasmon resonance method using the Biacore system described in the above (6-b). Furthermore, it can be measured by fluorescent antibody technology [Cancer Immunol. Immunother, 36, 373 (1993)] or the like.

The CDC or ADCC activity against antigen-positive cultured cell line is measured using known measurement methods [Cancer Immunol. Immunother., 36, 373 (1933)].

4. Method of Regulating Effector Activity of Antibody

Examples of methods of regulating the effector activity of the anti-FOLR1 monoclonal antibody of the present invention include a method of regulating the amount of fucose (also referred to as core fucose) which forms α1,6-bound to N-acetylglucosamine (GlcNAc) present in a reducing end of a complex type N-linked sugar chain bound to asparagine (Asn) at position 297 of the Fc region of the antibody (WO 2005/035586, WO 2002/31140, WO 00/61739), a method of modifying amino acid residues in the Fc region of the antibody, or the like. The effector activity of the anti-FOLR1 monoclonal antibody of the present invention can be regulated by using any of these methods.

The "effector activity" refers to an antibody-dependent activity induced via the Fc region of an antibody. ADCC activity, CDC activity, ADP (Antibody-dependent phagocytosis) activity caused by a phagocyte such as a macrophage or a dendritic cell, or the like is known.

As the method for measuring the effector activity, for example, cancer cells as a target, human peripheral blood mononuclear cells (PBMC) as an effector, and cancer cell-specific antibodies are mixed, and after 4 hr incubation, cell cytotoxicity can be determined by measuring the release of lactate dehydrogenase (LDH) as an index. Otherwise, human PBMC is mixed with, for example, an antibody recognizing a Blood cell-specific antigen such as CD20, and after incubation, the effector activity can be determined by measurement of the LDH release or by flow cytometry for the reduced number of the cells. Otherwise, cancerous ascitic fluid is mixed with cancer cell-specific antibody, and after incubation, the effector activity can be determined by measurement of the LDH release or by flow cytometry for the reduced number of the cells.

The effector activity of an antibody can be increased or decreased by regulating the content of the core fucose in the complex type N-linked sugar chain of Fc of the antibody. As a method of decreasing the content of fucose binding to the complex type N-liked sugar chain bound to Fc of the antibody, the antibody is expressed using α1,6-fucosetransferase gene-deficient CHO cell, whereby an antibody to which no fucose has bound can be obtained. The antibody to which no fucose has bound has a higher ADCC activity.

On the other hand, as a method of increasing the content of fucose binding to the complex type N-linked sugar chain bound to Fc of an antibody, an antibody is expressed using a host cell to which α1,6-fucosetransferase gene has been introduced, whereby an antibody to which fucose has bound can be obtained. The ADCC activity of the antibody to which fucose has bound is lower than that of the antibody to which no fucose has bound.

In addition, the ADCC activity or CDC activity can be increased or decreased by modifying amino acid residues of the Fc region of an antibody. For example, the CDC activity of an antibody can be increased using the amino acid sequence of the Fc region disclosed in the specification of US Patent Application Publication No. 2007/0148165.

In addition, the ADCC activity or CDC activity can also be increased or decreased by performing amino acid modifications described in the specifications of U.S. Pat. No. 6,737,056, 7,297,775 or 7,317,091.

Furthermore, it is possible to obtain an antibody of which the effector activity has been regulated by applying the above described methods in combination to one antibody.

5. Method for Treating Disease Using Anti-FOLR1 Monoclonal Antibody or Antibody Fragment of the Present Invention The monoclonal antibody or the antibody fragment thereof of the present invention can be used for treating diseases associated with FOLR1-positive cells.

The therapeutic agent comprising the monoclonal antibody of the present invention or the antibody fragment thereof or the derivative thereof may include only the antibody or the antibody fragment thereof or the derivative thereof as an active ingredient, and is generally supplied as a pharmaceutical preparation produced by mixing it with one or more pharmaceutically acceptable carriers in accordance with a method well known in the technical field of pharmaceutics.

Examples of administration route may include oral administration and parenteral administration, such as buccal, tracheal, intrarectal, subcutaneous, intramuscular, intravenous or intraperitoneal administration. Examples of the administration form may include spray, capsules, tablets, powder, granules, syrup, emulsion, suppository, injection, ointment, tape, or the like.

Examples of the pharmaceutical preparation suitable for oral administration may include emulsions, syrups, capsules, tablets, powders, granules or the like.

Liquid preparations such as emulsions and syrups are produced using, as additives, water, sugars such as sucrose, sorbitol or fructose, glycols such as polyethylene glycol or propylene glycol, oils such as sesame oil, olive oil or soybean oil, antiseptics such as p-hydroxybenzoate, flavors such as strawberry flavor or peppermint, or the like.

Capsules, tablets, powders, granules or the like are produced using, as additives, excipients such as lactose, glucose, sucrose or mannitol, disintegrating agents such as starch or sodium alginate, lubricants such as magnesium stearate or talc, binders such as polyvinyl alcohol, hydroxypropylcellulose or gelatin, surfactants such as fatty acid ester, plasticizers such as glycerin, or the like.

Examples of the pharmaceutical preparation suitable for parenteral administration may include injections, suppositories, sprays or the like.

Injections are prepared using a carrier such as a salt solution, a glucose solution or a mixture of both thereof. Suppositories are prepared using a carrier such as cacao butter, hydrogenated fat, carboxylic acid or the like.

Sprays are prepared using a carrier which does not stimulate the buccal or airway mucous membrane of the patient and can facilitate absorption of the monoclonal antibody or the antibody fragment thereof by dispersing it as fine particles. Examples of the carrier include lactose, glycerin or the like. Also, it can be prepared as aerosols or dry powders.

In addition, the components exemplified as additives for preparations suitable for oral administrations can also be added to the parenteral preparations.

6. Method for Diagnosing Disease Using Anti-FOLR1 Monoclonal Antibody or Antibody Fragment of the Present Invention A disease relating to FOLR1 can be diagnosed by detecting or determining FOLR1 or a FOLR1-expressing cell using the monoclonal antibody or antibody fragment of the present invention.

A diagnosis of cancer, one of the diseases relating to FOLR1, can be carried out by, for example, the detection or measurement of FOLR1 as follows.

The diagnosis can be carried out by detecting FOLR1 expressed in cancer cells of cancer primary site, metastatic site, or cancerous ascitic fluid of a patient using an immunological method such as flow cytometry or the like.

An immunological method is a method in which an antibody amount or an antigen amount is detected or determined using a labeled antigen or antibody. Examples thereof include radioactive substance-labeled immunoantibody method, enzyme immunoassay, fluorescent immunoassay, luminescent immunoassay, Western blotting, physico-chemical means or the like.

Examples of the radioactive substance-labeled immunoantibody method include a method, in which the antibody or antibody fragment of the present invention is allowed to react with an antigen or a cell expressing an antigen or the like, then anti-immunoglobulin antibody subjected to radioactive labeling or a binding fragment thereof is allowed to react therewith, followed by determination using a scintillation counter or the like.

Examples of the enzyme immunoassay include a method, in which the antibody or antibody fragment of the present invention is allowed to react with an antigen or a cell expressing an antigen or the like, then an anti-immunoglobulin antibody or a binding fragment thereof subjected to antibody labeling is allowed to react therewith and the colored pigment is measured by a spectrophotometer, and, for example, sandwich ELISA may be used.

As a label used in the enzyme immunoassay, any known enzyme label [Enzyme Immunoassay, IGAKU-SHOIN Ltd. (1987)] can be used. Examples thereof include alkaline phosphatase labeling, peroxidase labeling, luciferase labeling, biotin labeling or the like.

Sandwich ELISA is a method in which an antibody is bound to a solid phase, antigen to be detected or measured is trapped and another antibody is allowed to react with the trapped antigen. In the ELISA, two kinds of antibodies which recognize the antigen to be detected or measured or the antibody fragment thereof in which antigen recognizing site is different are prepared and one antibody or antibody fragment is previously adsorbed on a plate (e.g., 96-well plate) and another antibody or antibody fragment is labeled with a fluorescent substance such as FITC, an enzyme such as peroxidase, or biotin, or the like.

The plate to which the above antibody is adsorbed is allowed to react with the cell or disrupted suspension thereof, tissue or disintegrated solution thereof, cell culture supernatant, serum, pleural effusion, ascitic fluid, eye solution or the like, separated from living body, then allowed to react with labeled monoclonal antibody or antibody fragment and a detection reaction according to the labeled substance is carried out. An antigen concentration in the test sample can be calculated from a calibration curve prepared by a stepwise dilution of antigen of known concentration.

As an antibody used for sandwich ELISA, any of a polyclonal antibody and a monoclonal antibody may be used or antibody fragments such as Fab, Fab' and $F(ab)_2$ may be used. As a combination of two kinds of antibodies used in sandwich ELISA, a combination of monoclonal antibodies or antibody fragments recognizing different epitopes may be used or a combination of polyclonal antibody with monoclonal antibody or antibody fragments may be used.

A fluorescent immunoassay includes a method described in the literatures [Monoclonal Antibodies—Principles and practice, Third Edition, Academic Press (1996); Manual for Monoclonal Antibody Experiments, Kodansha Scientific (1987)] or the like. As a label used for the fluorescent immunoassay, any of known fluorescent labels [Fluorescent Immunoassay, Soft Science, (1983)] may be exemplified. Examples include FITC, RITC or the like.

The luminescent immunoassay is carried out using the methods described in the literature [Bioluminescence and Chemical Luminescence, clinical test, 42, Hirokawa Shoten (1998)] or the like. As a label used for luminescent immunoassay, any of known luminescent labels can be exemplified. Examples thereof may include acridinium ester, lophine or the like.

Western blotting is carried out as follows. An antigen or a cell expressing an antigen is fractionated by SDS (Sodium dodecyl sulfate)-PAGE [Antibodies—A Laboratory Manual Cold Spring Harbor Laboratory, (1988)]. Then, the gel is blotted onto a polyvinylidene fluoride (PVDF) membrane or nitrocellulose membrane, and the membrane is allowed to react with antigen-recognizing antibody or antibody fragment. Further, it is allowed to react with an anti-mouse IgG antibody or antibody fragment which is labeled with a fluorescent substance such as FITC, an enzyme label such as peroxidase, a biotin label, or the like. After the reaction, the label is visualized to measure. An example thereof is described below.

Cells or tissues in which a polypeptide having the amino acid sequence represented by SEQ ID NO. 1 is expressed are disrupted and, under reducing conditions, 0.1 to 30 μg as a protein amount per lane is electrophoresed by an SDS-PAGE method. The electrophoresed protein is transferred to a PVDF membrane and allowed to react with PBS containing 1 to 10% of BSA (hereinafter referred to as BSA-PBS) at room temperature for 30 minutes for blocking.

Here, the monoclonal antibody of the present invention is allowed to react therewith, washed with PBS containing 0.05 to 0.1% Tween 20 (hereinafter, referred to as Tween-PBS) and allowed to react with goat anti-mouse IgG labeled with peroxidase at room temperature for 2 hours. It is washed with Tween-PBS and a band to which the monoclonal antibody is bound is detected using ECL Western Blotting Detection Reagents (manufactured by Amersham) or the like, thereby detecting a polypeptide having the amino acid sequence represented by SEQ ID NO. 1. As an antibody used for the detection in Western blotting, an antibody which can bind to a polypeptide having no conformational structure of a natural type is used.

The physicochemical method is specifically carried out by reacting FOLR1 as the antigen with the monoclonal antibody or antibody fragment of the present invention to form an aggregate, and detecting this aggregate. Other examples of the physicochemical methods may include a capillary method, a one-dimensional immunodiffusion method, an immunoturbidimetry, a latex immunoturbidimetry [*Handbook of Clinical Test Methods*, KANEHARA&CO., LTD. (1988)] or the like.

In a latex immunoturbidimetry method, a carrier such as polystyrene latex having a particle size of about 0.1 to 1 μm sensitized with antibody or antigen may be used and when an antigen-antibody reaction is carried out using the corresponding antigen or antibody, scattered light in the reaction solution increases while transmitted light decreases. By detecting such a change as absorbance or integral sphere turbidity, it is possible to measure antigen concentration, or the like, in the test sample.

A method for evaluating therapeutic efficacy of the antibody using the antibody or antibody fragment thereof of the present invention before treatment initiation may be, for example, as follows.

First, before treatment initiation, cancerous ascitic fluid is collected from the body of a patient and the antibody or antibody fragment thereof of the present invention is added to the suspension. After a predetermined time, anti-tumor activity is measured. As a result of the measurement, when anti-tumor activity is observed, it can be recognized before treatment initiation that the antibody or antibody fragment thereof of the present invention is effective in the treatment of the patient having ascitic fluid.

EXAMPLES

Hereinafter, the present invention will be described in detail with reference to Examples. However, the present invention is not limited to the following Examples.

Example 1

Acquisition of cDNAs of FOLR1, FOLR2, and FOLR3 cDNAs of human FOLR1 (hereinafter, referred to as FOLR1), human FOLR2 (hereinafter, referred to as FOLR2), and human FOLR3 (hereinafter, referred to as FOLR3) were purchased from SC122853 (Origene), SC119666 (Origene), and #100015838(Open Biosystem), respectively and used in experiments later.

Example 2

Construction of FOLR1-Expressing Vector

First, FOLR1 gene was amplified by PCR using FOLR1-F (SEQ ID NO. 2) and FOLR1-R (SEQ ID NO. 3) primers. It was confirmed whether the amplified gene had the purpose sequence, and then it was ligated to pKANTEX93 vector (WO 97/10354) which had been digested with EcoRI and KpnI restriction enzymes, thereby constructing a FOLR1 gene-expressing vector.

Example 3

Preparation of FOLR1-Expressing Cells

The DHFR-deficient CHO (Chinese hamster ovary) cell line DG44 (CHO/DG44 cell) was purchased from Mitsubishi Chemical Corporation Yokohama Research Center and used in the preparation of FOLR1-expressing cells. Culture medium [IMDM (GIBCO) supplemented with 10% inactivated dialyzed fetal bovine serum (dFBS) (GIBCO), HT supplement (GIBCO), and 50 μg/mL gentamycin] was used for culture.

First, the FOLR1-expressing vector was digested by AatII treatment, and linear DNA thus obtained was purified and suspended in a sterile solution. This DNA was transfered into CHO/DG44 cells by electroporation, and then cultured for 3 days in the culture medium without HT supplement. Thereafter, drug-resistant cells were selected in a selection medium [IMDM, 10% inactivated dFCS, 0.5 mg/mL G418 (Nacalai), and 50 μg/mL gentamycin]. The drug-resistant cells thus selected were seeded in a 96-well plate at a density of 75 cells/plate, and further cultured in the selection medium for 2 weeks. Each well was observed under a microscope and extensive culture of single clones was serially performed.

Example 4

Confirmation of FOLR1 Expression

The drug-resistant cells thus obtained was detached with 0.02% EDTA solution (Nacalai), washed with PBS, and then suspended in 1% BSA/PBS. Subsequently, they were seeded in a 96-well plate at a density of $2 \times 10^5$ cells/well, and centrifugation was performed at 1700 rpm for 1 minute. The supernatant was discarded, and LK26 antibody (GeneTex) prepared at a concentration of 2 μg/mL using 1% BSA/PBS was added, and reaction was conducted at 4° C. for 1 hour.

The cells were washed, and then Anti-mouse IgG-FITC (Dako) diluted 100-fold in 1% BSA/PBS was added, and reaction was conducted at 4° C. for 1 hour. The cells were washed again and then suspended in 1% BSA/PBS, and fluorescence intensity was analyzed by flow cytometry (manufactured by Beckman coulter, FC500MPL). The clones showing significant FOLR1 expression were selected, and these cells were used as FOLR1-expressing CHO cells.

Example 5

Cloning of Cynomolgus Monkey FOLR1

Cynomolgus monkey FOLR1 was cloned from the frozen kidney tissue of cynomolgus monkey. RNAiso Plus (Takara) was added to the frozen kidney tissue with several mm square and the tissue was homogenized using a homogenizer Pestle (AsOne). It was left at room temperature for 5 minutes, and then total RNA was obtained according to the recommended protocol of RNAiso plus and dissolved in DEPC-treated solution (Invitrogen). Subsequently, in order to synthesize cDNA from the total RNA, a PrimeScript II 1st strand cDNA synthesis kit (Takara) and oligo dT as a primer were used to perform reverse transcription.

Subsequently, CyFOLR1-F (SEQ ID NO. 4) and CyFOLR1-R (SEQ ID NO. 5) primers designed based on human FOLR1 (NM_000802) and rhesus monkey FOLR1 (XM_001114655) were used to amplify cynomolgus monkey FOLR1 gene by PCR.

PCR sample was electrophoresed on a 2% agarose gel, and then the amplified band was cut out, and recovered using a QIAquick Gel Extraction kit (QIAGEN). TA cloning was carryied out by using a TOPO TA Cloning Kit for Sequencing (Invitrogen), and transfered into Competent high *E. coli* DH5α (TOYOBO). The *E. coli* was cultured in an LB plate containing 100 μg/mL ampicillin at 37° C. overnight. Thereafter, each colony was cultured, and the plasmid was extracted using NA-2000 (KURABO), followed by sequencing analysis.

As a result, the nucleotide sequence of the cloned cynomolgus monkey FOLR1 was identified as SEQ ID NO. 6, and the amino acid sequence (SEQ ID NO. 7) based on this nucleotide sequence was found to be identical to rhesus monkey FOLR1 (XM_001114655).

Example 6

Construction of FOLR1-Fc, FOLR2-Fc, FOLR3-Fc, and Cynomolgus Monkey FOLR1-Fc-Expressing Vectors PCR was performed in order to construct vectors expressing the recombinant proteins (hereinafter, referred to as FOLR1-Fc, FOLR2-Fc, FOLR3-Fc, and cynomolgus monkey FOLR1-Fc) that were prepared by adding Human IgG1 Fc (Hinge region and CH2-CH3 region) to the C-terminus of FOLR1 (1-233 amino acids), FOLR2 (1-227 amino acids), FOLR3 (1-243 amino acids), and cynomolgus monkey FOLR1 (1-233 amino acids), respectively.

FOLR1-Fc-F (SEQ ID NO. 8) and FOLR1-Fc-R (SEQ ID NO. 9) as primers for the preparation of FOLR1-Fc-expressing vector, FOLR2-Fc-F (SEQ ID NO. 10) and FOLR2-Fc-R (SEQ ID NO. 11) as primers for the preparation of FOLR2-Fc-expressing vector, FOLR3-Fc-F (SEQ ID NO. 12) and FOLR3-Fc-R (SEQ ID NO. 13) as primers for the preparation of FOLR3-Fc-expressing vector, and CyFOLR1-Fc-F (SEQ ID NO. 14) and CyFOLR1-Fc-R (SEQ ID NO. 15) as primers for the preparation of cynomolgus monkey FOLR1-Fc-expressing vector were used.

The PCR products were provided for agarose gel electrophoresis, and the amplified genes were purified using a QIAquick Gel Extraction kit (QIAGEN), and subcloning was performed using a TA cloning kit (Invitrogen). The vectors having the purpose sequence were selected, and the purpose sequence was digested with EcoRI and AhdI.

Meanwhile, Human IgG1 Fc region was cleaved from pKANTEX93 using AhdI and SpeI. The purpose sequence and Human IgG1 Fc region thus cleaved were ligated to pKANTEX93 that had been treated with EcoRI and SpeI, and used as FOLR1-Fc, FOLR2-Fc, FOLR3-Fc, and cynomolgus monkey FOLR1-Fc recombinant protein-expressing vectors.

Example 7

Preparation of FOLR1-Fc, FOLR2-Fc, FOLR3-Fc, and Cynomolgus Monkey FOLR1-Fc Expressing Cells In the preparation of FOLR1-Fc, FOLR2-Fc, FOLR3-Fc, and cynomolgus monkey FOLR1-Fc expressing cells, CHO/Ms704 cell (WO 03/85107) which is a FUT8 knockout CHO/DG44 cell prepared from CHO/DG44 was used. Further, FOLR1-Fc, FOLR2-Fc, FOLR3-Fc and cynomolgus monkey FOLR1-Fc-expressing vectors prepared in Example 6 were used as the expression vectors. Typically, subculture, gene transfection, and selection of drug-resistant cells were carried out in the same manner as in Example 3.

Extensive culture of the selected drug-resistant cells was serially performed, and then the cells were washed with PBS and cultured in a collection medium [EX-CELL 302 Serum-Free Medium for CHO Cells (Sigma-Aldrich), 6 mmol/L L-glutamine (Invitrogen), and 50 µg/mL gentamycin] for 1 week. The culture supernatant was collected, and provided for subsequent purification.

Example 8

Purification of FOLR1-Fc, FOLR2-Fc, FOLR3-Fc, and Cynomolgus Monkey FOLR1-Fc

FOLR1-Fc, FOLR2-Fc, FOLR3-Fc, and cynomolgus monkey FOLR1-Fc were purified from the culture supernatant using a column filled with ProSep-vA High Capacity.

First, the culture supernatant was passed through the column, and then the column was washed with PBS. Elution was serially carried out using an elution buffer of pH 5.0, 3.5, 3.0 (0.1 M citric acid monohydrate-NaOH/pH 5.0, 3.5, 3.0). The eluted fractions were rapidly neutralized using a neutralization buffer (2 M Tris-HCl/pH 8.5). Absorbance (280 nm) of each fraction was measured, and serial fractions having the high measured values were collected as antibody fraction. Dialysis was carried out using PBS, and then the purified proteins were passed through a 0.22 µm filter. Absorbance index at 280 nm was 2.2 for FOLR1-Fc, 2.3 for FOLR2-Fc, 2.1 for FOLR3-Fc, and 2.2 for cynomolgus monkey FOLR1-Fc, and concentrations thereof were calculated therefrom.

Example 9

Construction of FOLR1-mycHis-Expressing Vector

In order to construct a vector expressing a recombinant protein having myc and His tag at the C-terminus of FOLR1 (1-233 amino acids) (hereinafter, referred to as FOLR1-mycHis), PCR was carried out. FOLR1-mH-F (SEQ ID NO. 16) and FOLR1-mH-R (SEQ ID NO. 17) were used as primers for the preparation of FOLR1-mycHis-expressing vector.

The purpose sequence was purified from the PCR product, and ligated to pKANTEX93 that had been treated with EcoRI and SpeI to prepare the FOLR1-mycHis-expressing vector.

Example 10

Preparation of FOLR1-mycHis-Expressing Cells

CHO/DG44 cells were used for the preparation of FOLR1-mycHis-expressing cells. Further, the FOLR1-mycHis-expressing vector prepared in Example 9 was used as the expression vector. Typically, subculture, gene transfection, selection of drug-resistant cells and collection of culture supernatant were carried out in the same manner as in Example 7.

Example 11

Purification of FOLR1-mycHis

FOLR1-mycHis was purified from the culture supernatant using the column packed with Ni-NTA Agarose (Invitrogen).

First, the wash buffer (50 mmol/L $NaH_2PO_4$ (pH 8.0), 300 mmol/L NaCl) was applied to the column, and the culture supernatant was passed through the column, and then the column was washed with wash buffer. Elution was carried out using an elution buffer (prepared by adding 500 mmol/L imidazole to the wash buffer). Absorbance (280 nm) of the eluted fractions was measured, and serial fractions having the high measured values were collected as FOLR1-mycHis fraction. Dialysis was carried out using PBS, and then the purified proteins were passed through a 0.22 µm filter, and used as a purified FOLR1-mycHis. The concentration was calculated from absorbance index at 280 nm of 2.8.

Example 12

Rat Immunization

In order to acquire monoclonal antibodies against FOLR1, 4-week-old female SD rats were immunized. First, 50 µg of FOLR1-Fc was intraperitoneally administered to SD rats, together with 2 mg of aluminium hydroxide adjuvant (Antibodies—A Laboratory Manual, Cold Spring Harbor Laboratory, 1988) and pertussis vaccine (Nacalai). 2 weeks after first administration, 50 µg of FOLR1-Fc was administered once a week three times.

Example 13

Rat Anti-Serum Test

Blood was collected from the tail vein of the SD rat of Example 12 at 3 days after final administration, and serum antibody titer against FOLR1 was analyzed by flow cytometry. FOLR1-expressing CHO cell and FOLR2-expressing CHO cell were used as positive and negative cells, respectively.

First, FOLR1-expresing CHO cells and FOLR2-expressing CHO cells were detached using 0.02% EDTA solution (Nacalai), and then washed with PBS and then suspended in 1% BSA/PBS. Subsequently, cells were seeded in a 96-well plate at a density of $5 \times 10^5$ cells/well, followed by centrifugation at 1500 rpm for 1 minute.

The supernatant was discarded, and then SD rat serum diluted 100- to 1000-fold in 1% BSA/PBS were added to the cells, and were allowed to react at 4° C. for 30 minutes. The cells were washed. Then, Alexa488-labeled anti-rat IgG(H+L) polyclonal antibody (Invitrogen) diluted in 1% BSA/PBS was added to cells and they were allowed to react at 4° C. for 30 minutes. The cells were washed again and then suspended in 1% BSA/PBS, and fluorescent intensity was analyzed by flow cytometry.

Example 14

Preparation of Hybridoma

SD rats showing significant serum antibody titer against FOLR1-expressing CHO cells were further immunized with 50 µg of FOLR1-Fc. 3 days later, the spleen was surgically excised from the SD rat, and provided for cell fusion.

First, the excised spleen was homogenized on a slide glass. This spleen tissue was suspended in MEM (Invitrogen), and passed through a cell strainer to remove residual tissue. The supernatant was discarded after centrifugation, and then the hemolysis was caused by addition of Red blood cell lysing buffer (SIGMA). The reaction was terminated by addition of MEM, and the supernatant was discarded after centrifugation. The resultant was suspended in MEM again and used as the spleen cells.

The spleen cells thus obtained were mixed with ⅛-fold mouse myeloma cell line, P3-U1. The supernatant was discarded after centrifugation, and 500 µL of PEG solution [each 1 mL of Polyethylene glycol 1000 (Junsei Chemical) and MEM was mixed and 350 µL of DMSO (Nacalai) was added thereto] was gently added while warmed in a water bath at 37° C., and 45 mL of MEM was further added. The supernatant was discarded after centrifugation, and cells were suspended in a HAT medium [5 mL of HAT solution (GIBCO) and 0.5 mL of 55 mmol/L 2-Mercaptoethanol (Invitrogen) added to 500 mL of RPMI1640 (Wako)]. The obtained hybridoma was seeded in a 96-well plate and cultured.

Example 15

Hybridoma Screening (ABI8200 Cellular Detection System)

After the hybridoma was cultured for 10 days, the culture supernatant of each well was collected, and the reactivity against FOLR1 was analyzed by a fluorescent antibody staining method (ABI8200 Cellular Detection System, hereinafter, referred to as FMAT). FOLR1-expressing CHO cell and FOLR2-expressing CHO cell were used as positive and negative cells, respectively. First, the positive and negative cells were detached using 0.05% trypsin solution (Invitrogen), and seeded in a 96-well plate at a density of $1 \times 10^4$ cells/100 µL per well, and cultured overnight.

Subsequently, 10 µL of hybridoma culture supernatant and 50 µL of Alexa647-labeled anti-rat IgG(H+L) polyclonal antibody (Invitrogen) diluted to 1/5000-fold were added to each well. They were allowed to react at room temperature for 3 hours, and then fluorescent intensity was analyzed by FMAT. The hybridomas in the wells which showed specific reactivity to FOLR1 positive CHO cell in FMAT was cloned twice by limiting dilution.

Example 16

Hybridoma Screening (Surface Plasmon Resonance Method)

After cloning, the hybridoma culture supernatant was used to measure its affinity for FOLR1 by a surface plasmon resonance method. As instruments for measurement, Biacore T100 (GE Healthcare), and CM5 chip (GE Healthcare) were used. First, Mouse Antibody Capture Kit (GE Healthcare) was immobilized onto the CM5 chip by amine coupling.

Subsequently, the hybridoma culture supernatant was applied using HBS-EP+buffer (GE Healthcare), and the antibodies contained in the supernatant were captured on the CM5 chip. Subsequently, FOLR1-mycHis prepared by five-step dilution (188, 375, 750, 1500, 3000 ng/mL) was applied as an analyte.

The affinity was analyzed from association constant (Ka) and dissociation constant (Kd) by Single-cycle kinetics. Kinetic constants (ka, kd, KD) were calculated by 1:1 binding model using a Biacore T-100 Evaluation software (GE Healthcare).

As a result, affinities (KD, calculated from kd/ka) of LK26 antibody (GeneTex) and MOv18 antibody (ALEXIS BIOCHEMICALS) for FOLR1-mycHis were 66 nmol/L and 92 nmol/L, respectively. Meanwhile, affinity of the culture supernatant of hybridoma RA15-7 clone (hereinafter, referred to as RA15-7) for FOLR1-mycHis was 1.9 nmol/L.

Therefore, it was revealed that the culture supernatant of RA15-7 includes antibody showing very high affinity for FOLR1, compared to the conventional LK26 antibody and MOv18 antibody.

Example 17

Evaluation of Reactivity of RA15-7 Culture Supernatant (Flow Cytometry)

The reactivity of the antibody contained in the RA15-7 culture supernatant to human ovarian cancer cell line PA-1

(ATCC NO. CRL-1572) which is reactive to LK26 antibody was analyzed by flow cytometry. Further, human ovarian cancer cell line TOV-112D (ATCC NO. CRL-11731) which is non-reactive to LK26 antibody was used as a negative control to analyze the reactivity of the antibody contained in the RA15-7 culture supernatant in the same manner.

First, human ovarian cancer cell lines, PA-1 and TOV-112D cells were detached using 0.02% EDTA solution (Nacalai), and then washed with PBS, and suspended in 1% BSA/PBS. Subsequently, the cells were seeded in a 96-well plate at a density of $2 \times 10^5$ cells/well, followed by centrifugation at 1500 rpm for 1 minute. After the supernatant was discarded, 50 μL of RA15-7 culture supernatant was added to each well, and allowed to react at 4° C. for 30 minutes.

Cells were washed, and then Alexa488-labeled anti-rat IgG(H+L) polyclonal antibody (Invitrogen) diluted in 1% BSA/PBS was added thereto, and they were allowed to react at 4° C. for 30 minutes. The cells were washed again, and then suspended in 1% BSA/PBS, and fluorescent intensity was analyzed by flow cytometry.

As a result, the RA15-7 culture supernatant showed reactivity only to PA-1, and no reactivity to TOV-112D, like LK26 antibody. Therefore, it was suggested that the antibody contained in the RA15-7 culture supernatant recognize cancer cells with high FOLR1 expression.

In the same manner, the reactivity of the RA15-7 culture supernatant to cynomolgus monkey kidney-derived cell line JTC-12 (RCB1485, RIKEN CELL BANK) was also analyzed by flow cytometry. As a result, the RA15-7 culture supernatant showed reactivity to JTC-12 cell, like LK26 antibody. Therefore, it was suggested that the antibody contained in the RA15-7 culture supernatant recognize cynomolgus monkey FOLR1 as well as human FOLR1.

Example 18

Identification of Subclass of Antibody Contained in RA15-7 Culture Supernatant

The subclass of the antibody contained in the RA15-7 culture supernatant was identified by ELISA.

First, 50 μL/well of anti-rat IgG(H+L) polyclonal antibody (MP Biomedical) prepared at a concentration of 50 μg/mL using PBS was added in a 96-well plate for ELISA and incubated at 4° C. overnight. Each well was washed with PBS, and then 100 μL/well of 1% BSA/PBS was added at room temperature for 1 hour for blocking. Each well was washed with PBS again, and then 50 μL/well of RA15-7 culture supernatant was added, and allowed to react at room temperature for 2 hours.

Each well was washed with 0.05% tween20/PBS, and 50 μL/well of each HRP-conjugated rat Ig isotype (IgG1, IgG2, IgG3, IgG4, IgM) antibody and rat κ chain-specific antibody (Southern Biotech) which were diluted in 1% BSA/PBS were added and allowed to react at room temperature for 1 hour.

Each well was washed with PBS, and 50 μL/well of ABTS [2.2-azinobis(3-ethylbenzothiazole-6-sulfonic acid)ammonium, Wako] substrate solution [(1 mmol/L ABTS, 0.1 mol/L citrate buffer (pH 4.2), 0.1% $H_2O_2$)] was added, and allowed to react at room temperature. After sufficient color development was confirmed, 50 μL/well of 5% SDS solution was added to terminate the reaction, and absorbance at 415 nm was measured.

As a result, the antibody contained in the RA15-7 culture supernatant was identified as a rat IgG1κ antibody.

Example 19

Evaluation of Specificity of Antibody Contained in RA15-7 Culture Supernatant (ELISA)

The reactivities of the antibody contained in the RA15-7 culture supernatant to FOLR1-Fc, FOLR2-Fc, FOLR3-Fc, and cynomolgus monkey FOLR1-Fc were evaluated.

First, 50 μL/well of goat anti-rat IgG(H+L)(CALTAG) which was diluted 1000-fold in PBS was added in a 96-well plate for ELISA and incubated at 4° C. overnight.

Each well was washed with PBS, and then 100 μL/well of 1% BSA/PBS was added at room temperature for 1 hour for blocking. Each well was washed with PBS again, and 50 μL/well of the RA15-7 culture supernatant was added, and allowed to react at room temperature for 1 hour. Each well was washed with 0.05% tween20/PBS, and 50 μL/well of FOLR1-Fc, FOLR2-Fc, FOLR3-Fc, and cynomolgus monkey FOLR1-Fc which were diluted in 1% BSA/PBS were added, and allowed to react at room temperature for 1 hour.

Each well was washed with 0.05% tween20/PBS, and then 50 μL/well of Goat anti-human IgG(H+L)-POD (American Qualex) which was diluted 2000-fold in 1% BSA/PBS was added and allowed to react at room temperature for 1 hour. Each well was washed with PBS, and then 50 μL/well of ABTS substrate solution was added, and allowed to react at room temperature. After sufficient color development was confirmed, 50 μL/well of 5% SDS solution was added to terminate the reaction, and absorbance at 415 nm was measured.

As a result, it was shown that the antibody contained in the RA15-7 culture supernatant binds to human and cynomolgus monkey FOLR1-Fc, but do not bind to FOLR2-Fc and FOLR3-Fc. That is, it was shown that the antibody contained in the RA15-7 culture supernatant was human and cynomolgus monkey FOLR1-specific antibody.

Example 20

Purification of RA15-7 Antibody

The hybridoma RA15-7 was cultured for 1 week in a medium which was prepared by adding 5% Fetal Bovine Serum Ultra Low IgG (Invitrogen) to Hybridoma-SFM (Invitrogen). Purification of the RA15-7 antibody from the culture supernatant was carried out in the same manner as in Example 8. The concentration was calculated from absorbance index at 280 nm of 1.4.

Example 21

Evaluation of Antibody Affinity by Competitive ELISA

It was evaluated whether RA15-7 antibody, LK26 antibody, and MOv18 antibody compete with each other for binding to FOLR1.

First, 50 μL/well of each antibody prepared at a concentration of 2 μg/mL using PBS was added in a 96-well plate for ELISA, and incubated at 4° C. overnight. Each well was washed with PBS, and 200 μL/well of 1% BSA/PBS was added at room temperature for 1 hour for blocking. Each well was washed with PBS again, and each 50 μL/well of anti-FOLR1 antibody (0.012-3 μg/mL) and FOLR1-Fc (0.2 μg/mL) were added, and allowed to react at room temperature for 1 hour.

Each well was washed with 0.05% tween20/PBS, and then 50 μL/well of Goat anti-Human IgG(H+L)-POD (American Qualex) which was diluted 5000-fold in 1% BSA/PBS was added and allowed to react at room temperature for 1 hour. Each well was washed with PBS, and then 50 μL/well of ABTS substrate solution was added, and allowed to react at room temperature. After sufficient color development was confirmed, 50 μL/well of 5% SDS solution was added to terminate the reaction, and absorbance at 415 nm was measured.

As a result, it was revealed that RA15-7 antibody and LK26 antibody compete with each other for binding to FOLR1. Meanwhile, it was also revealed that for binding to FOLR1, RA15-7 antibody and MOv18 antibody do not compete with each other and LK26 antibody and MOv18 antibody do not compete with each other.

Example 22

Gene Cloning of Heavy Chain and Light Chain Variable Regions of RA15-7 Antibody

Using an RNAiso plus (Takara) in accordance with the accompanying instructions, the hybridoma RA15-7 washed with PBS was dissolved, and total RNA was prepared. The total RNA thus obtained was dissolved in DEPC treated water (Invitrogen).

Subsequently, mRNA was purified from the total RNA thus obtained using an Oligotex-dT30<Super> mRNA Purification Kit (From Total RNA) (Takara) in accordance with the accompanying instructions. Further, cDNA was prepared from the purified mRNA using a SMART RACE cDNA Amplification Kit (Clontech) in accordance with the accompanying instructions.

The resulting cDNA as a template and RatIgG1H-A (SEQ ID NO. 18) and RatIgG1H-B (SEQ ID NO. 19) primers for rat IgG1 heavy chain gene and Ratk-A (SEQ ID NO. 20) and Ratk-B (SEQ ID NO. 21) primers for rat light chain (κ chain) gene were used to amplify each gene by PCR. The amplified gene was subcloned, followed by sequencing analysis.

As a result, it was revealed that the heavy chain variable region of RA15-7 antibody comprising a signal sequence has the nucleotide sequence represented by SEQ ID NO. 22 and the amino acid sequence represented by SEQ ID NO. 23, and the light chain variable region of RA15-7 antibody comprising a signal sequence has the nucleotide sequence represented by SEQ ID NO. 24 and the amino acid sequence represented by SEQ ID NO. 25.

It was also revealed that based on the report of Kabat et al. [Sequences of Proteins of Immunological Interest, US Dept. Health and Human Services (1991)], the heavy chain variable region of RA15-7 antibody containing no signal sequence has the nucleotide sequence represented by SEQ ID NO. 26 and the amino acid sequence represented by SEQ ID NO. 27, and the light chain variable region of RA15-7 antibody containing no signal sequence has the nucleotide sequence represented by SEQ ID NO. 28 and the amino acid sequence represented by SEQ ID NO. 29.

Furthermore, it was revealed that the amino acid sequences of CDR1, CDR2, and CDR3 of the heavy chain of RA15-7 antibody are represented by SEQ ID NOs. 30, 31, and 32, respectively. It was also revealed that the amino acid sequences of CDR1, CDR2, and CDR3 of the light chain of RA15-7 antibody are represented by SEQ ID NOs. 33, 34, and 35, respectively.

Example 23

Construction of Rat/Human Chimeric RA15-7 Antibody-Expressing Vector

The rat/human chimeric RA15-7 antibody-expressing vector was prepared by linking the genes of RA15-7 antibody heavy chain and light chain variable regions to the genes of human IgG1 heavy chain and κ chain constant region. pKANTEX93 containing the gene of human IgG1κ constant region was used as a vector.

First, the gene of RA15-7 antibody light chain variable region was amplified by PCR using RA15-7-VLF (SEQ ID NO. 36) and RA15-7-VLR (SEQ ID NO. 37) primers. The purpose sequence was purified from the PCR product, and ligated to pKANTEX93 that had been treated with EcoRI and BsiWI.

In the same manner, the gene of RA15-7 antibody heavy chain variable region was amplified by PCR using RA15-7-VHF (SEQ ID NO. 38) and RA15-7-VHR (SEQ ID NO. 39) primers. The purpose sequence was purified from the PCR product, and ligated to the RA15-7 antibody light chain variable region-ligated pKANTEX93 which had been treated with NotI and ApaI. This vector was used as a rat/human chimeric RA15-7 (hereinafter, referred to as ChRA15-7) antibody-expressing vector.

Example 24

Preparation of Cells Expressing ChRA15-7 Antibody and ChRA15-7 Antibody Having a Sugar Chain Containing No Fucose CHO/DG44 cells were used for the preparation of ChRA15-7 antibody-expressing cells to which a sugar chain containing fucose is added (hereinafter, referred to as "conventional"). In addition, CHO/Ms704 cells were used for the preparation of ChRA15-7 (hereinafter, referred to as ChRA15-7DF) antibody having a sugar chain containing no fucose (hereinafter, referred to as "defucosylated"). The vector prepared in Example 23 was used as the expression vector. Typically, subculture, gene transfection, selection of drug-resistant cells and collection of culture supernatant were carried out in the same manner as in Example 7.

Example 25

Purification of ChRA15-7 Antibody and ChRA15-7DF Antibody

Purifications of ChRA15-7 antibody and ChRA15-7DF antibody from the recovered culture supernatant were carried out in the same manner as in Example 8. Irrespective of the conventional or defucosylated type, the concentration was calculated from absorbance index at 280 nm of 1.37.

Example 26

Preparation of CDC Enhancement Technology-Applied Defucosylated Antibody-Expressing Vector In order to prepare CDC enhancement technology-applied defucosylated antibody, the antibody heavy chain constant region of pKANTEX93 was modified, referring to the reports of WO2007/011041 and WO2011/108502. The nucleotide sequence and amino acid sequence after modification are represented by SEQ ID NOs. 40 and 41, respectively. The light chain variable region and heavy chain variable region of RA15-7 antibody and MORAb-003 antibody (WO2005/080431) were transfected into this vector to prepare CDC enhancement technology-applied defucosylated ChRA15-7 (hereinafter, referred to as ChRA15-7Acc) antibody and MORAb-003 (hereinafter, referred to as MORAb-003Acc) antibody-expressing vectors.

Example 27

Preparation of ChRA15-7Acc Antibody and MORAb-003Acc Antibody-Expressing Cells CHO/Ms704 cells were used for the preparation of ChRA15-7Acc antibody and MORAb-003Acc antibody-expressing cells. ChRA15-7Acc antibody and MORAb-003Acc antibody-expressing vectors prepared in Example 26 were used as expression vectors. Typically, subculture, gene transfection, selection of drug-resistant cells and collection of culture supernatant were carried out in the same manner as in Example 7.

Example 28

Purification of ChRA15-7Acc Antibody and MORAb-003Acc Antibody

Purifications of ChRA15-7Acc antibody and MORAb-003Acc antibody from the collected culture supernatant were carried out in the same manner as in Example 8. The concentrations were calculated from absorbance index at 280 nm of 1.34 and 1.60 for ChRA15-7Acc antibody and MORAb-003Acc antibody, respectively.

Example 29

Affinity Measurement of ChRA15-7Acc Antibody (Surface Plasmon Resonance Method)

The affinities of ChRA15-7Acc antibody and MORAb-003 antibody for FOLR1 were measured by a surface plasmon resonance method. The measurement was carried out in the same manner as in Example 16, except that a Human Antibody Capture Kit (GE Healthcare) was immobilized onto the CM5 chip by amine coupling and FOLR1-mycHis prepared by five-step dilution (12.3, 37, 111, 333, 1000 ng/mL) was applied as an analyte.

As a result, the affinities (KD, calculated from kd/ka) of ChRA15-7Acc antibody and MORAb-003 antibody for FOLR1-mycHis were 0.57 nmol/L and 57 nmol/L, respectively (Table 1), indicating that the rat/human chimeric antibody ChRA15-7Acc prepared from RA15-7 antibody is an antibody showing high affinity for FOLR1, compared to the conventional antibody MORAb-003.

TABLE 1

|  | ka $(\times 10^5 \, (\text{mol/L} \cdot \text{sec})^{-1})$ | kd $(\times 10^{-3} \, (\text{sec})^{-1})$ | KD $(\times 10^{-9} \, \text{mol/L})$ |
|---|---|---|---|
| ChRA15-7Acc | 17.6 | 1.00 | 0.57 |
| MORAb-003 | 4.58 | 25.9 | 57 |

Example 30

Affinity Evaluation of ChRA15-7DF Antibody (Western Blotting)

The reactivities of ChRA15-7DF antibody and MORAb-003 antibody were evaluated by Western blotting.

First, FOLR1-mycHis was suspended in Lane Marker Reducing Sample Buffer and Lane Marker Non-Reducing Sample Buffer (Thermo), and incubated at 100° C. for 5 minutes to prepare reducing FOLR1-mycHis and non-reducing FOLR1-mycHis. SDS-PAGE of the reducing and non-reducing FOLR1-mycHis prepared by five-step dilution (0.5, 2.7, 13, 67, 333 ng/lane) was carried out using gel e-PAGEL (ATTO) for SDS-PAGE.

Subsequently, the electrophoresed gel was stacked on a PVDF membrane (Millipore) and filter papers pre-soaked in a transfer buffer (12.1 g of Tris, 14.4 g of glycine, 200 mL of methanol/1 L sterile water) were placed on the top and bottom thereof, and allowed to transfer.

Thereafter, the PVDF membrane was blocked with 1% globulin-free BSA (Nacalai)/TBS. Subsequently, ChRA15-7DF antibody and MORAb-003 antibody prepared at a concentration of 5 µg/mL using 1% globulin-free BSA/TBS were reacted with the PVDF membrane at room temperature for 1 hour.

This PVDF membrane was washed, and then Goat anti-Human IgG(H+L)–POD (American Qualex) diluted with 1% globulin-free BSA/TBS was reacted at room temperature for 1 hour.

The PVDF membrane was washed again, and reacted with Chemi-Lumi One Super (Nacalai) for 1 minute, and the fluorescence of the PVDF membrane was detected using ImageQuant LAS 4000 mini (GE Healthcare).

As a result, both ChRA15-7DF antibody and MORAb-003 antibody showed reactivity only to non-reducing FOLR1-mycHis, indicating that they are antibodies recognizing the conformational structure of FOLR1.

MORAb-003 antibody detected 67 ng or more of non-reducing FOLR1-mycHis whereas ChRA15-7DF antibody detected 2.7 ng or more of non-reducing FOLR1-mycHis.

That is, ChRA15-7DF antibody showed a remarkably high sensitivity in the detection of non-reducing FOLR1-mycHis, compared to MORAb-003 antibody.

Example 31

Comparison of Antibody-Dependent Cellular Cytotoxic (ADCC) Activity Between ChRA15-7DF Antibody and MORAb-003 Antibody ADCC activity against ovarian cancer cell lines was evaluated. The target cancer cell lines [Caov-3 (ATCC NO. HTB-75), PA-1 (ATCC NO. CRL-1572), IGR-OV1 (National Cancer Institute), SKOV-3 (ATCC NO. HTB-77), RMG-1 (JCRB cell No. JCRB0172), OVCAR-3 (ATCC NO. HTB-161)] were detached from culture flasks using 0.02% EDTA solution (Nacalai), and prepared at a density of $1 \times 10^4$ cells/50 µL using an ADCC measurement medium [phenol red-free RPMI1640 (GIBCO), 5% inactivated dFCS (GIBCO), 50 µg/mL gentamycin (Nacalai)] and used as target cell solutions.

Subsequently, the heparin-treated peripheral blood of a normal healthy donor was loaded in a LeucoSep lymphocyte separation tube (Greiner) packed with Lymphoprep (Cosmo Bio), followed by centrifugation at 1000×g at room temperature for 20 minutes. After centrifugation, the serum fraction was removed, and a PBMC layer was collected. Cells were washed with the ADCC measurement medium. PBMC was prepared at a density of 2.5×10$^5$ cells/50 μL using the ADCC measurement medium, and used as an effector cell solution.

The antibody solution was first prepared at concentrations of 0.1, 1, 10, 100, and 1000 ng/mL using ADCC measurement medium, in order to make its final concentrations at 0.033, 0.33, 3.3, 33, and 333 ng/mL.

Each 50 μL/well of the target cell solution, effector cell solution, and antibody solution thus prepared was mixed in a U-bottom 96-well plate to a total volume of 150 μL/well. Each well was mixed well, and then cells were precipitated by centrifugation at 50×g and room temperature for 5 minutes, and allowed to react at 37° C. for 4 hours.

Subsequently, each well was stirred well, and cells were further precipitated by centrifugation. 50 μL of the supernatant of each well was dispensed in a new ELISA plate. The lactate dehydrogenase (LDH) activity in the dispensed supernatant was measured by CytoTox 96 Non-Radioactive Cytotoxicity Assay (Promega). Manipulations were carried out in accordance with the accompanying instructions.

ADCC activity was calculated by the following Equation after subtracting the measured value of LDH activity of the well containing only the ADCC measurement medium from the measured value of LDH activity of each well, and using the value as the corrected measured value of LDH activity of each well.

$$ADCC \text{ activity } (\%) = 100 \times \frac{\text{Exp} - ET\ spo}{T\ \text{total} - D - T\ spo} \quad \text{Formula 1}$$

Wherein Exp indicates the corrected measured value of LDH activity of each sample, ET spo indicates the corrected measured value of LDH activity of the well containing the mixture of the effector cell solution and the target cell solution, T total indicates the corrected measured value of LDH activity of the well containing the mixture of the target cell and Lysis solution accompanied with CytoTox 96 Non-Radioactive Cytotoxicity Assay, D indicates the corrected measured value of LDH activity of Lysis Solution, and T spo indicates the corrected measured value of LDH activity of the well of only the target cell.

As a result, ChRA15-7DF antibody showed ADCC activity at a lower concentration than MORAb-003 antibody, and its maximum cytotoxicity was also high. In addition, ChRA15-7DF antibody showed ADCC activity at a lower concentration than defucosylated MORAb-003 (MORAb-003DF) antibody, and its maximum cytotoxicity was also high.

Therefore, it was revealed that ChRA15-7DF antibody had higher ADCC activity than MORAb-003DF antibody which was prepared by applying the ADCC enhancement technology (defucosylation) to the conventional anti-FOLR1 humanized antibody (MORAb-003). Also, it was suggested that ChRA15-7DF antibody is more useful as a therapeutic antibody for ovarian cancer than MORAb-003 and MORAb-003DF.

Example 32

Construction of Rat/Human Chimeric FOLR1-Expressing Vector

In order to analyze the antibody epitope, three types of rat/human chimeric FOLR1-mycHis (hereinafter, referred to as Rat1-FOLR1-mycHis, Rat2-FOLR1-mycHis, and Rat4-FOLR1-mycHis) were prepared by substituting a part of the nucleotide sequence of FOLR1-mycHis with rat FOLR1 (NM_133527).

Rat1-FOLR1-mycHis was prepared by substituting the amino acid sequence at positions 3 to 28 in the human FOLR1 amino acid sequence represented by SEQ ID NO. 1 with the amino acid sequence at positions 3 to 26 in the rat FOLR1 amino acid sequence represented by SEQ ID NO. 102, and adding myc and His tags at the C-terminus.

Rat2-FOLR1-mycHis was prepared by substituting the amino acid sequence at positions 55 to 62 in the human FOLR1 amino acid sequence represented by SEQ ID NO. 1 with the amino acid sequence at positions 53 to 60 in the rat FOLR1 amino acid sequence represented by SEQ ID NO. 102, and adding myc and His tags at the C-terminus.

Rat4-FOLR1-mycHis was prepared by substituting the amino acid sequence at positions 91 to 95 in the human FOLR1 amino acid sequence represented by SEQ ID NO. 1 with the amino acid sequence at positions 89 to 93 in the rat FOLR1 amino acid sequence represented by SEQ ID NO. 102, and adding myc and His tags at the C-terminus.

The nucleotide sequences of Rat1-FOLR1-mycHis, Rat2-FOLR1-mycHis, and Rat4-FOLR1-mycHis are represented by SEQ ID NO. 42, SEQ ID NO. 43, and SEQ ID NO. 44, respectively, and the amino acid sequences thereof are represented by SEQ ID NO. 45, SEQ ID NO. 46, and SEQ ID NO. 47, respectively.

Each gene was synthesized, and substituted with the FOLR1-mycHis gene on the FOLR1-mycHis-expressing vector of Example 9, thereby constructing Rat1-FOLR1-mycHis, Rat2-FOLR1-mycHis, and Rat4-FOLR1-mycHis-expressing vectors.

Example 33

Preparation of Rat1-FOLR1-mycHis, Rat2-FOLR1-mycHis, and Rat4-FOLR1-mycHis Expressing Cells CHO/DG44 cells were used in the preparation of Rat1-FOLR1-mycHis, Rat2-FOLR1-mycHis, and Rat4-FOLR1-mycHis expressing cells. The vectors prepared in Example 32 were used as each expression vector. Typically, subculture, gene transfection, selection of drug-resistant cells and collection of culture supernatant were carried out in the same manner as in Example 7.

Example 34

Purification of Rat1-FOLR1-mycHis, Rat2-FOLR1-mycHis, and Rat4-FOLR1-mycHis

Purifications of Rat1-FOLR1-mycHis, Rat2-FOLR1-mycHis, and Rat4-FOLR1-mycHis were carried out in the same manner as in Example 11. All concentrations were calculated from absorbance index at 280 nm of 2.8.

Example 35

Analysis of Epitope of ChRA15-7Acc Antibody (ELISA)

FOLR1-mycHis prepared in Example 11 and Rat1-FOLR1-mycHis, Rat2-FOLR1-mycHis, and Rat4-FOLR1-mycHis prepared in Example 34 were used to evaluate the reactivities of ChRA15-7Acc antibody, MORAb-003 antibody, and MOv18 antibody.

First, each 50 µL/well of FOLR1-mycHis, Rat1-FOLR1-mycHis, Rat2-FOLR1-mycHis, and Rat4-FOLR1-mycHis which were prepared at a concentration of 10 µg/mL using PBS was comprising in a 96-well plate for ELISA, and then incubated at 4° C. overnight. Each well was washed with PBS, and then 200 µL/well of 1% BSA/PBS was added at room temperature for 1 hour for blocking.

Each well was washed with PBS again, and then each 50 µL/well of ChRA15-7Acc antibody, MORAb-003 antibody, and MOv18 antibody which were prepared by seven-step 3-fold serial dilution from 10000 ng/mL in 1% BSA/PBS (14, 41, 123, 370, 1111, 3333, 10000 ng/mL) was added, and reacted at room temperature for 1 hour.

Each well was washed with 0.05% tween20/PBS, and 50 µL/well of Goat anti-human IgG(H+L)-POD (American Qualex) diluted 5000-fold in 1% BSA/PBS was added to the wells reacted with ChRA15-7Acc antibody or MORAb-003 antibody, and 50 µL/well of Polyclonal Rabbit Anti-Mouse IgG-POD (Dako) diluted 400-fold in 1% BSA/PBS was added to the well reacted with MOv18 antibody, and then reacted at room temperature for 1 hour.

Each well was washed with PBS, and then 50 µL/well of ABTS substrate solution was added, and allowed to react at room temperature. After sufficient color development was confirmed, 5% SDS solution was added to terminate the reaction, and absorbance at 415 nm was measured.

The results are shown in Table 2. White circle indicates that reaction occurred, and x indicates that no reaction occurred. ChRA15-7Acc antibody, MORAb-003 antibody, and MOv18 antibody reacted to FOLR1-mycHis. ChRA15-7Acc antibody and MORAb-003 antibody reacted to Rat1-FOLR1-mycHis, but MOv18 antibody did not.

MORAb-003 antibody and MOv18 antibody reacted to Rat2-FOLR1-mycHis, but ChRA15-7Acc antibody did not. ChRA15-7Acc antibody and MOv18 antibody reacted to Rat4-FOLR1-mycHis, but MORAb-003 antibody did not.

Taken together, it was shown that MOv18 antibody, ChRA15-7Acc antibody, and MORAb-003 antibody recognize the sequence comprising the region, in which the FOLR1-mycHis amino acid sequence was substituted with the rat-type, in Rat1-FOLR1-mycHis, Rat2-FOLR1-mycHis, and Rat4-FOLR1-mycHis, respectively.

Specifically, it was suggested that MOv18 antibody, ChRA15-7Acc antibody, and MORAb-003 antibody recognize the amino acid sequence at positions 3 to 28, the amino acid sequence at positions 55 to 62, and the amino acid sequence at positions 91 to 95, of FOLR1-mycHis, respectively.

TABLE 2

| | MORAb-003 antibody | ChRA15-7Acc antibody | MOv18 antibody |
|---|---|---|---|
| FOLR1-mycHis | ○ | ○ | ○ |
| Rat1-FOLR1-mycHis | ○ | ○ | X |
| Rat2-FOLR1-mycHis | ○ | X | ○ |
| Rat4-FOLR1-mycHis | X | ○ | ○ |

Example 36

Design of Humanized RA15-7 Antibody Heavy Chain and Light Chain Variable Regions First, in order to graft amino acid sequences of RA15-7 heavy chain CDR1, CDR2, and CDR3 represented by SEQ ID NOs. 30, 31, and 32, respectively, an amino acid sequence of framework region (FR) in heavy chain variable region of a human antibody was selected. The previously known human antibody sequence having high homology to the FR sequence of RA15-7 heavy chain was searched using a database of Ig Germline Genes provided by The National Center for Biotechnology Information.

As a result, FR of IGVH3-72 was selected, because IGVH3-72 is a human antibody sequence having the highest homology. To design HV0, the amino acid sequences of CDR1, CDR2, CDR3 of RA15-7 heavy chain, represented by SEQ ID NOs. 30, 31, and 32, were grafted into the proper region of the FR sequence of the human antibody thus determined.

Subsequently, the amino acid sequences of framework regions (FR) in light chain variable region of a human antibody were selected, to which amino acid sequences of RA15-7 light chain CDR1, CDR2, and CDR3 represented by SEQ ID NOs. 33, 34, and 35, respectively were grafted.

Kabat et al., have classified VL of the conventionally known various human antibodies into subgroups (HSG I-IV) based on the homology of their amino acid sequences, and reported the consensus sequences for each of the subgroups [Sequences of Proteins of Immunological Interest, US Dept. Health and Human Services (1991)].

Therefore, the homology search of the consensus amino acid sequences of FR of VL subgroups I-IV (hSGI-hSGIV) of human antibodies with the FR sequence of RA15-7 light chain was conducted. As a result, hSGI was the consensus sequence of human antibody light chain having the highest homology. To design LV0, the amino acid sequences (SEQ ID NOs. 33, 34, and 35) of CDR1, CDR2, and CDR3 of RA15-7 light chain were grafted to an appropriate position of the FR sequence of the human antibody thus determined as described above.

Subsequently, predicted three-dimensional structures of the variable region of the above designed humanized antibody (HV0LV0) composed of HV0 and LV0, and ChRA15-7 antibody were constructed using a computer modeling technique, and compared to each other. Discovery Studio (Accelrys) was used for construction of the three-dimensional structure and visualization of coordinate data.

As a result of the comparison of the three-dimensional structures, the residues expected to significantly contribute to antigen binding activity such as maintenance of CDR loop structure or the like, the residues expected to contribute to maintenance of the entire structure by hydrophobic interaction or the like, and the residues expected to potentially have high antigenic risk by exposing at the molecule's surface were identified as candidate residues for modifications.

One or more of the selected modification candidate residues were substituted with the amino acid residues which were present at the corresponding sites of ChRA15-7 antibody, so as to design each modified product of the humanized antibody. As the heavy chain variable region of the modified humanized RA15-7 antibody containing no signal sequence, HV0, HV2, HV3, HV4, HV5, HV6, HV7, HV8, and HV10 were designed according to the amino acid sequences shown in FIG. 1.

In the same manner, as the light chain variable region of the modified humanized RA15-7 antibody containing no signal sequence, LV0, LV2, LV3, LV4, and LV6 were designed according to the amino acid sequences shown in FIG. 2.

Example 37

Construction of Modified Humanized RA15-7 Antibody-Expressing Vector

HV0, HV2, HV3, HV4, HV5, HV6, HV7, HV8, HV10, LV0, LV2, LV3, LV4, and LV6 (SEQ ID NOs. 48-61) which are the nucleotide sequences of heavy chain and light chain variable regions of the modified humanized RA15-7 antibody containing no signal sequence thus designed were ligated into pKANTEX93, in the same manner as the construction of ChRA15-7 expression vector (Example 23).

Example 38

Preparation of Modified Humanized RA15-7 Antibody-Expressing Cells

FUT8 gene double-knockout CHO-K1 line (Tsukahara et al., Animal Cell Technology: Basic & Applied Aspects, 175-183, 2006) was used in the preparation of modified humanized RA15-7 antibody-expressing cells. Each of the modified humanized antibody-expressing vectors prepared in Example 37 was transiently transfected using FreeStyle MAX CHO Expression System (Invitrogen) according to the manufacturer's instruction. These cells were cultured for one week, and the culture supernatant was collected.

Example 39

Purification of Modified Humanized RA15-7 Antibody

Each of the modified humanized antibodies was purified from the culture supernatant collected in Example 38 using MabSelect SuRe (GE Healthcare). In detail, a sterile solution, 0.1 M citrate solution (pH 3.6), and 0.2 M Na borate/150 mmol/L NaCl solution (pH 7.5) were serially applied to the column packed with carriers for its equilibration.

The culture supernatant was applied to the column, and then the column was washed with 0.2 M Na borate/150 mmol/L NaCl solution (pH 7.5). 0.1 M citrate solution (pH 3.6) was used for elution. The eluted fractions were rapidly neutralized with 1 M Tris-HCl (pH 9.0).

Absorbance (280 nm) of each fraction was measured, and serial fractions having high measured value were collected as antibody fractions. They were subjected to dialysis using a buffer (10 mmol/L citric acid, 150 mmol/L NaCl, pH 6.0), and passed through a 0.22 μm-filter to prepare each purified antibody of the modified humanized antibodies. The concentration was calculated from absorbance index at 280 nm of 1.4.

Example 40

Affinity Measurement of Modified Humanized RA15-7 Antibody (Surface Plasmon Resonance Method)

In the same manner as in Example 29, affinity of each modified humanized antibody for FOLR1 was measured by the surface plasmon resonance method.

As a result, it was shown that affinities of 5 types of the modified humanized RA15-7 antibodies (HV7LV3, HV10LV2, FIV10LV3, HV10LV4, and HV10LV6) for FOLR1-mycHis retained approximately 70% of the affinity of ChRA15-7Acc.

Example 41

Design of Cys Modified Product of the Modified Humanized RA15-7 Antibody HV7LV3 (HV7LV3-CDRH3-Cys101)

Cys(Cys101) is included in the heavy chain CDR3 of the modified humanized RA15-7 antibody HV7LV3. In the substitution of Cys101 with other amino acid, total 14 types of amino acids of Met, Gly, Asp, Ser, Tyr, Ala, Ile, Val, Thr, Phe, Arg, Trp, Pro, and Gln were selected as candidates for amino acid modification, considering the factors such as a molecular structure, hydrophobicity, which are similar to those of Cys, and amino acids which are simple structure.

Example 42

Construction of HV7LV3-CDRH3-Cys101 Modified Antibody-Expressing Vector

A HV7LV3-CDRH3-Cys101 modified antibody-expressing vector was constructed. First, a vector ligated with an HV7 variable region gene (SEQ ID NO. 62) was used as a template. Genetic mutation was introduced for substitution of Cys101 with the candidate amino acid using a point mutation introduction kit [QuickChange II Site-Directed Mutagenesis Kit (Agilent Technologies)] in accordance with the accompanying instructions. The obtained DNA solution was transformed into XL1-Blue, and plasmids were extracted from the colonies thus formed.

The nucleotide sequence of the HV7 variable region containing no signal sequence, in which Cys101 was substituted with the candidate amino acid, is represented by Met (C101M_DNA): SEQ ID NO. 63, Gly (C101G_DNA): SEQ ID NO. 64, Asp (C101D_DNA): SEQ ID NO. 65, Ser (C101S_DNA): SEQ ID NO. 66, Tyr (C101Y_DNA): SEQ ID NO. 67, Ala (C101A_DNA): SEQ ID NO. 68, Ile (C101I_DNA): SEQ ID NO. 69, Val (C101V_DNA): SEQ ID NO. 70, Thr (C101T_DNA): SEQ ID NO. 71, Phe (C101F_DNA): SEQ ID NO. 72, Arg (C101R_DNA): SEQ ID NO. 73, Trp (C101W_DNA): SEQ ID NO. 74, Pro (C101P_DNA): SEQ ID NO. 75, or Gln (C101Q_DNA): SEQ ID NO. 76, respectively.

The amino acid sequence of the HV7 variable region containing no signal sequence, in which Cys101 was substituted with the candidate amino acid, is represented by Met (C101M_AA): SEQ ID NO. 77, Gly (C101G_AA): SEQ ID NO. 78, Asp (C101D_AA): SEQ ID NO. 79, Ser (C101S_AA): SEQ ID NO. 80, Tyr (C101Y_AA): SEQ ID NO. 81, Ala (C101A_AA): SEQ ID NO. 82, Ile (C101I_AA): SEQ ID NO. 83, Val (C101V_AA): SEQ ID NO. 84, Thr (C101T_AA): SEQ ID NO. 85, Phe (C101F_AA): SEQ ID NO. 86, Arg (C101R_AA): SEQ ID NO. 87, Trp (C101W_AA): SEQ ID NO. 88, Pro (C101P_AA): SEQ ID NO. 89, or Gln (C101Q_AA): SEQ ID NO. 90, respectively.

Subsequently, the heavy chain variable region gene HV7 of the HV7LV3 antibody-expressing vector was substituted with the HV7 variable region gene in which Cys101 was substituted with the candidate amino acid. NotI and ApaI recognition sites were used for recombination. The obtained vector was used as the HV7LV3-CDRH3-Cys101 modified antibody-expressing vector.

Example 43

Preparation and Culture of HV7LV3-CDRH3-Cys101 Modified Antibody Expressing Cells HV7LV3-CDRH3-Cys101 modified antibody expressing cells were prepared using the vector prepared in Example 42. Cell expression, gene transfection, and collection of culture supernatant were carried out in the same manner as in Example 38.

Example 44

Purification of HV7LV3-CDRH3-Cys101 Modified Antibody

Purification of HV7LV3-CDRH3-Cys101 modified antibodies and calculation of its concentration were carried out in the same manner as in Example 39.

Example 45

Affinity Measurement of HV7LV3-CDRH3-Cys101 Modified Antibody (Surface Plasmon Resonance Method)

Affinities of HV7LV3-CDRH3-Cys101 modified antibodies for FOLR1 were measured by the surface plasmon resonance method in the same manner as in Example 29.

As a result, it was shown that affinities of the antibodies in which Cys101 was modified with Ile(C101I), Val(C101V), Thr(C101T), Phe(C101F), Gln(C101Q), and Met(C101M), respectively for FOLR1-mycHis retained 50% or more of the affinity of ChRA15-7Acc antibody.

In detail, the affinities of the antibodies having C101I, C101V, C101T, C101F, C101Q, and C101M modifications were 73%, 55%, 88%, 80%, 64%, and 59% of the affinity of ChRA15-7Acc antibody, respectively (FIG. 3), indicating that the antibody having C101T modification (HuRA15-7CT) showed improved affinity compare to the HV7LV3 humanized modified antibody.

The nucleotide sequence and the amino acid sequence of the light chain variable region of HuRA15-7CT antibody with a signal sequence are represented by SEQ ID NOs. 91 and 92, respectively. Further, the nucleotide sequence and the amino acid sequence of the light chain variable region of HuRA15-7CT antibody without signal sequence are represented by SEQ ID NOs. 93 and 94, respectively.

Also, the nucleotide sequence and the amino acid sequence of the heavy chain variable region of HuRA15-7CT antibody with a signal sequence are represented by SEQ ID NOs. 95 and 96, respectively. Further, the nucleotide sequence and the amino acid sequence of the heavy chain variable region of HuRA15-7CT antibody without signal sequence are represented by SEQ ID NOs. 97 and 98, respectively.

Further, the amino acid sequences of heavy chain CDR1, CDR2, and CDR3 of HuRA15-7CT antibody are represented by SEQ ID NOs. 30, 31, and 99, respectively. The amino acid sequences of light chain CDR1, CDR2, and CDR3 of HuRA15-7CT antibody are represented by SEQ ID NOs. 33, 34, and 35, respectively.

Example 46

Construction of CDC Enhancement Technology-Applied Defucosylated HuRA15-7CT Antibody-Expressing Vector Construction of CDC enhancement technology-applied defucosylated HuRA15-7CT (hereinafter, referred to as HuRA15-7CTAcc) antibody-expressing vector was carried out using SEQ ID NO. 91 as the light chain variable region and SEQ ID NO. 95 as the heavy chain variable region in the same manner as in Example 26.

Example 47

Preparation of Defucosylated HuRA15-7CT Antibody-Expressing Cells and HuRA15-7CTAcc Antibody-Expressing Cells CHO/Ms704 was used in the preparation of defucosylated HuRA15-7CT (hereinafter, referred to as HuRA15-7CTDF) antibody-expressing cells and HuRA15-7CTAcc antibody-expressing cells. As an expression vector, HuRA15-7CT antibody-expressing vector prepared in Example 42 or HuRA15-7CTAcc antibody-expressing vector prepared in Example 46 was used. Typically, subculture, gene transfection, selection of drug-resistant cells and collection of culture supernatant were carried out in the same manner as in Example 7.

Example 48

Purification of HuRA15-7CTDF Antibody and HuRA15-7CTAcc Antibody

Purification of HuRA15-7CTDF antibody and HuRA15-7CTAcc antibody from the culture supernatant was carried out in the same manner as in Example 8. The concentrations were calculated from absorbance index at 280 nm of 1.38 and 1.37 for HuRAL5-7CTDF antibody and HuRA15-7CTAcc antibody, respectively.

Example 49

Affinity Measurement of HuRA15-7CTAcc Antibody (Surface Plasmon Resonance Method)

In the same manner as in Example 29, affinity of HuRA15-7CTAcc antibody for FOLR1 was measured by the surface plasmon resonance method.

As a result, with respect to the affinity of HuRA15-7CTAcc antibody for FOLR1-mycHis, KD value was 0.65 nmol/L (Table 3). Therefore, it was shown that this antibody binds to FOLR1 at remarkably higher affinity than MORAb-003 antibody (KD=57 nmol/L, Example 29).

TABLE 3

| | ka $(\times 10^5 (mol/L \cdot sec)^{-1})$ | kd $(\times 10^{-3} (sec)^{-1})$ | KD $(\times 10^{-9} mol/L)$ |
|---|---|---|---|
| HuRA15-7CTAcc | 16.8 | 1.08 | 0.65 |

Example 50

Evaluation of Specificities of HuRA15-7CTDF Antibody and ChRA15-7DF Antibody (ELISA)

The reactivities of HuRA15-7CTDF antibody, ChRA15-7DF antibody, and MORAb-003DF antibody for FOLR1-Fc, FOLR2-Fc, FOLR3-Fc, and cynomolgus monkey FOLR1-Fc were evaluated.

First, each 50 µL/well of FOLR1-Fc, FOLR2-Fc, FOLR3-Fc, and cynomolgus monkey FOLR1-Fc which were prepared at a concentration of 2 µg/mL using PBS was added in a 96-well plate for ELISA and incubated at 4° C. overnight. It was washed with PBS, and then 200 µL/well of 1% BSA/PBS wad added at room temperature for 1 hour for blocking. It was washed with PBS again, and each 50 µL/well of HuRA15-7CTDF antibody, ChRA15-7DF antibody, MORAb-003DF antibody, and defucosylated anti-DNP human IgG1 (DN-PDF) antibody as a negative control which were prepared by seven-step dilution (1.4, 4.1, 12, 37, 111, 333, 1000 ng/mL) in 1% BSA/PBS was added, and allowed to react at room temperature for 1 hour.

Each well was washed with 0.05% tween20/PBS, and then 50 μL/well of Goat anti-Human kappa-HRP (Southern Biotech) which was diluted 2000-fold using 1% BSA/PBS was added and allowed to react at room temperature for 1 hour. Each well was washed with PBS, and then 50 μL/well of ABTS substrate solution was added, and allowed to react at room temperature. After sufficient color development was confirmed, 5% SDS solution was added to terminate the reaction, and absorbance at 415 nm was measured.

As a result, it was shown that binding activities of HuRA15-7CTDF antibody, ChRA15-7DF antibody, and MORAb-003DF antibody for human and cynomolgus monkey FOLR1-Fc were equivalent, but they did not bind to FOLR2-Fc and FOLR3-Fc (FIG. 4). That is, it was shown that the HuRA15-7CTDF antibody, ChRA15-7DF antibody, and MORAb-003DF antibody were human and cynomolgus monkey FOLR1-specific antibodies.

Example 51

Immunohistochemistry by HuRA15-7CTAcc Antibody

The frozen human normal tissue array embedded in OCT compound (cerebrum, cerebellum, heart, lung, stomach, small intestine, liver, pancreas, salivary gland, kidney, thyroid, adrenal gland, skeletal muscle, spleen, ovary, uterus, placenta, skin, mammary gland) was subjected to Immunohistochemistry (IHC) using HuRA15-7CTAcc and DNPDF antibody as a negative control.

First, acetone fixation was carried at −20° C. for 5 minutes, and then air drying was carried for 10 minutes. Then, endogenous peroxidase was inactivated with PBS containing 0.1% $NaN_3$ and 0.3% $H_2O_2$ at room temperature. Subsequently, endogenous biotin was inactivated using a biotin blocking system (Daco).

Further, blocking was carried out using 1% BSA/PBS. Subsequently, HuRA15-7CTAcc antibody, MORAb-003 antibody, and DNPDF antibody prepared at a concentration of 1 μg/mL were reacted at room temperature for 1 hour, and PBS washing was carried out. Peroxidase-labeled streptavidin (Nichirei) was added, and reacted for 5 minutes, and PBS washing was carried out. DAB Tablet (Wako) prepared using 0.02% $H_2O_2$/PBS was added, and reacted for 10 minutes for color development. Mayer's Hematoxylin (Wako) was reacted for approximately 2 seconds. After washing with running water, the nuclei were stained.

The stained sample was treated with 70% ethanol for 5 minutes, 95% ethanol for 5 minutes, and 100% ethanol for 5 minutes, and then 100% ethanol three times. Subsequently, 100% xylene treatment was carried out for 5 minutes, and this manipulation was repeated three times, followed by penetration. Finally, it was mounted with Entellan®new (Merck).

The result of examination of the stained sample showed that lung (aveolar), stomach (mucous membrane), small intestine (mucous membrane, lamina muscularis mucosae), pancreas (duct, acinar cell), liver (bile duct), salivary gland (acinar cell, duct), kidney (uriniferous tubules, glomerulus), adrenal gland (cortical cell, interstitial tissue), thyroid (follicle, parafollicular cell), mammary gland (acinus), uterus (endocervical epithelium), ovary (epithelium), placenta (syncytial trophoblast), skin (sweat gland) were positive for staining by HuRA15-7CTAcc antibody, as reported in the literature [Cancer Res, 1992. 52(23): p. 6708-11., Int J Cancer, 2006. 119(2): p. 243-50.].

Subsequently, 8 cases of human ovarian cancer tissues (4 cases of serous cystadenocarcinoma, 1 case of serous cystadenoma, 2 cases of mucinous cystadenocarcinoma, 1 case of borderline mucinous cystadenoma) were subjected to the same staining. Further, MORAb-003 antibody was also used for staining, in addition to HuRA15-7CTAcc antibody and the negative control DNPDF antibody.

As a result, it was shown that five out of five cases of the serous type (100%) and one out of three cases of the mucinous type (33%) can be stained with HuRA15-7CTAcc antibody and MORAb-003 antibody. The stained regions of the tissue samples by both antibodies were identical to each other, indicating that the specificities of both antibodies to ovarian cancer are identical. It was also revealed that the staining of HuRA15-7CTAcc antibody is stronger than that of MORAb-003 antibody.

Subsequently, staining intensity of the stained sample was quantified by H-score. With respect to H-score, the staining intensity of the positively stained cells of the cancer cells was classified into four categories, and the percentage (%) of the positive cancer cells at each score was determined by 5% assessment interval, and then the overall score was obtained by multiplying each score by the percentage of the positive cancer cells.

As a result, with respect to 4 cases of serous cystadenocarcinoma, 1 case of serous cystadenoma, and 1 case of mucinous cystadenocarcinoma which were stained with both MORAb-003 antibody and HuRA15-7CTAcc antibody, HuRA15-7CTAcc antibody showed higher H-score than MORAb-003 antibody in all samples. Meanwhile, because 1 case of mucinous cystadenocarcinoma and 1 case of borderline mucinous cystadenoma were not stained with any antibodies, their H-score was 0.

Taken together, it was suggested that the binding of HuRA15-7CTAcc antibody to FOLR1 expressed in ovarian cancer is stronger than that of the conventional ovarian cancer therapeutic antibody MORAb-003.

Example 52

Evaluation of ADCC Activity of Rat/Human Chimeric Antibody and Humanized Antibody ChRA15-7Acc antibody, CDC enhancement technology-applied defucosylated HV7LV3 human IgG1 (HuRA15-7Acc) antibody, and HuRA15-7CTAcc antibody were used to evaluate their ADCC activity against ovarian cancer cell lines in the same manner as in Example 31.

As a result, it was shown that ADCC activities of HuRA15-7Acc antibody and HuRA15-7CTAcc antibody against SKOV-3 cell and OVCAR-3 cell derived from platinum-resistant ovarian cancer were equivalent to that of ChRA15-7Acc antibody (FIG. 5).

Example 53

Evaluation of CDC Activity of Rat/Human Chimeric Antibody and Humanized Antibody CDC activity against ovarian cancer cell line was evaluated. IGR-OV1 as a target cancer cell line was detached from a culture flask using 0.02% EDTA solution (Nacalai), and prepared using the CDC measurement medium [phenol red-free RPMI1640 (GIBCO), 1.4% BSA (SIGMA)] at a density of $1\times10^4$ cells/50 µL, which was used as a target cell solution.

Subsequently, freeze-dried human serum (SIGMA) was dissolved in 1 mL of purified water, and 1 mL of the CDC measurement medium was added thereto, and used as a complement solution. In order to prepare the antibody solutions at final concentrations of 0.032, 0.16, 0.8, 4.0, 20, and 100 µg/mL, HuRA15-7CTAcc antibody, HuRA15-7CTDF antibody, ChRA15-7Acc antibody, ChRA15-7DF antibody, and MORAb-003 were first prepared at a concentration of 0.096, 0.48, 2.4, 12, 60, and 300 µg/mL using the CDC measurement medium.

Each 50 µL/well of the target cell solution, complement solution, and antibody solution thus prepared were mixed in a 96-well flat-bottom plate and prepared at a total volume of 150 µL/well. Each well was mixed well, and allowed to react at 37° C. for 2 hours. Subsequently, each well was stirred well, and 30 µL/well of CellTiter 96 AQueous One Solution Cell Proliferation Assay (Promega) was added, stirred, and then allowed to react at 37° C. for approximately 1 hour. After sufficient color development was confirmed, absorbance at 415 nm was measured.

CDC activity was calculated by the following Equation after subtracting the measured absorbance of the well containing the mixture of the CDC measurement medium and the complement solution from the measured absorbance of each well and using the calculated value as the corrected absorbance of each well.

$$CDC \text{ activity } (\%) = 100 \times \frac{ST - Exp}{ST} \qquad \text{Formula 2}$$

Wherein Exp indicates the corrected absorbance of each sample, and ST indicates the corrected absorbance of the well containing the mixture of the target cell solution and the complement solution.

As a result, it was revealed that HuRA15-7CTAcc antibody and HuRA15-7CTDF antibody showed significantly high CDC activity, compared to ChRA15-7Acc antibody and ChRA15-7DF antibody, respectively [FIG. 6(a)]. It was also shown that HuRA15-7CTAcc antibody showed significantly high CDC activity, compared to MORAb-003 [FIG. 6(b)].

Example 54

Comparison of ADCC Activity Between HuRA15-7CTAcc Antibody and Conventional Anti-FOLR1 Antibody HuRA15-7CTAcc antibody, MORAb-003Acc antibody, and MORAb-003 antibody were used to evaluate their ADCC activity against ovarian cancer cell lines in the same manner as in Example 31.

As a result, HuRA15-7CTAcc antibody showed ADCC activity against SKOV-3 cell and OVCAR-3 cell derived from platinum-resistant ovarian cancer at lower concentrations than MORAb-003 and MORAb-003Acc antibodies (FIG. 7). That is, it was revealed that HuRA15-7CTAcc antibody has higher ADCC activity than MORAb-003Acc antibody which was prepared by applying the conventional ADCC enhancement technology (defucosylation) to the conventional anti-FOLR1 humanized antibody (MORAb-003).

Also, HuRA15-7CTAcc antibody showed ADCC activity against IGR-OV1 cell at lower concentration than MORAb-003 antibody. In addition, the ADCC activities of MORAb-003Acc antibody against ovarian cancer cell lines were reduced in this order of IGR-OV1, SKOV-3, and OVCAR-3 cells, but HuRA15-7CTAcc antibody showed almost equivalent ADCC activities against all ovarian cancer cell lines.

Taken together, it was suggested that HuRA15-7CTAcc antibody is more useful as the therapeutic antibody for platinum-resistant ovarian cancer, compared to the conventional antibody (MORAb-003) and the antibody (MORAb-003Acc) which was prepared by applying the conventional technology to the conventional antibody.

Example 55

Evaluation of Tumor Accumulation of HuRA15-7CTDF Antibody

In vivo kinetics of HuRA15-7CTDF antibody and MORAb-003DF antibody were analyzed by fluorescence imaging. First, HuRA15-7CTDF antibody and MORAb-003DF antibody were labeled using a XenoLight CF 770 Kit (HuRA15-7CTDF-770 antibody and MORAb-003DF-770 antibody), respectively, and the negative control DNPDF antibody was labeled using a XenoLight CF™ 680 Kit (DNPDF-680 antibody). Binding activity of each labeled antibody against SKOV-3 cell was confirmed by flow cytometry. Further, the labeling ratio of each antibody was determined in accordance with the accompanying instructions.

The cultured SKOV-3 cells were suspended in PBS, and transplanted subcutaneously to the lateral dorsal side of BALB/cMel-nu/nu mouse (female, 5-week-old, Clea-Japan). When tumors reached a volume of about 200 mm$^3$ after transplantation, the feed was replaced with alfalfa-free feed, and further raised for 1 week. Mice were randomly divided into 3 groups as 4 mice were assigned to each group, so that they were approximately equal in the average tumor volume.

Subsequently, 10 µg of HuRA15-7CTDF-770 antibody or MORAb-003DF-770 antibody was mixed with 2 µg of DNPDF-680 antibody, and its total volume was made to 200 µL with PBS and administered into the tail vein of the mice. The in vivo kinetics of the administered antibody was evaluated by photographing fluorescence intensity in the mice using an IVIS Imaging System (Caliper). The first photograph was taken after 4 hours from the administration, and then taken in constant time intervals.

Fluorescence intensity of HuRA15-7CTDF-770 antibody and MORAb-003DF-770 antibody in the photographed mice was corrected by fluorescence intensity of each antibody solution administered. Further, the ratio of the fluorescence intensity of HuRA15-7CTDF-770 antibody or MORAb-003DF-770 antibody to the fluorescence intensity of DNPDF-680 antibody as a mouse internal standard was calculated, and in vivo kinetics of each antibody was evaluated.

Figure 8:
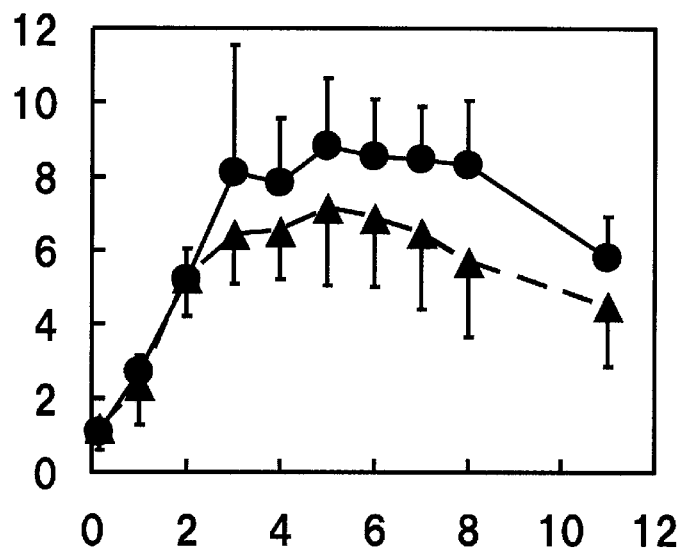
FIG. 8 shows the accumulation of HuRA15-7CTDF-770 antibody (black circle) and MORAb-003DF-770 antibody (black triangle) in advanced cancer resulting from subcutaneous implantation of the platinum-resistant ovarian cancer cell line SKOV-3 into mice, in which the vertical axis represents a ratio of the fluorescence intensity of each antibody to the fluorescence intensity of DNPDF-680 antibody as an internal standard in the tumor site, and the horizontal axis represents time (date) after administration.

As a result, HuRA15-7CTDF-770 antibody was localized remarkably high in the transplanted SKOV-3 tumor and therein for a long time, compared to MORAb-003DF-770 antibody (FIG. 8). These results suggest that the antibody of the present invention showed remarkable accumulation and persistence in advanced cancer derived from the platinum-resistant ovarian cancer cell line SKOV-3 and has higher anti-tumor activity as a cancer therapeutic antibody.

Example 56

Single Administration Test of Cynomolgus Monkey

HuRA15-7CTAcc antibody (100 mg/kg) was intravenously administered into cynomolgus monkey (female, 4-6- old, 3 mice) and the effect was analyzed. General status observation, body weight, feed intake, body temperature, urine test (urinary output, urine specific gravity, urine protein, urine glucose, creatinine, NAG, Na, K, Cl), hematological test (leukocyte, lymphocyte, T cell, Th cell, Tc cell, B cell, NK cell, neutrophil, monocyte, eosinophile, basophile, large unstained cells, erythrocyte, Hb level, Ht value, reticulocyte, platelet, PT, APTT, fibrinogen), blood biochemical test (ALT, ALP, AST, CK, CRP, IL-6, C3, C4, CH50, total bilirubin, total protein, albumin, globulin, triglyceride, total cholesterol, blood sugar, BUN, creatinine, inorganic phosphorus, Ca, Na, K, Cl), autopsy, organ weight, histopathological examination were carried out as test items.

As a result, only slight changes in inflammation and immune response were observed, and the same changes were also observed in placebo administration. Therefore, HuRA15-7CTAcc antibody showed no specific toxicity in all test items.

Example 57

Preparation of HuRA15-7CRAcc Antibody-Expressing Vector

The CDC enhancement technology was applied to the modified HV7LV3 humanized antibody (HuRA15-7CR)-expressing vector (Example 42) in which amino acid substitution of Cys101 with Arg was carried out, in the same manner as in Example 26, so as to prepare a CDC enhancement technology-applied defucosylated HuRA15-7CR (hereinafter, referred to as HuRA15-7CRAcc) antibody-expressing vector.

Example 58

Preparation of HuRA15-7CRAcc Antibody-Expressing Cells

CHO/Ms704 cell was used in the preparation of HuRA15-7CRAcc antibody-expressing cell. In addition, the HuRA15-7CRAcc antibody-expressing vector prepared in Example 57 was used as an expression vector. Typically, subculture, gene transfection, selection of drug-resistant cells and collection of culture supernatant were carried out in the same manner as in Example 7.

Example 59

Purification of HuRA15-7CRAcc Antibody

Purification of HuRA15-7CRAcc antibody from the collected culture supernatant was carried out in the same manner as in Example 8. The concentration was calculated from absorbance index at 280 nm of 1.37 for HuRA15-7CRAcc antibody.

Example 60

Affinity Measurement of HuRA15-7CRAcc Antibody (Surface Plasmon Resonance Method)

Affinity of HuRA15-7CRAcc antibody for FOLR1 was measured by the surface plasmon resonance method. Manipulations were carried out in the same manner as in Example 29 using HuRA15-7CTAcc antibody, HuRA15-7CRAcc antibody, and MORAb-003DF antibody.

As a result, affinities of HuRA15-7CRAcc antibody and MORAb-003DF antibody for FOLR1-mycHis were 2.6% and 1.1% of that of HuRA15-7CTAcc antibody, respectively.

Example 61

Evaluation of ADCC Activity of HuRA15-7CRAcc Antibody

ADCC activities of HuRA15-7CTAcc antibody, HuRA15-7CRAcc antibody, and MORAb-003DF antibody against ovarian cancer cell lines were evaluated in the same manner as in Example 31.

Figure 9:
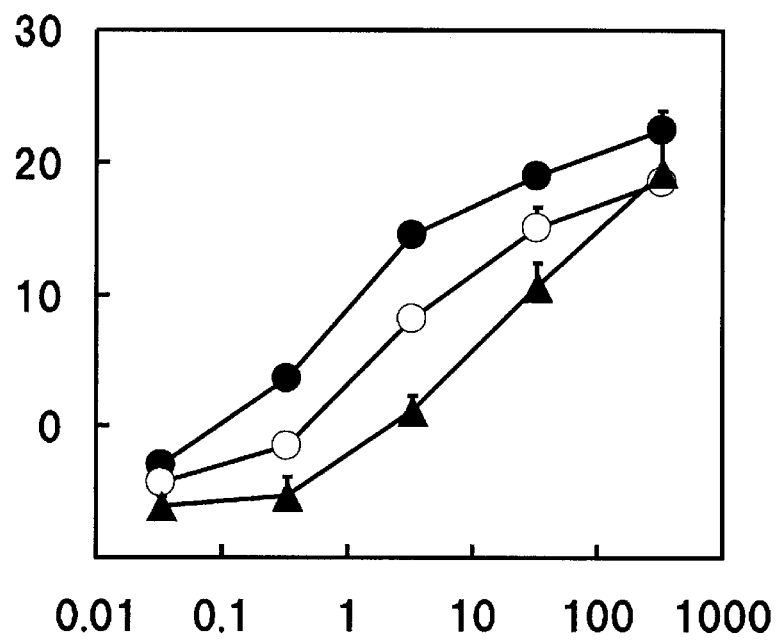
FIG. 9 shows the ADCC activities of HuRA15-7CTAcc antibody (black circle), HuRA15-7CRAcc antibody (white circle), and MORAb-003DF antibody (black triangle) against the platinum-resistant ovarian cancer cell line OVCAR-3, in which the vertical axis represents ADCC activity (%), and the horizontal axis represents antibody concentration (ng/mL).

As a result, ADCC activity against platinum-resistant ovarian cancer cell line OVCAR-3 was observed at a lower concentration in this order of HuRA15-7TAcc antibody, HuRA15-7CRAcc antibody, and MORAB-003DF antibody (FIG. 9). That is, although affinity of HuRA15-7CRAcc antibody is equivalent to that of MORAb-003DF antibody (Example 60), HuRA15-7CRAcc antibody at a lower concentration showed higher ADCC activity than MORAb-003DF. Taken together, it was suggested that the epitope of the RA15-7 clone-derived antibody as well as its affinity strength for FOLR1 is important in order to achieve strong ADCC activity of anti-FOLR1 antibody.

Example 62

Epitope Analysis of HuRA15-7CTAcc Antibody (ELISA)

In the same manner as in Example 35, reactivities of ChRA15-7Acc antibody, MORAb-003 antibody, MOv18 antibody, and HuRA15-7CTAcc antibody were evaluated using FOLR1-mycHis prepared in Example 11 and Rat1-FOLR1-mycHis, Rat2-FOLR1-mycHis, Rat4-FOLR1-mycHis prepared in Example 34.

The results are shown in Table 4. White circle indicates that reaction occurred, and x indicates that no reaction occurred. HuRA15-7CTAcc antibody reacted to FOLR1-mycHis, Rat1-FOLR1-mycHis, and Rat4-FOLR1-mycHis, but did not react to Rat2-FOLR1-mycHis, indicating that HuRA15-7CTAcc antibody recognizes the amino acid sequence at positions 55 to 62 of FOLR1-mycHis, like ChRA15-7Acc antibody.

TABLE 4

|  | HuRA15-7CTAcc antibody |
| --- | --- |
| FOLR1-mycHis | ○ |
| Rat1-FOLR1-mycHis | ○ |
| Rat2-FOLR1-mycHis | X |
| Rat4-FOLR1-mycHis | ○ |

Example 63

Quantitative Analysis of FOLR1 Expressed on Cell Membrane of Ovarian Cancer Cell Line The expression levels of FOLR1 on the cell membrane of ovarian cancer cell lines (IGR-OV1, SKOV-3, OVCAR-3, MCAS) were analyzed using a QIFIKIT (Dako). LK26 (GeneTex) as an anti-FOLR1 antibody and mouse IgG2a (Dako) as a negative control were used at a concentration of 20 μg/mL, respectively to stain cells and calibration beads in accordance with the instructions accompanying QIFIKIT.

Figure 10:
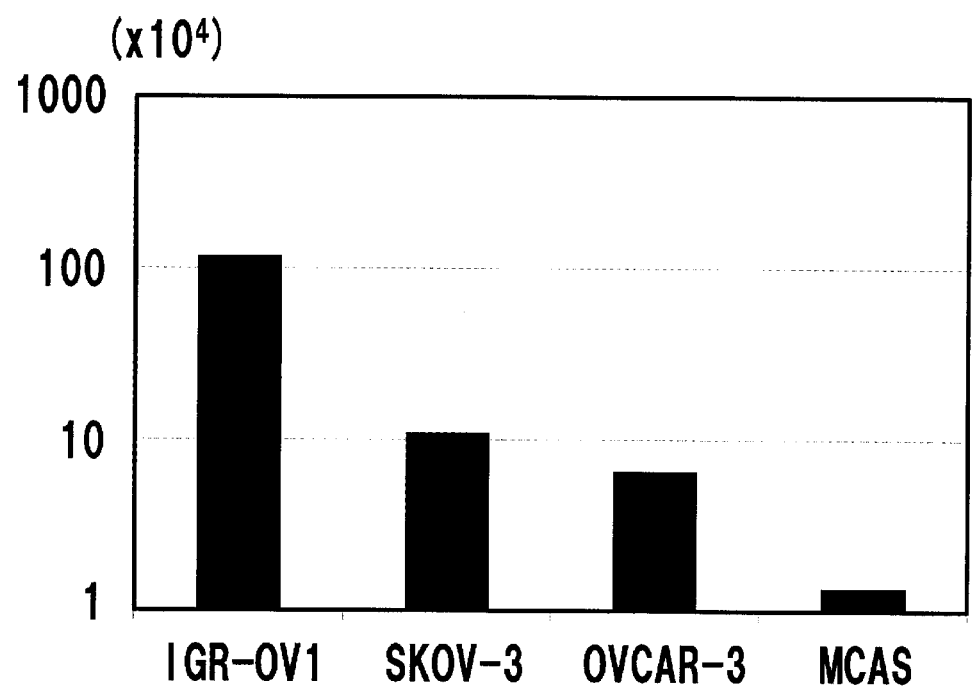
FIG. 10 shows the quantified number of FOLR1 molecule expressed on each ovarian cancer cell line, in which mouse IgG2a was used as a negative control. FOLR1 expressed on ovarian cancer cell line IGR-OV1, SKOV-3, OVCAR-3, or MCAS was analyzed by flow cytometry using LK26 antibody. The vertical axis represents the number of FOLR1 molecules expressed per cell.

Each of the stained cells was prepared in triplicate, and their MFI values were detected by flow cytometry (FIG. 10). The mean MFI values of triplicated samples were used as the MFI value of each cell. Subsequently, MFI values of each cell and calibration bead were entered into ABC CALCULATOR for QIFIKIT provided by Yamasa Corporation, and the number of FOLR1 molecule expressed on ovarian cancer cell lines was determined.

As a result, it was shown that the numbers of FOLR1 molecules expressed on the cell membranes of IGR-OV1, SKOV-3, OVCAR-3, and MCAS were $1.17 \times 10^6$, $1.10 \times 10^5$, $6.63 \times 10^4$, and $1.37 \times 10^4$ molecules per cell, respectively (FIG. 10).

Taken together with the result of Example 54 (FIG. 7), it was revealed that HuRA15-7CTAcc antibody shows the same ADCC activity against both low FOLR1 expressing (the number of FOLR1 molecule on cell membrane: $1 \times 10^4$-$1 \times 10^5$) cells and high FOLR1 expressing (the number of FOLR1 molecule on cell membrane: $1 \times 10^6$) cells. Therefore, it was suggested that this antibody is more useful as a therapeutic antibody for low FOLR1-expressing cancer cells as well as high FOLR1-expressing cancer cells than the conventional antibody (MORAb-003) and the antibody (MORAb-003Acc) prepared by applying the conventional technology to the conventional antibody.

Example 64

Immunohistochemistry of Human Breast Cancer Tissue

In the same manner as in Example 51, human breast cancer tissue array (BioChain) was provided for Immunohistochemistry (IHC). 35 cases of invasive ductal carcinoma tissue, 2 cases of invasive lobular carcinoma tissue, and 3 cases of normal tissue were included in the array, together with negative or positive information of estrogen receptor (ER), progesterone receptor (PR), and Her2.

The result of staining showed that HuRA15-7CTAcc and MORAb-003 antibody positive cells were 56% and 27% in ER-positive/or PR-positive and Her2-negative tissue, 50% and 50% in ER-positive/or PR-positive and Her2-positive tissues, 71% and 14% in ER-negative/or PR-negative and Her2-positive tissue, and 22% and 11% in ER-negative, PR-negative and Her2-negative tissue. From this result, it is revealed that HuRA15-7CTAcc antibody can stain FOLR1-positive breast cancer tissue with higher sensitivity than MORAb-003 antibody.

Further, all H-scores of the tissue samples stained with HuRA15-7CTAcc antibody were higher than those of the same samples stained with MORAb-003 antibody, suggesting that the binding of HuRA15-7CTAcc antibody to FOLR1 expressed in breast cancer is stronger than the conventional antibody MORAb-003.

Example 65

Autologous Depletion Test Using Ovarian Cancer Ascitic Fluid-Derived Cells

The frozen ovarian cancer ascitic fluid-derived cells were purchased from Molecular Response (MR) and the following autologous depletion test was carried out.

First, the frozen ovarian cancer ascitic fluid-derived cells were thawed in a water bath at 37° C., and suspended in a medium for ascitic fluid cell. As the medium for ascitic fluid cell, a medium prepared by adding 10% inactivated FCS, 1/100-fold of Penicillin & Streptomycin (GIBCO), 1/100-fold of non essential amino acid (GIBCO), and 1/100-fold of Sodium Pyruvate (GIBCO) to RPMI1640 GlutaMax (GIBCO) was used.

First, the cell suspension was prepared at a density of $2 \times 10^6$ cells/450 μL, and 450 μL was seeded in each well of 24-well plate. Subsequently, HuRA15-7CTAcc antibody, MORAb-003 antibody, and a negative control DNPDF antibody were prepared at a final concentration of 1-1000 ng/mL using the medium for ascitic fluid cell, and 50 μL/well thereof was added. Thereafter, cells were cultured at 37° C. for 24 hours.

After culture, each well was mixed well by pipetting, and each 250 μL thereof was dispensed in another tubes. Each tube was centrifuged at 200×g and 4° C. for 5 minutes, and the supernatant was discarded. Subsequently, the cell pellet was suspended in 2 mL of Stain Buffer (FBS) (BD Biosciences), followed by centrifugation in the same manner. The supernatant was discarded, followed by cell washing. The cell pellet was suspended in 100 μL of Stain Buffer (FBS), and staining for cancer cell detection and staining for negative control were carried out.

In the staining for cancer cell detection, CD45-PerCP (BD Biosciences), CD14-FITC (BD Biosciences), EpCAM-APC (BD Biosciences), and FOLR1-PE (R&D Systems) were used. In the staining for negative control, CD45-PerCP (BD Biosciences), CD14-FITC (BD Biosciences), mIgG1-APC (BD Biosciences), and mIgG1-PE (BD Biosciences) were used.

They were reacted at room temperature for 30 minutes, and then suspended in 2 mL of Stain Buffer (FBS), followed by centrifugation for washing. After washing, 400 μL of Stain Buffer (FBS) supplemented with 1/100-fold of 7-AAD (BD Biosciences) was added to the cell pellet, and it was suspended and used as a sample to be measured by flow cytometry.

After proper compensation for fluorescent dyes used in cell staining, each sample was subjected to flow cytometry. First, the cell population of 7-AAD-negative(−)/CD45(−)/CD14 (−) was gated, followed by subgating of the population excluding lymphocytes by FSC and SSC. With respect to the cell population, a detection site of mIgG1-APC and mIgG1-PE in the negative control-stained sample was determined, and FOLR1 and EpCAM-positive(+) populations of the staining sample for cancer cell detection were used as cancer cell populations.

In addition, the detection count of 7-AAD(−)/CD14(−)/CD45(+) fraction was measured in a given number, and the number of cells in the cancer cell population was compared between samples.

Figure 11:
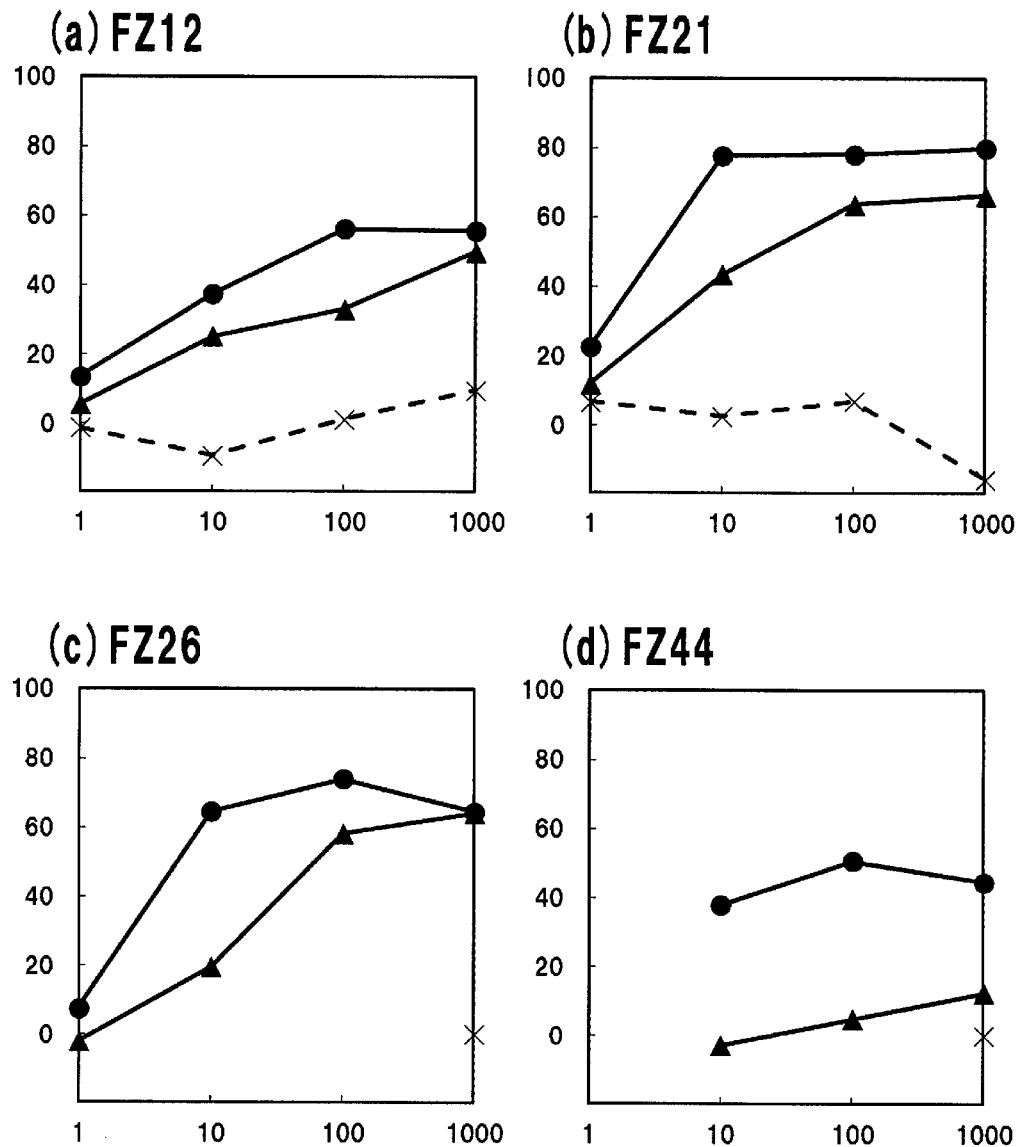
FIGS. 11(a), (b), (c), and (d) show cellular cytotoxicity against FOLR1-positive cells when HuRA15-7CTAcc antibody (black circle), MORAb-003 antibody (black triangle), and DNPDF antibody (x) as a negative control were added to cell populations derived from ovarian cancer ascitic fluid, in which the vertical axis represents cellular cytotoxicity (%), and the horizontal axis represents antibody concentration (ng/mL). FZ12, FZ21, FZ26, and FZ44 represent donors of ovarian cancer ascitic fluid, respectively.

Reduction in the number of cells detected in the cancer cell population by addition of HuRA15-7CTAcc antibody, MORAb-003 antibody, or DNPDF antibody is represented by the vertical axis as cellular cytotoxicity (%) (FIG. 11). The horizontal axis represents antibody concentration (ng/mL).

Herein, FZ12, FZ21, FZ26, and FZ44 in FIG. 11 represent donors of ovarian cancer ascitic fluid (SPECNUM/Patient ID: 2003090712/7028, 2009080521/173089, 2009060526/5208, and 2003041044/113139), respectively. Ex vivo drug resistance test conducted by MR showed that all samples were ovarian cancer ascitic fluid containing cisplatin-resistant cancer cells.

As a result, as shown in FIG. 11, in all samples, HuRA15-7CTAcc antibody at lower concentration showed stronger cellular cytotoxicity than MORAb-003 antibody.

Taken together, when HuRA15-7CTAcc antibody is added to cell populations derived from ascitic fluid of ovarian cancer patients, platinum-resistant cancer cells in ascitic fluid are killed by effector cells in the ascitic fluid. In addition, the cellular cytotoxicity of HuRA15-7CTAcc antibody was found to be higher than that of the conventional ovarian cancer therapeutic antibody MORAb-003.

Example 66

Analysis of FOLR1 Expression Level and Folate Uptake of Ovarian Cancer Cell Line First, FOLR1 expressed on ovarian cancer cell lines, IGR-OV1 (National Cancer Institute), OVISE (JCRB cell NO. JCRB1043), SKOV-3 (ATCC NO. HTB-77), Caov-3 (ATCC NO. HTB-75), RMG-1 (JCRB cell NO. JCRB0172), OV-90 (ATCC NO. CRL-11732), OVCAR-3 (ATCC NO. HTB-161), MCAS (JCRB cell NO. JCRB0240), and TOV-112D (ATCC NO. CRL-11731) was measured by flow cytometry.

Each cell line was cultured, detached using a 0.02% EDTA solution (Nacalai), washed with PBS, and then suspended in FCM buffer (1 mM EDTA, 0.05% sodium azide, 5% inactivated FCS-containing PBS). Subsequently, they were seeded in a density of $1 \times 10^5$ per well in a 96-well plate, followed by centrifugation at 1700 rpm for 1 minute. After the supernatant was discarded, HuRA15-7CTAcc antibody prepared at a concentration of 1 μg/mL using FCM buffer was added, and allowed to react at 4° C. for 30 minutes.

Figure 12:
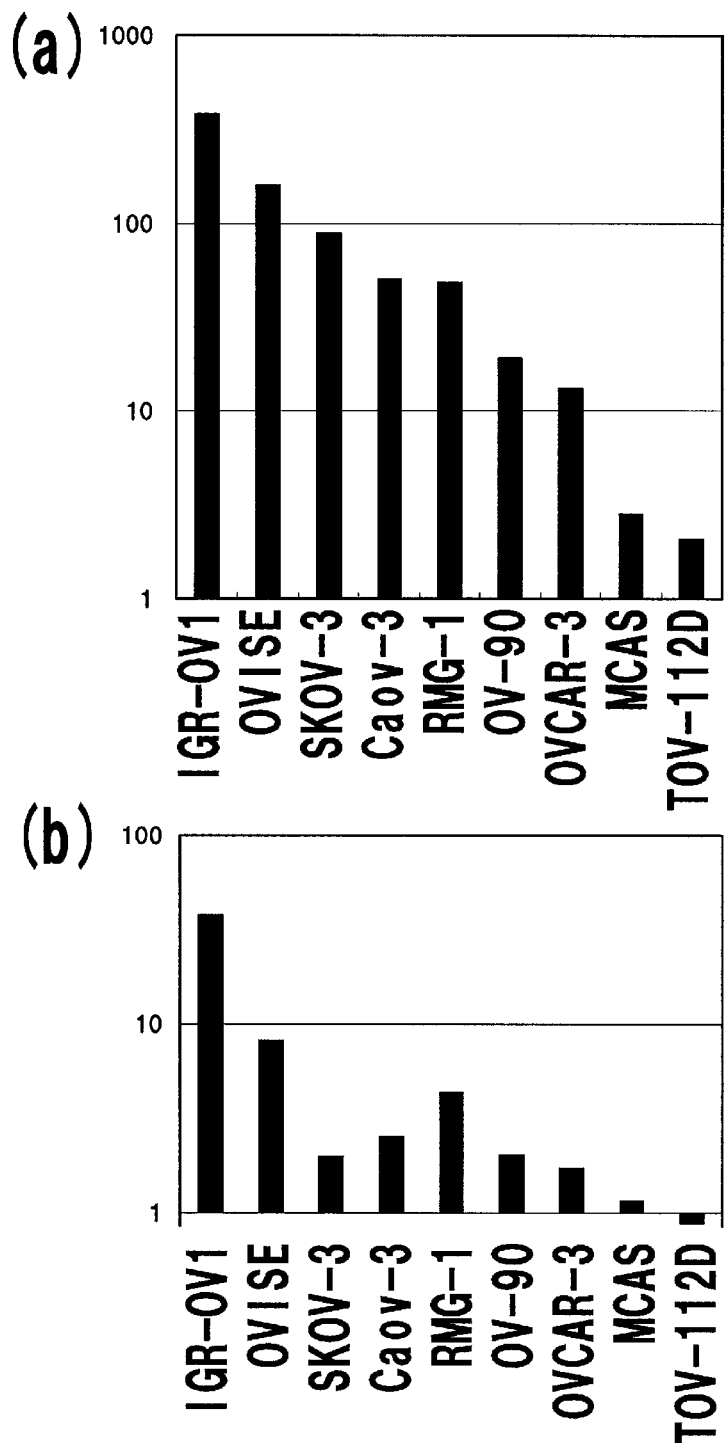
FIGS. 12(a) and (b) show the FOLR1 expression level and folate uptake of various ovarian cancer cell lines.
FIG. 12(b) shows the folate uptake by flow cytometry using labeled folate. The vertical axis represents a MFI value relative to the negative control, and the horizontal axis represents the ovarian cancer cell line analyzed.

After the cells were washed, Anti-Human IgG-FITC (Jackson) diluted 200-fold in FCM buffer was added, and allowed to react at 4° C. for 30 minutes. The cells were washed again, and suspended in FCM buffer, and fluorescence intensity was analyzed by flow cytometry (manufactured by Beckman coulter, FC500MPL) to determine the MFI value of each cell. In the same manner, the MFI value of each cell stained with DNPDF antibody was determined to calculate a relative MFI value of HuRA15-7CTAcc antibody to DNPDF antibody [FIG. 12(a)].

As a result, it was shown that IGR-OV1, OVISE, SKOV-3, Caov-3, RMG-1, OV-90, OVCAR-3, MCAS, and TOV-112D in this order showed higher FOLR1 expression.

Subsequently, the same ovarian cancer cell lines were cultured in a folate-free medium [10% inactivated dialyzed FCS-containing folate-free RPMI1640 (Invitrogen)] for 3 days. Thereafter, labeled folate was added at a final concentration of 100 nM and cultured at 37° C. for 3 hours.

Subsequently, the cells were washed with PBS at 37° C., and then cultured in a 1 mM folate-added medium at 37° C. for 3 hours. The cells were washed with PBS, detached with trypsin (GIBCO), and then suspended in FCM buffer. Fluorescence intensity was analyzed by flow cytometry to determine the MFI value of each cell. In the same manner, the MFI value of cells to which labeled folate was not added was determined to calculate a relative MFI value of 100 nM labeled folate-added sample thereto [FIG. 12(b)].

As a result, there was no correlation between FOLR1 expression level and folate uptake. For example, the FOLR1 expression level of SKOV-3 followed those of IGR-OV1 and OVISE, but its folate uptake was lower than those of IGR-OV1, OVISE, Caov-3, RMG-1, and OV-90. This result suggests that a therapy using anti-cancer agent-conjugated folate may not be effective against cancers with high FOLR1 expression in some cases.

Meanwhile, the antibody of the present invention showed effective cellular cytotoxicity on SKOV-3 or OVCAR-3 with low folate uptake (Example 54). Taken together, it was shown that the antibody of the present invention is effective against cancers which are not susceptible to the anti-tumor activity of the anti-cancer agent-conjugated folate because of their low folate uptake.

While the invention has been described in detail and with reference to specific embodiments thereof, it will be apparent to one skill in the art that various changes and modifications can be made therein without departing from the spirit and scope thereof. On the other hand, this application is based on U.S. provisional application 61/734,610, filed on Dec. 7, 2012 and U.S. provisional application 61/734,547, filed on Dec. 7, 2012, the entire contents of which are incorporated hereinto by reference.

SEQ ID NO. 1: amino acid sequence of FOLR1
SEQ ID NO. 2: nucleotide sequence of FOLR1-F
SEQ ID NO. 3: nucleotide sequence of FOLR1-R
SEQ ID NO. 4: nucleotide sequence of CyFOLR1-F
SEQ ID NO. 5: nucleotide sequence of CyFOLR1-R
SEQ ID NO. 6: nucleotide sequence of CyFOLR1_DNA
SEQ ID NO. 7: amino acid sequence of CyFOLR1_AA
SEQ ID NO. 8: nucleotide sequence of FOLR1-Fc-F
SEQ ID NO. 9: nucleotide sequence of FOLR1-Fc-R
SEQ ID NO. 10: nucleotide sequence of FOLR2-Fc-F
SEQ ID NO. 11: nucleotide sequence of FOLR2-Fc-R
SEQ ID NO. 12: nucleotide sequence of FOLR3-Fc-F
SEQ ID NO. 13: nucleotide sequence of FOLR3-Fc-R
SEQ ID NO. 14: nucleotide sequence of CyFOLR1-Fc-F
SEQ ID NO. 15: nucleotide sequence of CyFOLR1-Fc-R
SEQ ID NO. 16: nucleotide sequence of FOLR1-mH-F
SEQ ID NO. 17: nucleotide sequence of FOLR1-mH-R
SEQ ID NO. 18: nucleotide sequence of RatIgG1H-A
SEQ ID NO. 19: nucleotide sequence of RatIgG1H-B
SEQ ID NO. 20: nucleotide sequence of Ratk-A
SEQ ID NO. 21: nucleotide sequence of Ratk-B
SEQ ID NO. 22: nucleotide sequence of RA15-7VH_DNA
SEQ ID NO. 23: amino acid sequence of RA15-7VH_AA
SEQ ID NO. 24: nucleotide sequence of RA15-7VL_DNA
SEQ ID NO. 25: amino acid sequence of RA15-7VL_AA
SEQ ID NO. 26: nucleotide sequence of nonS_RA15-7VH_DNA
SEQ ID NO. 27: amino acid sequence of nonS_RA15-7VH_AA
SEQ ID NO. 28: nucleotide sequence of nonS_RA15-7VL_DNA
SEQ ID NO. 29: amino acid sequence of nonS_RA15-7VL_AA
SEQ ID NO. 30: amino acid sequence of RA15-7VHCDR1_AA
SEQ ID NO. 31: amino acid sequence of RA15-7VHCDR2_AA
SEQ ID NO. 32: amino acid sequence of RA15-7VHCDR3_AA
SEQ ID NO. 33: amino acid sequence of RA15-7VLCDR1_AA
SEQ ID NO. 34: amino acid sequence of RA15-7VLCDR2_AA
SEQ ID NO. 35: amino acid sequence of RA15-7VLCDR3_AA
SEQ ID NO. 36: nucleotide sequence of RA15-7-VLF
SEQ ID NO. 37: nucleotide sequence of RA15-7-VLR
SEQ ID NO. 38: nucleotide sequence of RA15-7-VHF
SEQ ID NO. 39: nucleotide sequence of RA15-7-VHR
SEQ ID NO. 40: nucleotide sequence of FcAcc_DNA
SEQ ID NO. 41: amino acid sequence of FcAcc_AA
SEQ ID NO. 42: nucleotide sequence of Rat1-FOLR1-mycHis_DNA
SEQ ID NO. 43: nucleotide sequence of Rat2-FOLR1-mycHis_DNA SEQ ID NO. 44: nucleotide sequence of Rat4-FOLR1-mycHis_DNA
SEQ ID NO. 45: amino acid sequence of Rat1-FOLR1-mycHis_AA
SEQ ID NO. 46: amino acid sequence of Rat2-FOLR1-mycHis_AA
SEQ ID NO. 47: amino acid sequence of Rat4-FOLR1-mycHis_AA
SEQ ID NO. 48: nucleotide sequence of HV0
SEQ ID NO. 49: nucleotide sequence of HV2
SEQ ID NO. 50: nucleotide sequence of HV3
SEQ ID NO. 51: nucleotide sequence of HV4
SEQ ID NO. 52: nucleotide sequence of HV5
SEQ ID NO. 53: nucleotide sequence of HV6
SEQ ID NO. 54: nucleotide sequence of HV7
SEQ ID NO. 55: nucleotide sequence of HV8
SEQ ID NO. 56: nucleotide sequence of HV10
SEQ ID NO. 57: nucleotide sequence of LV0
SEQ ID NO. 58: nucleotide sequence of LV2
SEQ ID NO. 59: nucleotide sequence of LV3
SEQ ID NO. 60: nucleotide sequence of LV4
SEQ ID NO. 61: nucleotide sequence of LV6
SEQ ID NO. 62: nucleotide sequence of HuRA15-7HV7_DNA
SEQ ID NO. 63: nucleotide sequence of C101M_DNA
SEQ ID NO. 64: nucleotide sequence of C101G_DNA
SEQ ID NO. 65: nucleotide sequence of C101D_DNA
SEQ ID NO. 66: nucleotide sequence of C101S_DNA
SEQ ID NO. 67: nucleotide sequence of C101Y_DNA
SEQ ID NO. 68: nucleotide sequence of C101A_DNA
SEQ ID NO. 69: nucleotide sequence of C101I_DNA
SEQ ID NO. 70: nucleotide sequence of C101V_DNA
SEQ ID NO. 71: nucleotide sequence of C101T_DNA
SEQ ID NO. 72: nucleotide sequence of C101F_DNA
SEQ ID NO. 73: nucleotide sequence of C101R_DNA
SEQ ID NO. 74: nucleotide sequence of C101W_DNA
SEQ ID NO. 75: nucleotide sequence of C101P_DNA
SEQ ID NO. 76: nucleotide sequence of C101Q_DNA
SEQ ID NO. 77: amino acid sequence of C101M_AA
SEQ ID NO. 78: amino acid sequence of C101G_AA
SEQ ID NO. 79: amino acid sequence of C101D_AA
SEQ ID NO. 80: amino acid sequence of C101S_AA
SEQ ID NO. 81: amino acid sequence of C101Y_AA
SEQ ID NO. 82: amino acid sequence of C101A_AA
SEQ ID NO. 83: amino acid sequence of C101I_AA
SEQ ID NO. 84: amino acid sequence of C101V_AA
SEQ ID NO. 85: amino acid sequence of C101T_AA
SEQ ID NO. 86: amino acid sequence of C101F_AA
SEQ ID NO. 87: amino acid sequence of C101R_AA
SEQ ID NO. 88: amino acid sequence of C101W_AA
SEQ ID NO. 89: amino acid sequence of C101P_AA
SEQ ID NO. 90: amino acid sequence of C101Q_AA
SEQ ID NO. 91: nucleotide sequence of HuRA15-7LV3_DNA
SEQ ID NO. 92: amino acid sequence of HuRA15-7LV3_AA
SEQ ID NO. 93: nucleotide sequence of nonS_HuRA15-7LV3_DNA
SEQ ID NO. 94: amino acid sequence of nonS_HuRA15-7LV3_AA
SEQ ID NO. 95: nucleotide sequence of HuRA15-7CTVH_DNA
SEQ ID NO. 96: amino acid sequence of HuRA15-7CTVH_AA
SEQ ID NO. 97: nucleotide sequence of nonS_HuRA15-7CTVH_DNA
SEQ ID NO. 98: amino acid sequence of nonS_HuRA15-7CTVH_AA
SEQ ID NO. 99: amino acid sequence of HuRA15-7CTVHCDR3_AA
SEQ ID NO. 100: amino acid sequence of HV0_AA
SEQ ID NO. 101: amino acid sequence of LV0_AA
SEQ ID NO. 102: amino acid sequence of Rat FOLR1

What is claimed is:

1. A monoclonal antibody or an antibody fragment thereof, which competes with one antibody selected from the following (a)-(c) to specifically recognize human FOLR1 of SEQ ID NO:1;
which binds to an epitope identical to the epitope on human FOLR1 to which one antibody selected from the following (a)-(c) binds; and
which shows an anti-tumor activity:
(a) an antibody in which complementarity determining regions (CDRs) 1-3 of heavy chain (H chain) of the antibody comprise the amino acid sequences of SEQ ID NOs. 30, 31, and 32, respectively and CDRs 1-3 of light chain (L chain) of the antibody comprise the amino acid sequences of SEQ ID NOs. 33, 34, and 35, respectively;
(b) an antibody in which CDRs 1-3 of H chain of the antibody comprise the amino acid sequences of SEQ ID NOs. 30, 31, and 32, respectively and CDRs 1-3 of L chain of the antibody comprise the amino acid sequences of SEQ ID NOs. 33, 34, and 35, respectively, and in which cysteine in the amino acid sequence of SEQ ID NO. 32 is substituted with threonine, methionine, isoleucine, valine, phenylalanine, or glutamine; and
(c) an antibody in which H chain of the antibody comprises the amino acid sequence of SEQ ID NO. 98, and L chain of the antibody comprises the amino acid sequence of SEQ ID NO. 94.

2. The monoclonal antibody or the antibody fragment thereof according to claim 1, which is a recombinant antibody.

3. The monoclonal antibody or the antibody fragment thereof according to claim 2, wherein the recombinant antibody is selected from a human chimeric antibody, a humanized antibody and a human antibody.

4. A monoclonal antibody or an antibody fragment thereof that is selected from the following (a)-(c):
(a) a monoclonal antibody and an antibody fragment thereof in which complementarity determining regions (CDRs) 1-3 of H chain of the antibody comprise the amino acid sequences of SEQ ID NOs. 30, 31, and 32, respectively and CDRs 1-3 of L chain of the antibody comprise the amino acid sequences of SEQ ID NOs. 33, 34, and 35, respectively;
(b) an antibody in which CDRs 1-3 of H chain of the antibody comprise the amino acid sequences of SEQ ID NOs. 30, 31, and 32, respectively and CDRs 1-3 of L chain of the antibody comprise the amino acid sequences of SEQ ID NOs. 33, 34, and 35, respectively, and in which cysteine in the amino acid sequence of SEQ ID NO. 32 is substituted with threonine, methionine, isoleucine, valine, phenylalanine, or glutamine; and (c) an antibody in which H chain of the antibody comprises the amino acid sequence of SEQ ID NO. 98, and L chain of the antibody comprises the amino acid sequence of SEQ ID NO. 94.

5. The monoclonal antibody and the antibody fragment thereof according to any one of claims 1 to 4, wherein the antibody fragment is selected from Fab, Fab', F(ab')$_2$, a single chain antibody, a dimeric V region, a disulfide-stabilized V region, and a peptide comprising CDRs 1-3 of H chain and CDRs 1-3 of L chain.

6. A pharmaceutical composition comprising the monoclonal antibody or the antibody fragment thereof of any one of claims 1 to 4 and a pharmaceutically acceptable carrier.

* * * * *